US011465957B1

(12) United States Patent
Drennan et al.

(10) Patent No.: US 11,465,957 B1
(45) Date of Patent: *Oct. 11, 2022

(54) METHODS AND SYSTEMS FOR CRYSTALLIZING AND ISOLATING INDIVIDUAL CANNABINOIDS

(71) Applicant: MYKU Biosciences LLC, Denver, CO (US)

(72) Inventors: Timothy Drennan, Los Angeles, CA (US); Matthew Petrina, Lakewood, CO (US)

(73) Assignee: MYKU Biosciences LLC, Denver, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/687,248

(22) Filed: Mar. 4, 2022

Related U.S. Application Data

(63) Continuation of application No. 17/494,898, filed on Oct. 6, 2021.

(60) Provisional application No. 63/172,244, filed on Apr. 8, 2021.

(51) Int. Cl.
*C07C 37/84* (2006.01)

(52) U.S. Cl.
CPC .......... *C07C 37/84* (2013.01); *C07C 2601/16* (2017.05)

(58) Field of Classification Search
CPC ..................................................... C07C 37/84
See application file for complete search history.

(56) References Cited

U.S. PATENT DOCUMENTS

| 8,481,085 B2 | 7/2013 | Musty et al. |
| 2008/0031977 A1 | 2/2008 | Musty et al. |

OTHER PUBLICATIONS

Appending, et al., "Antibacterial Cannabinoids from *Cannabis sativa*: A Structure-Activity Study". J. Nat Prod. (Aug. 2008); 71(8): 1427-1430. Epub Aug. 6, 2008.
Assareh, et al., "Cannabidiol disrupts conditioned fear expression and cannabidiolic acid reduces trauma-induced anxiety-related behaviour in mice". Behav Pharmacol. (Sep. 2020); 31(6): 591-596.
[Author Unknown] "How to make THCA Crystals & Solventless Sauce". 2001-2021, https://www.alchimiaweb.com/blogen/make-thca-crystals-solventless-sauce/, 17 pages.
Borrelli, et al., "Beneficial effect of the non-psychotropic plant cannabinoid cannabigerol on experimental inflammatory bowel disease". Biochem Pharmacol (May 1, 2013); 85(9): 1306-1316. Epub Feb. 12, 2013.
Borrelli, et al., "Colon carcinogenesis is inhibited by the TRPM8 antagonist cannabigerol, a Cannabis-derived non-psychotropic cannabinoid". Carcinogenesis (Dec. 2014); 35(12): 2787-2797. Epub Sep. 30, 2014.
Brenneisen, R., "Chemistry and Analysis of Phytocannabinoids and Other Cannabis Constituents". Marijuana and the Cannabinoids, (ed Mahmoud A. ElSohly, PhD, Forensic Science and Medicine (2007); Ch. 2, pp. 17-49, 43 pages.
Cascio, et al., "The phytocannabinoid, Δ9-tetrahydrocannabivarin, can act through 5-HT1A receptors to produce antipsychotic effects". British Journal of Pharmacology (Mar. 2015); 172(5): 1305-1318.
Colasanti, et al., "Intraocular pressure, ocular toxicity and neurotoxicity after administration of cannabinol or cannabigerol". Experimental Eye Research (Sep. 1984); 39(3): 251-259.
Consroe, P, et al., "Open label evaluation of cannabidiol in dystonic movement disorders". International Journal of Neuroscience. (Jan. 1, 1986); 30(4): 277-282.
Co-pending U.S. Appl. No. 17/494,898, inventor DRENNAN; Timothy, filed Oct. 6, 2021.
De Meijer, E. P., et al., "The inheritance of chemical phenotype in *Cannabis sativa* L.(III): variation in cannabichromene proportion". Euphytica (Jan. 2009); 165(2): 293-311.
De Meijer, E. P., et al., "The inheritance of chemical phenotype in *Cannabis sativa* L.(IV): cannabinoid-free plants". Euphytica (Jul. 2009); 168(1): 95-112.
De Meijer, E.P, et al., "The inheritance of chemical phenotype in *Cannabis sativa* L". Genetics (Jan. 1, 2003); 163(1): 335-346.
De Meijer, E.P., et al., "The inheritance of chemical phenotype in *Cannabis sativa* L.(II): cannabigerol predominant plants". Euphytica (Sep. 2005); 145(1): 189-198.
De Zeeuw, R.A., et al., "Cannabinoids with a propyl side chain in cannabis: Occurrence and chromatographic behavior". Science (Feb. 18, 1972); 175(4023): 778-779.
El-Alfy, A.T., et al., "Antidepressant-like effect of Δ9-tetrahydrocannabinol and other cannabinoids isolated from *Cannabis sativa* L". Pharmacology Biochemistry and Behavior (Jun. 1, 2010); 95(4): 434-442.
Eubanks, L. M., et al., "A molecular link between the active component of marijuana and Alzheimer's disease pathology". Molecular Pharmaceutics (Dec. 4, 2006); 3(6): 773-777.
Flores-Sanchez, et al., "PKS activities and biosynthesis of cannabinoids and flavonoids in *Cannabis sativa* L. plants". Plant and Cell Physiology (Dec. 1, 2008); 49(12): 1767-1782.
Galletta, et al., "Rapid Antibacterial Activity of Cannabichromenic Acid against Methicillin-Resistant *Staphylococcus aureus*". Antibiotics (Aug. 16, 2020); 9(8): 523, 11 pages.
Herring and Kaminski, "Cannabinol-Mediated Inhibition of Nuclear Factor-κB, cAMP Response Element-Binding Protein, and Interleukin-2 Secretion by Activated Thymocytes". Journal of Pharmacology and Experimental Therapeutics (Dec. 1999); 291(3): 1156-1163.
Hill, et al., "Cannabidivarin-rich cannabis extracts are anticonvulsant in mouse and rat via a CB1 receptor-independent mechanism". Br J Pharmacol. (Oct. 2013); 170(3): 679-692. First Published: Jul. 31, 2013.
Hill, et al., "Δ9-Tetrahydrocannabivarin suppresses in vitro epileptiform and in vivo seizure activity in adult rats". Epilepsia (Aug. 2010); 51(8): 1522-1532. Epub Feb. 26, 2010.

(Continued)

*Primary Examiner* — Sikarl A Witherspoon
(74) *Attorney, Agent, or Firm* — Cooley LLP

(57) ABSTRACT

The present disclosure provides methods for selectively crystallizing cannabinoids from solutions containing a plurality of cannabinoids. The present disclosure further provides methods for separating a crystallized cannabinoid from a mixture of cannabinoids.

30 Claims, 33 Drawing Sheets

(56) References Cited

OTHER PUBLICATIONS

Hoaken, P. N., et al., "Drugs of abuse and the elicitation of human aggressive behavior". Addictive Behaviors (Dec. 1, 2003); 28(9):1533-1554.

Holley, J.H., et al., "Constituents of *Cannabis sativa* L. XI: Cannabidiol and cannabichromene in samples of known geographical origin". Journal of Pharmaceutical Sciences (May 1975); 64(5): 892-895.

Marks, M.D., et al., "Identification of candidate genes affecting Δ9-tetrahydrocannabinol biosynthesis in *Cannabis sativa*". Journal of Experimental Botany (Sep. 1, 2009); 60(13): 3715-3726.

Mcallister, S.D., et al., "Cannabidiol as a novel inhibitor of Id-1 gene expression in aggressive breast cancer cells". Molecular Cancer Therapeutics (Nov. 1, 2007); 6(11): 2921-2927.

Mechoulam, R., et al., "Cannabidiol-recent advances". Chemistry & Biodiversity (Aug. 2007); 4(8): 1678-1692.

Morgan, C.J., et al., "Impact of cannabidiol on the acute memory and psychotomimetic effects of smoked cannabis: naturalistic study". The British Journal of Psychiatry (Oct. 2010); 197(4): 285-290.

Muscarà, et al., "Antioxidant and antimicrobial activity of two standardized extracts from a new Chinese accession of non-psychotropic *Cannabis sativa* L". Phytother Res. (Feb. 2021); 35(2): 1099-1112. Epub Oct. 9, 2020.

Nicholson, A.N., et al., "Effect of Δ-9-tetrahydrocannabinol and cannabidiol on nocturnal sleep and early-morning behavior in young adults". Journal of Clinical Psychopharmacology (Jun. 1, 2004); 24(3): 305-313.

Paul, "How to Crystallize CBD—Make CBD Isolate". Mar. 13, 2019, B/R Instrument Blog, https://brinstrument.com/blog/cannabis-distillation/how-to-crystallize-cbd-make-cbd-isolate/, 12 pages.

Pertwee, R. G., "The pharmacology of cannabinoid receptors and their ligands: an overview". International Journal of Obesity (Apr. 2006); 30(1): S13-S18.

Petrocellis, et al., "Cannabinoid actions at TRPV channels: effects on TRPV3 and TRPV4 and their potential relevance to gastrointestinal inflammation". Acta Physiol (Oxf). (Feb. 2012); 204(2): 255-266. Epub Aug. 12, 2011.

Pickens, J.T., "Sedative activity of cannabis in relation to its Δ'-trans-tetrahydrocannabinol and cannabidiol content". British Journal of Pharmacology (Apr. 1981); 72(4): 649-656.

Romano, et al., "The cannabinoid TRPA1 agonist cannabichromene inhibits nitric oxide production in macrophages and ameliorates murine colitis". Br J Pharmacol. (May 2013); 169(1): 213-229.

Ruhaak, et al., "Evaluation of the cyclooxygenase inhibiting effects of six major cannabinoids isolated from *Cannabis sativa*". Biol Pharm Bull. (2011); 34(5): 774-778.

Russo, E.B., "Taming THC: potential cannabis synergy and phytocannabinoid-terpenoid entourage effects" The British Journal of Pharmacology (2011); 164 (7): 1344-1364.

Schute, Viviane, "How To Make THCA Rosin". Oct. 26, 2020, https://thepressclub.co/blogs/tips-tricks/how-to-make-thca-rosin?_pos=1&_sid=78879f223&_ss=r, 8 pages.

Shrader, et al., "Involvement of dopamine receptor in the actions of non-psychoactive phytocannabinoids". Biochemical and Biophysical Research Communications (Dec. 17, 2020); 533(4): 1366-1370.

Smeriglio, et al., "Inhibition of aldose reductase activity by *Cannabis sativa* chemotypes extracts with high content of cannabidiol or cannabigerol". Fitoterapia. (Jun. 2018); 127: 101-108. Epub Feb. 7, 2018.

Valdeolivas, et al., "Neuroprotective Properties of Cannabigerol in Huntington's Disease: Studies in R6/2 Mice and 3-Nitropropionate-lesioned Mice". Neurotherapeutics (Jan. 2015); 12(1): 185-199.

Vigli, et al., "Chronic Treatment with Cannabidiolic Acid (CBDA) Reduces Thermal Pain Sensitivity in Male Mice and Rescues the Hyperalgesia in a Mouse Model of Rett Syndrome". Neuroscience (Jan. 15, 2021); 453: 113-123. Epub Sep. 30, 2020.

Yona, Eran, "Cannabinoids Crystallization—doing it right!" Nov. 17, 2019, https://cannabisgxp.com/2019/11/17/cannabinoids-crystallization-doing-it-right/#:~:text=Crystallization%20is%20an%20essential%20process,achieving%20%3E99%25%20purity%20level, 6 pages.

Zuardi, A.W., et al., "Cannabidiol, a *Cannabis sativa* constituent, as an antipsychotic drug". Brazilian Journal of Medical and Biological Research (2006); 39: 421-429.

METHODS AND SYSTEMS FOR CRYSTALLIZING AND ISOLATING INDIVIDUAL CANNABINOIDS

CROSS-REFERENCE TO RELATED APPLICATIONS

This application is a continuation of U.S. application Ser. No. 17/494,898, filed Oct. 6, 2021, which claims the benefit of priority to U.S. Provisional Application No. 63/172,244, filed on Apr. 8, 2021. The contents of the aforementioned patent documents are incorporated by reference herein in their entirety.

FIELD

The present disclosure generally relates to methods of selectively crystallizing and purifying cannabinoids from a mixture of cannabinoids.

BACKGROUND

*Cannabis* has over 80 active constituents with potential therapeutic benefits. For instance, research shows that cannabinoids isolated from *Cannabis* stabilize blood sugar, provide relief from chronic pain, help with weight loss, improve depression and anxiety, prevent seizures, and allow broken bones to heal more quickly.

The most common extraction methods used to isolate cannabinoids use solvents such as ethanol, hexane, butane, pentane, or propane. These methods require tightly regulated environments, because the aforementioned solvents are flammable. Furthermore, these methods result in chemical impurities in the extracted cannabinoid compositions, which can produce undesirable color, tastes/smells, and may even be dangerous for human consumption.

There is a need in the art for safer methods of extracting and purifying cannabinoids from *Cannabis*.

SUMMARY

There is an unmet need for improved methods for extraction and purification of cannabinoids. The present disclosure provides methods of extracting and purifying cannabinoids from *Cannabis* that do not use traditional solvents or require expensive processing equipment. The methods provided herein do not require ethanol winterization, pentane or hexane solvation and crystallization, or ether washes. Nor do the methods require expensive explosive proof equipment or solvent reactors. The methods described herein result in pure cannabinoid compositions. In some embodiments, the pure cannabinoid products are organic, because the methods of producing them do not utilize non-organic solvents. Additionally, the methods for extraction and purification of cannabinoids described herein are zero waste processes, because the byproducts are used in further refining processes.

Provided herein is a method of selectively crystallizing a selected cannabinoid from a solution of cannabinoids, comprising: (a) providing a solution containing a plurality of cannabinoids, wherein the selected cannabinoid is present in the solution at a concentration greater than or equal to its supersaturation point at −5° C., and wherein the selected cannabinoid is the highest concentration cannabinoid in the solution, and wherein said solution is substantially free of any exogenous solvent; (b) increasing the temperature of the solution until the selected cannabinoid is substantially dissolved in the solution; and (c) decreasing the temperature of the solution to about −5° C. or lower to produce a cooled solution wherein the selected cannabinoid crystallizes out of solution, thereby forming crystals of the selected cannabinoid. In some embodiments, the solution is a primary *cannabis* extract. In some embodiments, step (b) comprises increasing the temperature to between about 50° C. and about 79° C. In some embodiments, step (c) comprises decreasing the temperature to between about −5° C. and about −20° C. In some embodiments, the cooled solution is exposed to a nucleation factor, wherein the nucleation factor is selected from the group consisting of introducing a crystal of the selected cannabinoid into the cooled solution, introducing the cooled solution to a vacuum or a vacuum oven, mechanically agitating the cooled solution, increasing or maintaining the moisture content of the cooled solution, and aerating the cooled solution. In some embodiments, the selected cannabinoid is selected from the group consisting of cannabidiol (CBD), tetrahydrocannabinol (THC), tetrahydrocannabivarin (THCV), cannabidiolic acid (CBDA), cannabidivarin (CBDV), tetrahydrocannabinolic acid (THCA), cannabigerol (CBG), cannabinol (CBN), cannabinolic acid (CBNA), cannabidivarinic acid (CBDVA), cannabigerolic acid (CBGA), cannabichromenic acid (CBCA), and cannabichromene (CBC). In some embodiments, the solution of cannabinoids is a *Cannabis* oil that is substantially free of cutting agents. In some embodiments, the solution of cannabinoids comprises less than 1%, 0.9%, 0.8%, 0.7%, 0.6%, 0.5%, 0.4%, 0.3%, 0.2%, or 0.1% exogenous solvents. In some embodiments, 95% of the selected cannabinoid is crystallized out of the cooled solution. In some embodiments, the selected cannabinoid crystallizes out of solution within about 10 hours. In some embodiments, a vacuum is applied to the cooled solution. In some embodiments, the crystals of the selected cannabinoid comprise crystals that are greater than about 25 μm in size.

In some embodiments, provided herein is a method of purifying a selected cannabinoid from a mixture of cannabinoids, said method comprising: (a) providing a mixture of cannabinoids comprising a crystallized cannabinoid, wherein the crystallized cannabinoid comprises crystals that are at least about 25 μm in size; (b) forcing the mixture of cannabinoids through a filter, said filter having a pore size smaller than about 25 μm; wherein this step is performed at a temperature below the melting point of the crystallized cannabinoid, wherein the crystallized cannabinoid remains on the filter; and (c) collecting the crystallized cannabinoid from the filter, thereby purifying the selected cannabinoid. In some embodiments, step (b) is performed between about 0.5° C. and 10° C. below the melting point of the crystallized cannabinoid. In some embodiments, the selected cannabinoid is selected from the group consisting of consisting of cannabidiol (CBD), tetrahydrocannabinol (THC), tetrahydrocannabivarin (THCV), cannabidiolic acid (CBDA), cannabidivarin (CBDV), tetrahydrocannabinolic acid (THCA), cannabigerol (CBG), cannabigerolic acid (CBGA), cannabinol (CBN), cannabinolic acid (CBNA), cannabidivarinic acid (CBDVA), cannabichromenic acid (CBCA), and cannabichromene (CBC). In some embodiments, the mixture of cannabinoids is forced through the filter via centrifugation, application of pressure, or application of a vacuum. In some embodiments, the crystallized cannabinoid is washed with a solvent at a temperature between about 1° C. and 8° C. In some embodiments, the collected crystallized cannabinoid is at least 98% pure.

In some embodiments, provided herein is a method of purifying a selected cannabinoid from a solution containing a plurality of cannabinoids, comprising: (a) selectively crystallizing the selected cannabinoid from the solution by: (i) increasing the temperature of the solution until the selected cannabinoid is substantially dissolved in the solution, wherein the selected cannabinoid is present in the solution at a concentration greater than or equal to its supersaturation point; and wherein the selected cannabinoid is the highest concentration cannabinoid in the solution; (ii) decreasing the temperature of the solution to about −5° C. or lower to produce a cooled solution wherein 95% of the selected cannabinoid has crystallized out of solution into cannabinoid crystals; and (b) separating the selected cannabinoid crystals from the cooled solution. In some embodiments, the cannabinoid is separated from the cooled solution by: (i) forcing the cooled solution through a filter, said filter having a pore size smaller than about 2 µm or smaller than about 25 µm; wherein this step is performed at a temperature below the melting point of the crystallized cannabinoid; and (ii) collecting the crystallized cannabinoid from the filter, thereby separating the selected cannabinoid from the cooled solution. In some embodiments, the mixture of cannabinoids is forced through the filter via centrifugation, application of pressure, or application of a vacuum. In some embodiments, the temperature of the solution is increased in step (a)(i) to between about 50° C. and about 79° C. In some embodiments, the temperature of the solution is decreased in step (a)(ii) to below about −5° C. In some embodiments, the method comprises exposing the cooled solution to a nucleation factor, wherein the nucleation factor is selected from the group consisting of introducing a crystal of the selected cannabinoid into the cooled solution, introducing the cooled solution to a vacuum or a vacuum oven, mechanically agitating the cooled solution, increasing or maintaining the selected cannabinoid is selected from the group consisting of cannabidiol (CBD), tetrahydrocannabinol (THC), tetrahydrocannabivarin (THCV), cannabidiolic acid (CBDA), cannabidivarin (CBDV), tetrahydrocannabinolic acid (THCA), cannabigerol (CBG), cannabigerolic acid (CBGA), cannabinol (CBN), cannabinolic acid (CBNA), cannabidivarinic acid (CBDVA), cannabichromenic acid (CBCA), and cannabichromene (CBC). In some embodiments, the solution of cannabinoids is a *Cannabis* oil that does not contain any cutting agents. In some embodiments, the solution of cannabinoids comprises less than 1%, 0.9%, 0.8%, 0.7%, 0.6%, 0.5%, 0.4%, 0.3%, 0.2%, or 0.1% exogenous solvents. In some embodiments, 95% of the selected cannabinoid is crystallized out of the cooled solution. In some embodiments, the selected cannabinoid crystallizes out of solution within about 10 hours. In some embodiments, the method comprises applying a vacuum to the cooled solution. In some embodiments, the crystals of the selected cannabinoid comprise crystals that are at least about 25 µm in size.

Provided herein is a method for purifying a selected cannabinoid from a solution containing a plurality of cannabinoids, comprising: (a) selectively crystallizing the selected cannabinoid from the solution by: (i) increasing the temperature of the solution until the selected cannabinoid is substantially dissolved in the solution, wherein the selected cannabinoid is present in the solution at a concentration greater than or equal to its supersaturation point; and wherein the selected cannabinoid is the highest concentration cannabinoid in the solution; (ii) decreasing the temperature of the solution to about −5° C. or lower to produce a cooled solution wherein 95% of the selected cannabinoid has crystallized out of solution into cannabinoid crystals; (b) separating the selected cannabinoid crystals from the cooled solution by forcing the cooled solution through a filter via centrifugation, said filter having a pore size smaller than about 2 µm; wherein this step is performed at a temperature below the melting point of the crystallized cannabinoid; and (c) collecting the crystallized cannabinoid from the filter, thereby separating the selected cannabinoid from the cooled solution. In some embodiments, the method comprises exposing the cooled solution to a nucleation factor, wherein the nucleation factor is selected from the group consisting of introducing a crystal of the selected cannabinoid into the cooled solution, introducing the cooled solution to a vacuum or a vacuum oven, mechanically agitating the cooled solution, increasing or maintaining the moisture content of the cooled solution, and aerating the cooled solution. In some embodiments, the nucleation factor comprises mechanically agitating the cooled solution, introducing the cooled solution to a vacuum or a vacuum oven, or combinations thereof. In some embodiments, the nucleation factor comprises mechanically agitating the cooled solution, introducing a crystal of the selected cannabinoid into the cooled solution, and introducing the cooled solution to a vacuum or a vacuum oven, or combinations thereof.

Provided herein is a method of purifying a selected cannabinoid from a solution containing a plurality of cannabinoids, comprising: (a) selectively crystallizing the selected cannabinoid from the solution by: (i) increasing the temperature of the solution until the selected cannabinoid is substantially dissolved in the solution; (ii) decreasing the temperature of the solution to about −5° C. or lower to produce a cooled solution wherein 95% of the selected cannabinoid has crystallized out of solution into cannabinoid crystals; (b) separating the selected cannabinoid crystals from the cooled solution by forcing the cooled solution through a filter via centrifugation, said filter having a pore size smaller than about 2 µm; wherein this step is performed at a temperature below the melting point of the crystallized cannabinoid; and (c) collecting the crystallized cannabinoid from the filter, thereby separating the selected cannabinoid from the cooled solution. In some embodiments, the method comprises exposing the cooled solution to a nucleation factor, wherein the nucleation factor is selected from the group consisting of introducing a crystal of the selected cannabinoid into the cooled solution, introducing the cooled solution to a vacuum or a vacuum oven, mechanically agitating the cooled solution, increasing or maintaining the moisture content of the cooled solution, and aerating the cooled solution. In some embodiments, the nucleation factor comprises mechanically agitating the cooled solution, introducing the cooled solution to a vacuum or a vacuum oven, or combinations thereof. In some embodiments, the nucleation factor comprises mechanically agitating the cooled solution, introducing a crystal of the selected cannabinoid into the cooled solution, and introducing the cooled solution to a vacuum or a vacuum oven, or combinations thereof. In some embodiments, the selected cannabinoid is present in the solution containing a plurality of cannabinoids at a concentration of greater than 10% by weight of the solution.

Provided herein is a method of crystallizing a selected cannabinoid from a cannabinoid solution, comprising: (a) providing a cannabinoid solution containing a substantially dissolved selected cannabinoid, wherein the selected cannabinoid is present in the solution at a concentration greater than or equal to its supersaturation point, and wherein the selected cannabinoid is the highest concentration cannabinoid in the solution; and (b) exposing the cannabinoid solution of step (a) to nucleation factors comprising mechanical agitation and a vacuum for a time period sufficient to crystallize the selected cannabinoid. In some embodiments, the solution of (a) is produced by increasing the temperature of a cannabinoid solution until the selected cannabinoid is substantially dissolved in the solution. In some embodiments, the solution of (a) is produced by increasing the temperature of a cannabinoid solution until the selected cannabinoid is substantially dissolved in the solution, wherein the temperature is increased to from about 50° C. and about 79° C. In some embodiments, the supersaturation point is greater than or equal to 30% by weight of the solution. In some embodiments, the cannabinoid solution is substantially free of any alcohol. In some embodiments, the cannabinoid solution comprises less than 15%, less than 10%, or less than 5% alcohol by weight of the solution. In some embodiments, the cannabinoid solution is substantially free of any exogenous solvent. In some embodiments, the cannabinoid solution comprises less than 15%, less than 10%, or less than 5% exogenous solvent by weight of the solution. In some embodiments, the method comprises exposing the dissolved cannabinoid solution to an additional nucleation factor, wherein the nucleation factor is selected from the group consisting of: cold shock, introducing a crystal of the selected cannabinoid into the dissolved cannabinoid solution, aerating the solution, and combinations thereof. In some embodiments, the method comprises mechanically agitating the dissolved cannabinoid solution before exposing the cannabinoid solution to the vacuum, while the cannabinoid solution is exposed to the vacuum, or a combination thereof. In some embodiments, the selected cannabinoid is selected from the group consisting of cannabidiol (CBD), tetrahydrocannabinol (THC), tetrahydrocannabivarin (THCV), cannabidiolic acid (CBDA), cannabidivarin (CBDV), tetrahydrocannabinolic acid (THCA), cannabigerol (CBG), cannabinol (CBN), cannabinolic acid (CBNA), cannabidivarinic acid (CBDVA), cannabigerolic acid (CBGA), cannabichromenic acid (CBCA), and cannabichromene (CBC). In some embodiments, the selected cannabinoid is CBD. In some embodiments, the vacuum is stronger than about −5 inHg. In some embodiments, the method provides crystallization of at least 70% of the selected cannabinoid by weight of the solution within 48 hours.

Provided herein is a method of purifying a selected cannabinoid from a solution of cannabinoids, said method comprising: (a) crystallizing the selected cannabinoid from the solution by: (i) providing a cannabinoid solution containing a substantially dissolved selected cannabinoid, wherein the selected cannabinoid is present in the solution at a concentration greater than or equal to its supersaturation point, and wherein the selected cannabinoid is the highest concentration cannabinoid in the solution; (ii) exposing the cannabinoid solution of step (a)(i) to a nucleation factor for a time period sufficient to crystallize the selected cannabinoid, wherein the nucleation factor is mechanical agitation and vacuum, thereby producing cannabinoid crystals; and (b) separating the selected cannabinoid crystals from the cannabinoid solution of step (a)(ii). In some embodiments, the cannabinoid solution is substantially free of any alcohol. In some embodiments, the cannabinoid solution comprises less than 15%, less than 10%, or less than 5% alcohol by weight of the solution. In some embodiments, the cannabinoid solution is substantially free of any exogenous solvent. In some embodiments, the cannabinoid solution comprises less than 15%, less than 10%, or less than 5% exogenous solvent by weight of the solution. In some embodiments, step (b) comprises (i) forcing the cannabinoid solution and cannabinoid crystals through a filter; wherein this step is performed at a temperature below the melting point of the cannabinoid crystals; and (ii) collecting the cannabinoid crystals from the filter, thereby separating the selected cannabinoid from the cannabinoid solution. In some embodiments, step (b) comprises (i) forcing the cannabinoid solution and cannabinoid crystals through a filter via centrifugation, application of pressure, or application of a vacuum; wherein this step is performed at a temperature below the melting point of the cannabinoid crystals; and (ii) collecting the cannabinoid crystals from the filter, thereby separating the selected cannabinoid from the cannabinoid solution. In some embodiments, step (b) comprises (i) forcing the cannabinoid solution and cannabinoid crystals through a filter via centrifugation; wherein this step is performed at a temperature below the melting point of the cannabinoid crystals; and (ii) collecting the cannabinoid crystals from the filter, thereby separating the selected cannabinoid from the cannabinoid solution. In some embodiments, the solution of (a) is produced by increasing the temperature of the cannabinoid solution until the selected cannabinoid is substantially dissolved in the solution. In some embodiments, the temperature is increased to between about 50° C. and about 79° C. In some embodiments, the supersaturation point is greater than or equal to 30% by weight of the solution. In some embodiments, the method comprises exposing the dissolved cannabinoid solution to an additional nucleation factor, wherein the nucleation factor is selected from the group consisting of: cold shock, introducing a crystal of the selected cannabinoid into the dissolved cannabinoid solution, aerating the solution, and combinations thereof. In some embodiments, the method comprises mechanically agitating the dissolved cannabinoid solution before exposing the cannabinoid solution to the vacuum, while the cannabinoid solution is exposed to the vacuum, or a combination thereof. In some embodiments, the selected cannabinoid is selected from the group consisting of cannabidiol (CBD), tetrahydrocannabinol (THC), tetrahydrocannabivarin (THCV), cannabidiolic acid (CBDA), cannabidivarin (CBDV), tetrahydrocannabinolic acid (THCA), cannabigerol (CBG), cannabinol (CBN), cannabinolic acid (CBNA), cannabidivarinic acid (CBDVA), cannabigerolic acid (CBGA), cannabichromenic acid (CBCA), and cannabichromene (CBC). In some embodiments, the selected cannabinoid is CBD. In some embodiments, the vacuum is stronger than about −5 inHg. In some embodiments, the method provides crystallization of at least 70% of the selected cannabinoid by weight of the solution within 48 hours.

In some embodiments, provided herein is a method of purifying a selected cannabinoid from a cannabinoid solution, said method comprising: (a) crystallizing the selected cannabinoid from the solution by: (i) providing a cannabinoid solution containing a substantially dissolved selected cannabinoid, wherein the selected cannabinoid is present in the solution at a concentration greater than or equal to its supersaturation point; (ii) exposing the cannabinoid solution of step (a)(i) to a nucleation factor for a time period sufficient to crystallize the selected cannabinoid, wherein the nucleation factor is mechanical agitation and vacuum, thereby producing cannabinoid crystals; and (b) separating the selected cannabinoid crystals from the cannabinoid solution of step (a)(ii) by: (i) forcing the cannabinoid solution through a filter; wherein this step is performed at a temperature below the melting point of the cannabinoid crystals; and (ii) collecting the cannabinoid crystals from the filter, thereby separating the selected cannabinoid from the cannabinoid solution. In some embodiments, the method provides crystallization of at least 70% of the selected cannabinoid by weight of the solution within 48 hours.

BRIEF DESCRIPTION OF THE DRAWINGS

FIG. 7A is an image of a solution containing a plurality of cannabinoids 24 hours after temperature modulation. No nucleation factor is added to the solution of FIG. 7A. FIG. 7B is an image of a solution containing a plurality of cannabinoids 24 hours after exposure to a vacuum oven and cold-shocked (after 24 hours). FIG. 7C is an image of a solution containing a plurality of cannabinoids 24 hours after the solution is mechanically agitated and cold-shocked. FIG. 7D is an image of a solution containing a plurality of cannabinoids 24 hours after a seed crystal is introduced to a solution that has been cold-shocked. FIG. 7E is an image of a solution containing a plurality of cannabinoids before a seed crystal is introduced to a solution and after the solution has been cold-shocked. FIG. 7F is an image of a solution containing a plurality of cannabinoids 24 hours after a seed crystal is introduced to the solution and the solution is mechanically agitated. FIG. 7G is an image of a solution containing a plurality of cannabinoids 24 hours after the solution is mechanically agitated and exposed to a vacuum oven. FIG. 7H is an image of a solution containing a plurality of cannabinoids 24 hours after a seed crystal is introduced to the solution and the solution is mechanically agitated, cold-shocked, and exposed to a vacuum oven. FIG. 7I is an image of a solution containing a plurality of cannabinoids 24 hours after a seed crystal is introduced to the solution and the solution is exposed to a vacuum oven. FIG. 7J shows images of the CBD crystals of the samples of FIG. 7I, FIG. 7H, FIG. 7G, and FIG. 7B (left to right).

FIG. 14A shows crystallization of CBD when CBD is present in the solution at a concentration of 31.3% w/w. The cloudy layer on top is CBD crystals. The bottom layer is MCT coconut oil. At the interface of the coconut oil and crystals, crystals appear to proceed into the MCT coconut oil layer. FIG. 14B shows crystallization of CBD when CBD is present in the solution at a concentration of 19.6% w/w. FIG. 14C shows crystallization of CBD when CBD is present in the solution at a concentration of 15.7% w/w. FIG. 14D shows crystallization of CBD when CBD is present in the solution at a concentration of 11.7% w/w. FIG. 14E shows crystallization of CBD when CBD is present in the solution at a concentration of 7.8% w/w. FIG. 14F shows crystallization of CBD when CBD is present in the solution at a concentration of 3.9% w/w.

Figure 15A:
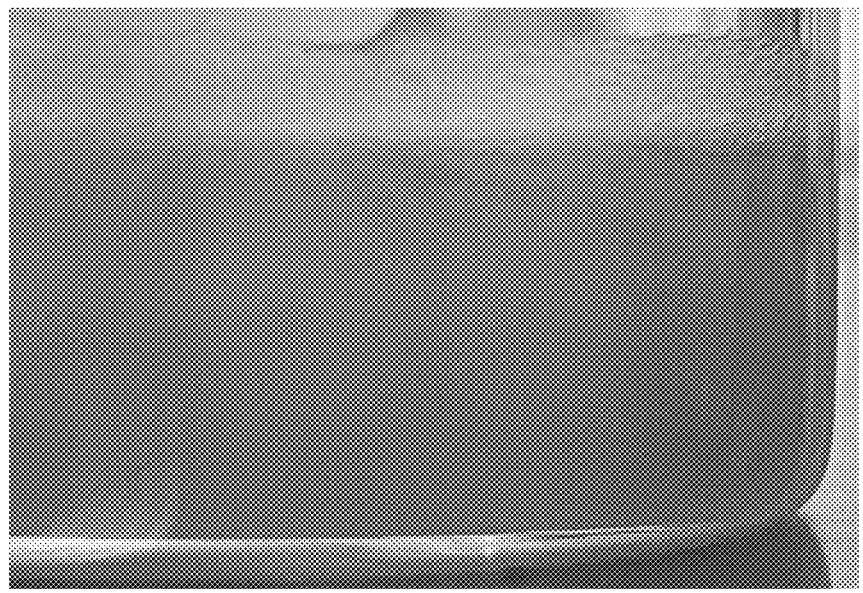
FIGS. 15A-J show cannabinoid samples allowed to crystallize naturally. Samples 9 (FIG. 15A), 4 (FIG. 15B), 1 (FIG. 15C), and 8 (FIG. 15D) only crystallized after 95 days. Samples 2 (FIG. 15E), 5 (FIG. 15F), 3 (FIG. 15G), 6 (FIG.
Figure 15B:
Figure 15C:
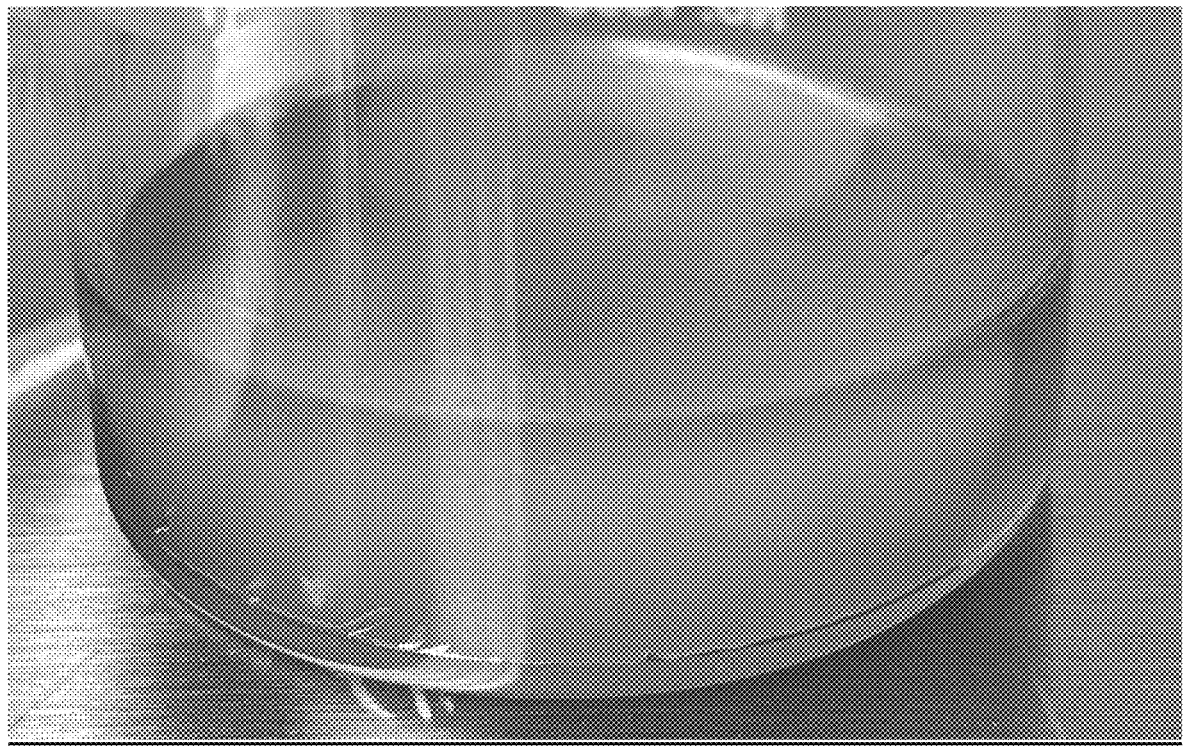
Figure 15D:
Figure 15E:
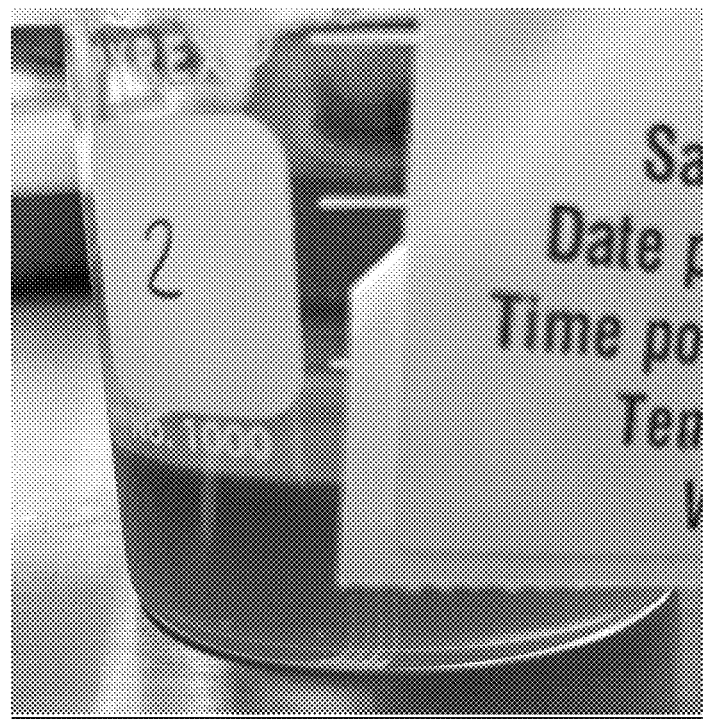
Figure 15F:
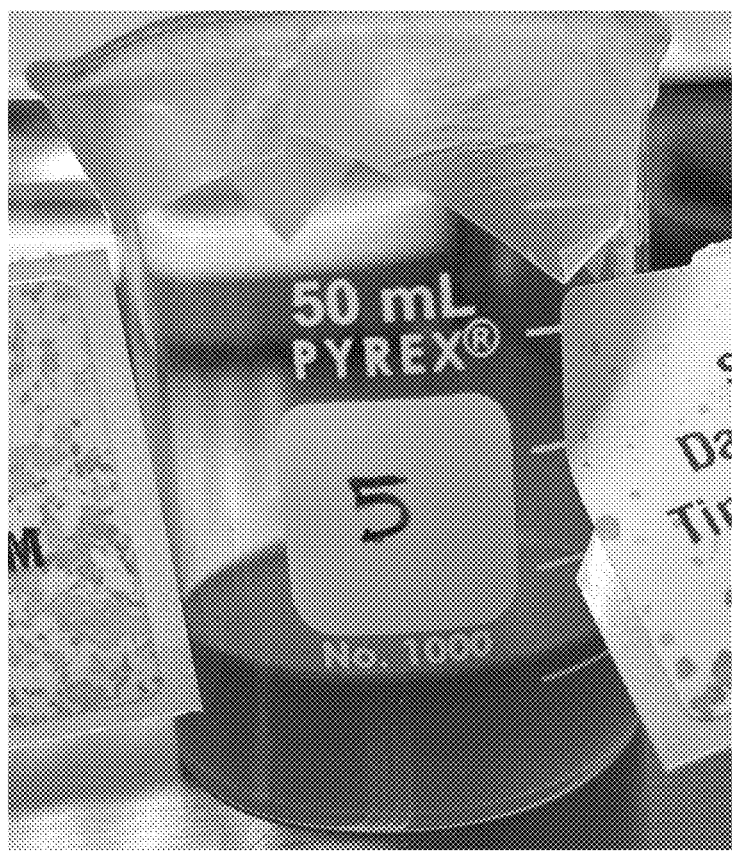
Figure 15G:
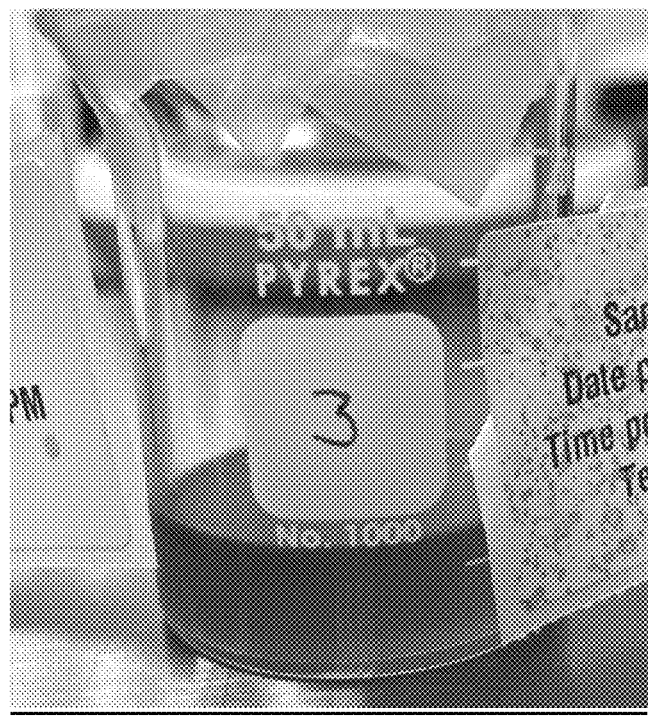
Figure 15H:
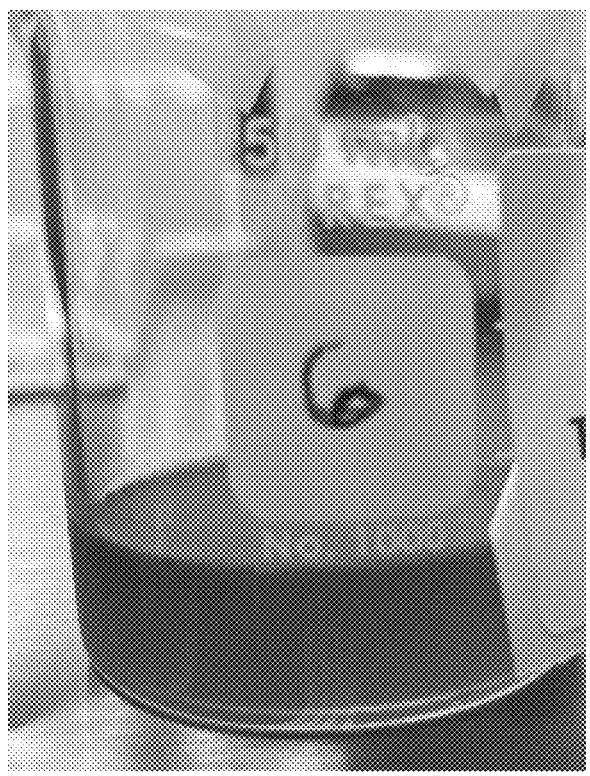
Figure 15I:
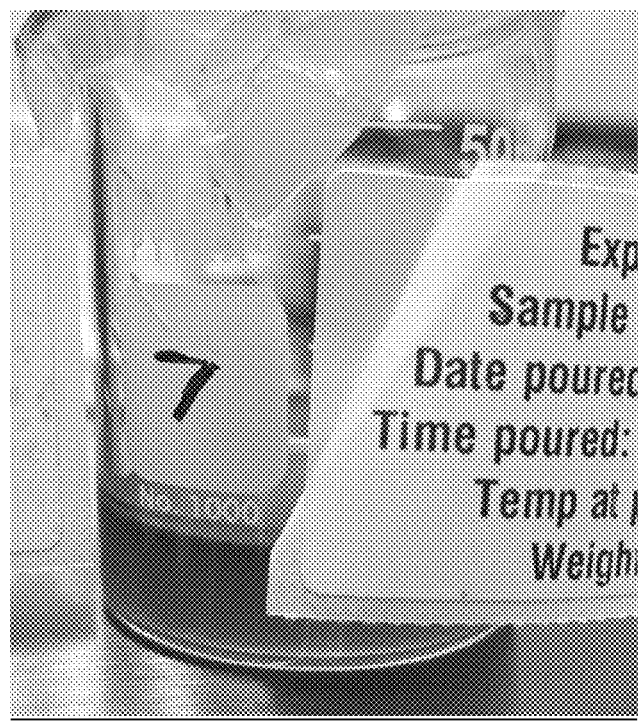
Figure 15J:
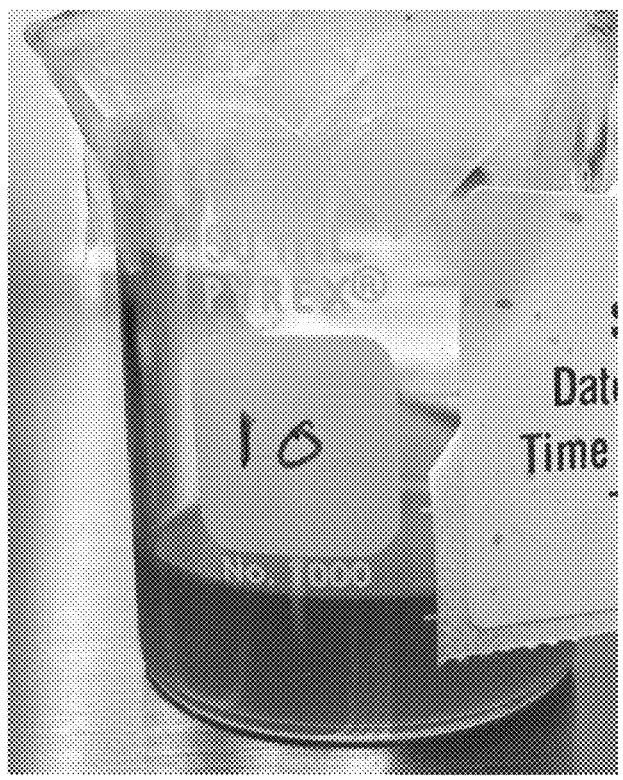

15H), 7 (FIG. 15I), and 10 (FIG. 15J) did not crystallize at all during the period of observation (95 days).

Figure 16:
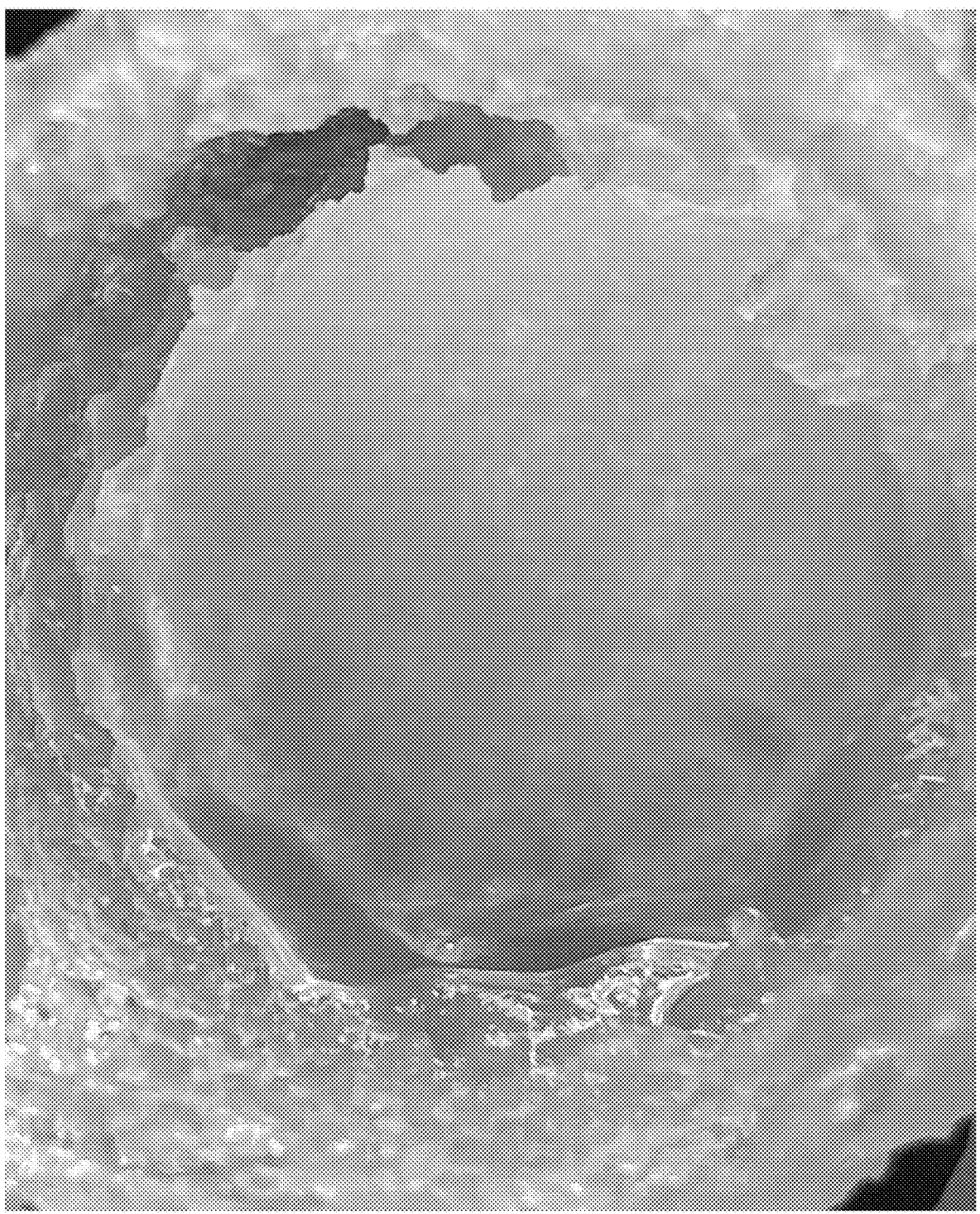

FIG. 16 shows crystallization of CBD from a solution containing 24% CBD, 1% THCA, and 75% oleic acid.

Figure 17A:
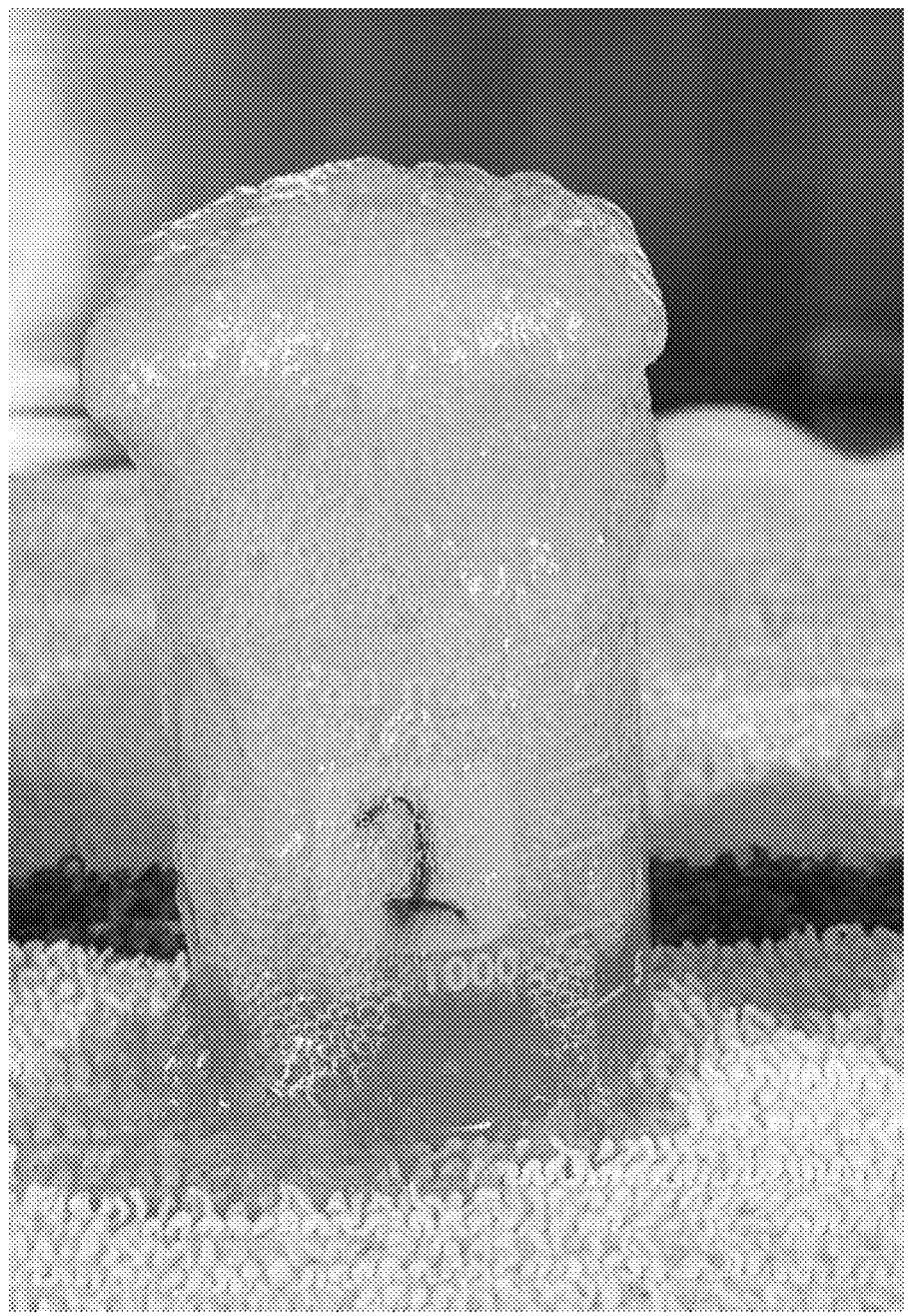

FIG. 17A shows the effect of introducing a vacuum nucleation factor to a cannabinoid solution. The microbubbles in the image are uniform and have expanded as a result of exposure to the vacuum.

Figure 17B:
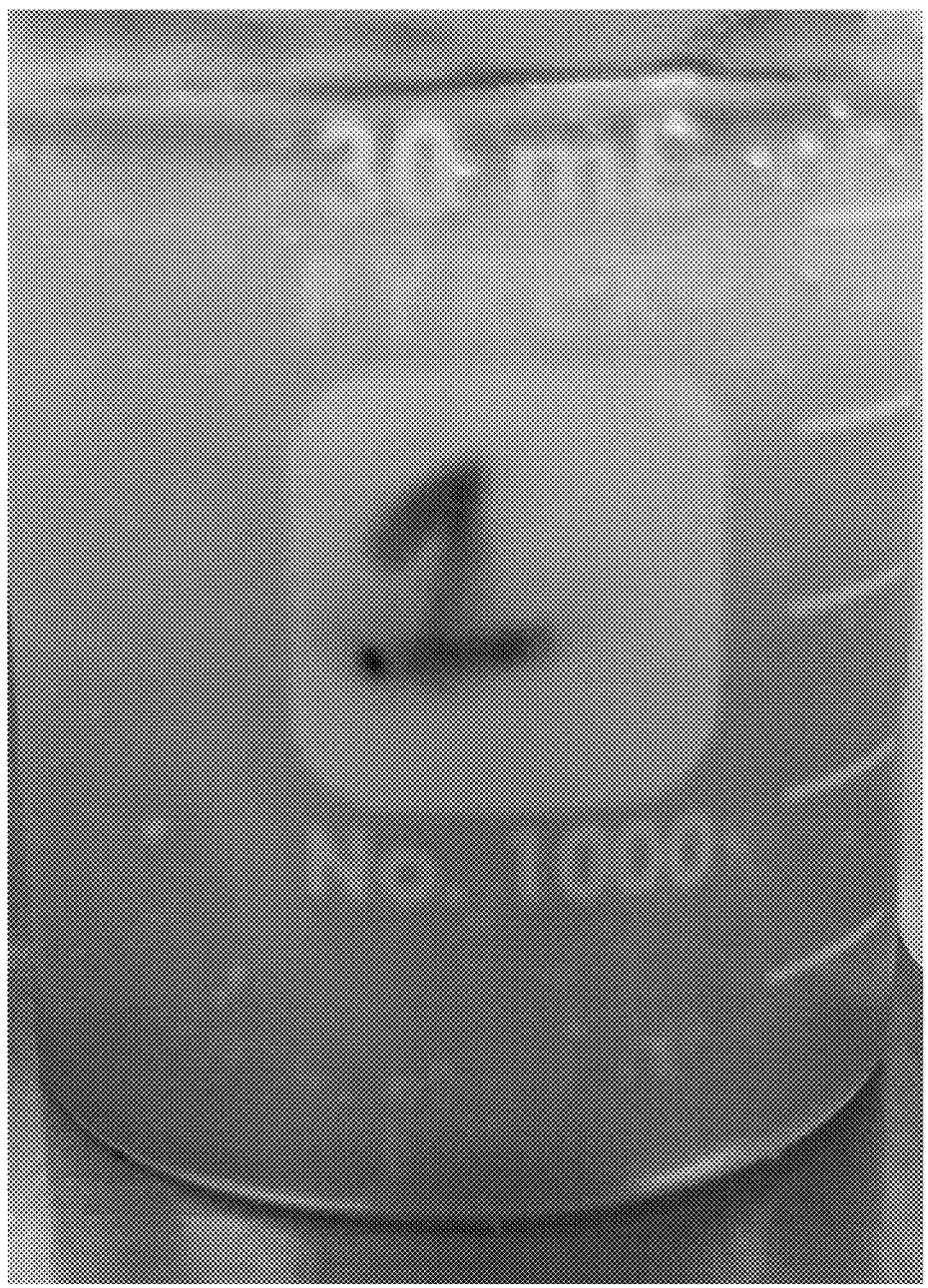

FIG. 17B shows the effect of agitating and applying cold shock to a cannabinoid solution. These nucleation factors thicken the cannabinoid solution and result in bubble formation which aids cannabinoid nucleation.

DETAILED DESCRIPTION

I. Definitions

The term "a" or "an" refers to one or more of that entity, i.e., can refer to a plural referent. As such, the terms "a" or "an", "one or more" and "at least one" are used interchangeably herein. In addition, reference to "an element" by the indefinite article "a" or "an" does not exclude the possibility that more than one of the elements is present, unless the context clearly requires that there is one and only one of the elements.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

Throughout this application, the term "about" is used to indicate that a value includes the inherent variation that exists among the samples being measured. Unless otherwise stated or otherwise evident from the context, the term "about" means within 10% above or below the reported numerical value (except where such number would exceed 100% of a possible value or go below 0%). When used in conjunction with a range or series of values, the term "about" applies to the endpoints of the range or each of the values enumerated in the series, unless otherwise indicated. As used in this application, the terms "about" and "approximately" are used as equivalents.

Herein, the terms "comprise", or variations such as "comprises" or "comprising", will be understood to imply the inclusion of a stated element or integer or group of elements or integers but not the exclusion of any other element or integer or group of elements or integers.

As used within the context of this application, the term "purified" means extracted, isolated, and/or separated from other compounds, formulations, compositions, matter, and/or mass. In some embodiments, a cannabinoid may be separated from other cannabinoids, terpenes, waxes, and fats.

The term "reference value" or "control value" refers to a value or measurement obtained from an experimental control group or to a baseline value (e.g., purity) obtained from a solution containing a plurality of cannabinoids prior to performance of the methods of the disclosure.

The term "substantially pure" refers to a cannabinoid having a chromatographic purity of greater than about 95% by weight, greater than about 96% by weight, greater than about 97% by weight, greater than about 98% by weight, or greater than about 99% by weight.

The term "*Cannabis* plant part" refers to any part of a *Cannabis* plant including but not limited to the embryo, shoot, root, stem, seed, stipule, leaf, petal, flower, inflorescence, bud, ovule, bract, trichome, branch, petiole, internode, bark, pubescence, tiller, rhizome, frond, blade, pollen, stamen, mesocarp, epicarp, endosperm, spermoderm, and disk.

The term "cannabinoid composition" refers to a composition comprising at least one cannabinoid, for example, at least one, two, three, four, five, six, seven, eight, nine, ten, 11, 12, 13, 14, 15, 16, 17, 18, 19, or 20 cannabinoids.

Various concentration expressions, including volume concentrations, weight concentrations, and mass concentrations, are utilized to describe the percentage of a component in a solution. Volume concentration has units of % v/v, where v/v is volume per volume. If a solution contains 5% v/v of a component, 5 mL of the component is in a total solution of 100 mL, for example. Weight concentration of a solution is expressed as % w/w, where w/w is weight per weight. If a solution contains 30% w/w of sodium chloride, an example solution contains 30 g of sodium chloride and 70 g of other components of the solution, such as the solvent. Mass concentration of a solution is expressed as % w/v, where w/v is weight per volume. If 1 g of sodium chloride is dissolved in a solution with a total volume of 100 mL, a 1% w/v sodium chloride solution has been made.

As used herein, the term "exogenous solvent" refers to any solvent that is not derived from the *Cannabis* plant. Exogeneous solvents include, but are not limited to, ethanol, isopropanol, hexane, methyl ethyl ketone, acetone, ethyl ether, butane, propane, and liquid CO2.

The term "selectively" as it refers to crystallizing a selected cannabinoid means that the selected cannabinoid is crystallized at a larger rate than other compounds within a cannabinoid solution (e.g., other cannabinoids). For example, if CBD is selectively crystallized from a cannabinoid solution containing CBD, THC, and CBG, a greater proportion of the CBD in solution will be crystallized than the proportion of other cannabinoids in the solution. Applicant notes that small amounts of non-selected cannabinoids are sometimes detected in the crystals recovered from a solution, but the concentration of these cannabinoids is greatly reduced after filtering and wash steps, suggesting that these non-selected cannabinoids were not crystallized, but were instead liquid contaminants on the surface of the selected cannabinoid crystals.

II. *Cannabis*

*Cannabis* is a genus of flowering plants that includes three different species, *Cannabis sativa, Cannabis indica* and *Cannabis ruderalis*. There are 483 identifiable chemical constituents known to exist in the *cannabis* plant (Rudolf Brenneisen (2007) in Marijuana and the Cannabinoids, ElSohly, ed.; incorporated herein by reference), including at least 85 different cannabinoids and over 120 terpenes (El-Alfy, Abir T, et al. (2010) Pharmacology Biochemistry and Behavior 95 (4): 434-42; incorporated herein by reference).

The two most well-known cannabinoids produced by *Cannabis* plants are tetrahydrocannabinol (THC) and cannabidiol (CBD).

IIA. Cannabinoids

Cannabinoids are a unique family of terpeno-phenolic compounds produced by *Cannabis* plants. Typical cannabinoids isolated from *Cannabis* plants include, but are not limited to, Cannabigerolic Acid (CBGA), Cannabigerolic Acid monomethylether (CBGAM), Cannabigerol (CBG), Cannabigerol monomethylether (CBGM), Cannabigerovarinic Acid (CBGVA), Cannabigerovarin (CBGV), Cannabichromenic Acid (CBCA), Cannabichromene (CBC), Cannabichromevarinic Acid (CBCVA), Cannabichromevarin (CBCV), Cannabidiolic Acid (CBDA), Cannabidiol (CBD), Cannabidiol monomethylether (CBDM), Cannabidiol-C4 (CBD-C4), Cannabidivarinic Acid (CBDVA), Cannabidivarin (CBDV), Cannabidiorcol (CBD-C1), Tetrahydrocannabinolic acid A (THCA-A), Tetrahydrocannabinolic acid B (THCA-B), Tetrahydrocannabinolic Acid (THCA), Tetrahydrocannabinol (THC), Tetrahydrocannabinolic acid C4 (THCA-C4), Tetrahydrocannabinol C4(THC-C4), Tetrahydrocannabivarinic acid (THCVA), Tetrahydrocannabivarin (THCV), Tetrahydrocannabinolic acid-C4 (THCA-C4), Tetrahydrocannabinol-C1 (THC-C1), Δ7-cis-iso-tetrahydrocannabivarin, Δ8-tetrahydrocannabinolic acid (Δ8-THCA), Cannabivarinodiolic (CBNDVA), Cannabivarinodiol (CBNDV), Δ8-tetrahydrocannabinol (Δ8-THC), Δ9-tetrahydrocannabinol (Δ9-THC), Cannabicyclolic acid (CBLA), Cannabicyclol (CBL), Cannabicyclovarin (CBLV), Cannabielsoic acid A (CBEA-A), Cannabielsoic acid B (CBEA-B), Cannabielsoin (CBE), Cannabivarinselsoin (CBEV), Cannabivarinselsoinic Acid (CBEVA), Cannabielsoic Acid (CBEA), Cannabielvarinsoin (CBLV), Cannabielvarinsoinic Acid (CBLVA), Cannabinolic acid (CBNA), Cannabinol (CBN), Cannabivarinic Acid (CBNVA), Cannabinol methylether (CBNM), Cannabinol-C4 (CBN-C4), Cannabivarin (CBV), Cannabino-C2 (CBN-C2), Cannabiorcol (CBN-C1), Cannabinodiol (CBND), Cannabinodiolic Acid (CBNDA), Cannabinodivarin (CBDV), Cannabitriol (CBT), 10-Ethoxy-9-hydroxy-Δ6a-tetrahydrocannabinol, 8,9-Dihydroxy-Δ6a(10a)-tetrahydrocannabinol (8,9-Di-OH-CBT-Δ5), Cannabitriolvarin (CBTV), Ethoxy-cannabitriolvarin (CBTVE), Dehydrocannabifuran (DCBF), Cannbifuran (CBF), Cannabichromanon (CBCN), Cannabicitran (CBT), 10-Oxo-Δ6a(10a)-tetrahydrocannabinol (OTHC), Δ9-cis-tetrahydrocannabinol (cis-THC), Cannabiripsol (CBR), 3,4,5,6-tetrahydro-7-hydroxy-alpha-alpha-2-trimethyl-9-n-propyl-2,6-methano-2H-1-benzoxocin-5-methanol (OH-iso-HHCV), Trihydroxy-delta-9-tetrahydrocannabinol (triOH-THC), Yangonin, Epigallocatechin gallate, Dodeca-2E, 4E, 8Z, 10Z-tetraenoic acid isobutylamide, and Dodeca-2E,4E-dienoic acid isobutylamide. See Holley et al. (1975) J. Pharm. Sci. 64:892-894 and De Zeeuw et al. (9172) Science 175:778-779, each of which is herein incorporated by reference in its entirety for all purposes.

Most cannabinoids exist in two forms, as acids and in neutral (decarboxylated) forms. The acid form is designated by an "A" at the end of its acronym (i.e. THCA). The phytocannabinoids are synthesized in the plant as acid forms, and while some decarboxylation does occur in the plant, it increases significantly post-harvest and the kinetics increase at high temperatures. (Sanchez and Verpoorte 2008). Cannabinoids in their acid forms (those ending in "-A") can be converted to their non-acidic forms through a process called decarboxylation. While some decarboxylation (e.g., neutralization) of cannabinoids does occur in the plant, production of the neutral forms increases significantly post-harvest. (Sanchez and Verpoorte (2008) Plant Cell Physiol. December: 49(12)). Full decarboxylation of phytocannabinoids can be catalyzed by post-cultivation heating *cannabis* plant material or extracted cannabinoids (e.g., by combustion, vaporization, or baking in an oven).

In order to find the total amount of non-acidic cannabinoid, the total measured content of acid cannabinoid variants forms should be adjusted to account for the loss of the carboxyl group. In some embodiments, this adjustment can be made by multiplying the molar content of the acidic cannabinoid forms by the molecular weight of the corresponding decarboxylated cannabinoid. Other shorthand conversions are also available for quickly converting acidic cannabinoid content to active cannabinoid content.

For example, in some embodiments, THCA can be converted to active THC using the formula: THCA×0.877=THC. When using this approach, the maximum THC for the sample is: THCmax=(THCA×0.877)+THC. This method has been validated according to the principles of the International Conference on Harmonization. Similarly, CBDA can be converted to active CBD and the yield is determined using the yield formula: CBDA×0.877=CBD. Also, the maximum amount of CBD yielded, i.e. max CBD for the sample is: CBDmax=(CBDA×0.877)+CBD. Additionally, CBGA can be converted to active CBG by multiplying CBGA by 0.878 (CBGmax=(CBGA×0.878)+CBG).

In some embodiments, provided herein are methods of selectively crystallizing and/or purifying a cannabinoid from a solution containing a plurality of cannabinoids. In some embodiments, any of the cannabinoids listed above may be selectively crystallized and/or purified according to the methods of the disclosure. In some embodiments, cannabidiol (CBD), tetrahydrocannabinol (THC), tetrahydrocannabivarin (THCV), cannabidiolic acid (CBDA), cannabidivarin (CBDV), tetrahydrocannabinolic acid (THCA), cannabigerol (CBG), cannabigerolic acid (CBGA), cannabinol (CBN), cannabinolic acid (CBNA), cannabidivarinic acid (CBDVA), cannabichromenic acid (CBCA), or cannabichromene (CBC) are selectively crystallized and/or purified according to the methods of this disclosure.

Brief descriptions and chemical structures of the aforementioned cannabinoids are provided below.

Cannabidiol (CBD)

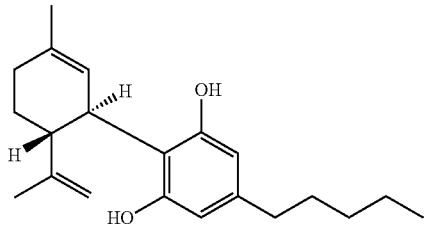

CBD is a cannabinoid found in *Cannabis* shown to display sedative effects in animal tests (Pickens, (1981) Br. J. Pharmacol. 72 (4): 649-56). Some research, however, indicates that CBD can increase alertness, and attenuates the memory-impairing effect of THC. (Nicholson et al., June (2004) J Clin Psychopharmacol 24 (3): 305-13; Morgan et al., (2010) The British Journal of Psychiatry, 197:258-290). CBD may also decrease the rate of THC clearance from the body, perhaps by interfering with the metabolism of THC in the liver. Medically, CBD has been shown to relieve convulsion, inflammation, anxiety, and nausea, as well as inhibit cancer cell growth (Mechoulam, et al., 2007, Chemistry & Biodiversity 4 (8): 1678-1692), for example reducing growth and invasiveness of aggressive human breast cancer cells (McAllister et al., 2007, Mol. Cancer Ther. 6 (11): 2921-7) Recent studies have also shown CBD to be as effective as an atypical antipsychotic for treating schizophrenia (Zuardi et al., 2006, Braz. J. Med. Biol. Res. 39 (4): 421-429), and studies also suggests that CBD may relieve symptoms of dystonia (Consroe, 1986, The International journal of neuroscience 30 (4): 277-282).

Cannabis produces cannabidiolic acid (CBDA) through the same metabolic pathway as THC, until the last step, where CBDA synthase performs catalysis instead of THCA synthase. See Marks et al. (2009) Journal of Experimental Botany 60 (13): 3715-3726.) and Meijer et al. I, II, III, and IV.

Non-limiting examples of CBD variants include CBD-C5, CBDM-C5, CBD-C4, CBDV-C3, CBD-C1, CBDA-C5, and CBDVA-C3.

Tetrahydrocannabinol (THC)

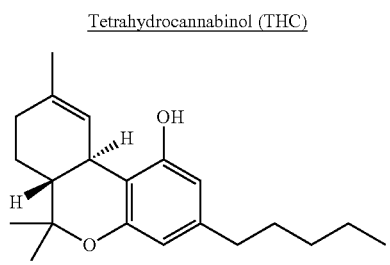 [SMILES: CCCCCc1cc(O)c2c(c1)OC(C)(C)[C@@H]1CCC(C)=C[C@@H]21]

Known as delta-9-tetrahydrocannabinol (Δ9-THC), THC is the principal psychoactive constituent (or cannabinoid) of the Cannabis plant. THC has mild to moderate analgesic effects, and Cannabis can be used to treat pain by altering transmitter release on dorsal root ganglion of the spinal cord and in the periaqueductal gray. Other effects include relaxation, alteration of visual, auditory, and olfactory senses, fatigue, and appetite stimulation. THC has marked antiemetic properties, and may also reduce aggression in certain subjects (Hoaken (2003) Addictive Behaviors 28: 1533-1554).

The pharmacological actions of THC result from its partial agonist activity at the cannabinoid receptor CB1, located mainly in the central nervous system, and the CB2 receptor, mainly expressed in cells of the immune system (Pertwee, (2006) International Journal of Obesity 30: S13-S18.) It is also suggested that THC has an anticholinesterase action, which may implicate it as a potential treatment for Alzheimer's and Myasthenia gravis (Eubanks et al., (2006) Molecular Pharmaceutics 3 (6): 773-7).

In the cannabis plant, THC occurs mainly as tetrahydrocannabinolic acid (THCA, 2-COOH-THC). Geranyl pyrophosphate and olivetolic acid react via an enzyme-catalyzed reaction to produce cannabigerolic acid, which is cyclized by the enzyme THC acid synthase to give THCA. Over time, or when heated, THCA is decarboxylated producing THC.

Non-limiting examples of THC variants include Δ9-THC-C5, Δ9-THC-C4, Δ9-THCV-C3, Δ9-THCO-C1, Δ9-THCA-C5 A, Δ9-THCA-C5 B, Δ9-THCA-C4 A, Δ9-THCA-C4 B, Δ9-THCVA-C3 A, Δ9-THCOA-C1 A, Δ9-THCOA-C1 B, Δ8-THC-C5, Δ8-THCA-C5 A, (−)-cis-Δ9-THC-C5.

Tetrahydrocannabivarin (THCV)

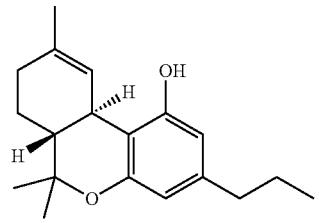

THCV is a propyl analogue of tetrahydrocannabinol. Although THCV possesses an almost identical structure to Δ9-THC (varying only by the length of its lipophilic alkyl chain), it has different molecular targets and pharmacological profile. Compared to THC which demonstrates its effects through weak partial agonist activity of both endocannabinoid receptors Cannabinoid-1 (CB1R) and Cannabinoid-2 (CB2R), THCV acts as a CB1 antagonist and a partial agonist of CB2. THCV has been reported to activate 5HT1A receptors to produce an antipsychotic effect that has therapeutic potential for ameliorating some of the negative, cognitive and positive symptoms of schizophrenia (Br J Pharmacol. 2015 March; 172(5): 1305-1318.) THCV has also shown antiepileptiform and anticonvulsant properties that suggest possible therapeutic application in the treatment of pathophysiologic hyperexcitability states such as untreatable epilepsy (Epilepsia. 2010 August; 51(8):1522-32).

Cannabidiolic Acid (CBDA)

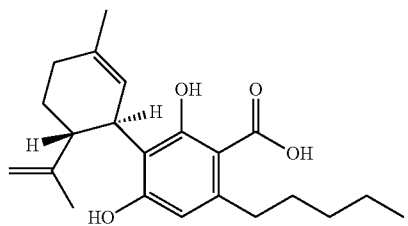

CBDA is most abundant in the glandular trichromes on Cannabis buds. CBDA is the chemical precursor to CBD. CBDA has been shown to exert therapeutic effects, including antiemetic, anti-inflammatory, anxiolytic, and antidepressant effects. (Behav Pharmacol. 2020 September; 31(6):591-596.) An in vivo rodent study showed that CBDA reduces thermal pain sensitivity in a model of Rett syndrome. (Neuroscience. 2021 Jan. 15; 453, 113-123.)

Cannabidivarin (CBDV)

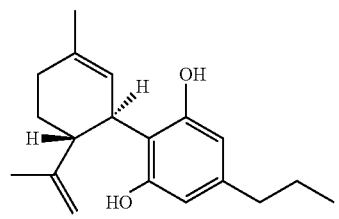

CBDV is a non-psychoactive cannabinoid found in Cannabis. It is a homolog of CBD with the side-chain shortened by two methylene bridges (CH$_2$ units). CBDV has demonstrated anticonvulsant activity in animal models and in human clinical trials. (Br J Pharmacol. 2013 October; 170 (3):679-92.) CBDV also acts as a functional partial agonist on dopamine D2-like receptors in vivo, supporting its therapeutic use in neurological disorders. (Biochemical and Biophysical Research Communications. 2020; 533(4):1366-1370).

Tetrahydrocannabinolic Acid (THCA)

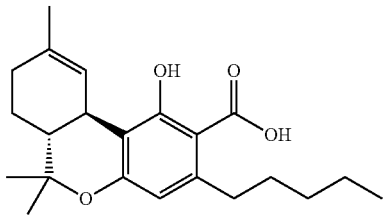

THCA is found in variable quantities in fresh, undried *Cannabis*, but is progressively decarboxylated to THC with drying and heating. THCA is produced from cannabigerolic acid by THCA synthase. THCA has been shown to have anti-inflammatory properties. (Biol Pharm Bull. 2011; 34(5): 774-8).

Cannabigerol (CBG)

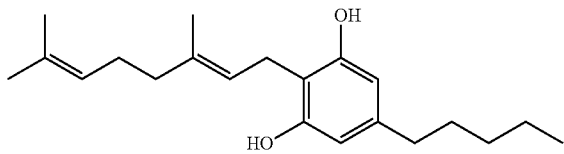

CBG is a non-psychoactive cannabinoid found in the *Cannabis* plants. CBG has been found to act as a high affinity α2-adrenergic receptor agonist, moderate affinity 5-HT1A receptor antagonist, and low affinity CB1 receptor antagonist. It also binds to the CB2 receptor. Cannabigerol has also been shown to reduce depression in animal models (US Patent Application Publication No. 2008-0031977). In particular, CBG has been shown to have significant potential applications in the treatment of glaucoma, depression, Huntington's disease, MRSA, cachexia, and cancer (Craig et al. 1984, Experimental eye research 39 (3):251-259; U.S. Pat. No. 8,481,085; Valdeolivas et al. 2015, Neurotherapeutics January 12(1):185-99; Appendino G et al., 2008, J. Nat Prod. August: 71(8):1427-30; Borrelli F et al. 2013, Biochem Pharmacol May 1:85(9):1306-16; Borrelli F. et al. 2014, Carcinogenesis December: 35(12):2787-97) Non-limiting examples of CBG variants include (E)-CBG-C5, (E)-CBGM-C5 A, (Z)-CBGA-C5 A, (E)-CBGV-C3, (E)-CBGA-C5 A, (E)-CBGAM-C5 A, and (E)-CBGVA-C3 A.

Cannabigerolic Acid (CBGA)

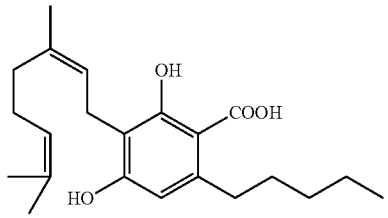

CBGA is the acidic form of CBG. CBGA is synthesized from olivetolic acid and geranyl diphosphate. CBGA is a precursor to THCA, CBDA, and CBCA. CBGA has been found to inhibit aldose reductase activity, suggesting that it may have therapeutic value for treatment of complications of diabetes. (Fitoterapia. 2018 June; 127:101-108).

Cannabinol (CBN)

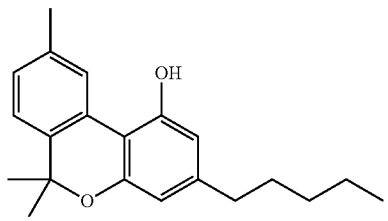

CBN is a mildly psychoactive cannabinoid found in trace amounts in *Cannabis*. CBN is a metabolite of THC. CBN has been shown to have significant applications in the treatment of anxiety disorder, insomnia, inflammation, convulsions, and bacterial infections. (Herring et al. Journal of Pharmacology and Experimental Therapeutics December 1999, 291 (3) 1156-1163.) CBN may be produced by aromatizing THC.

Cannabinolic Acid (CBNA)

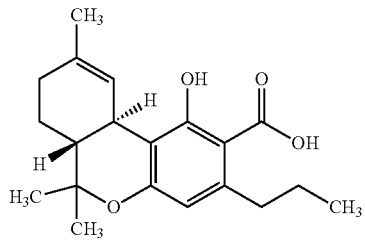

CBNA is found in trace amounts in *Cannabis*. CBNA is produced from THCA after exposure to ultraviolet light. CBNA has therapeutic benefit for treatment of insomnia, convulsions, and chronic pain.

Cannabidivarinic Acid (CBDVA)

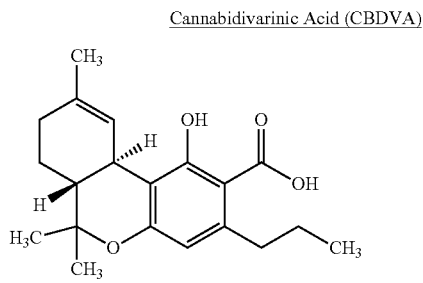 [SMILES: CCCc1cc2c(c(O)c1C(=O)O)[C@@H]1C=C(C)CC[C@H]1C(C)(C)O2]

CBDVA is the acidic form of CBDV. Extracts containing CBDVA exhibit antioxidant and antimicrobial activity against methicillin-resistant strains of *Staphylococcus aureus*. (Phytother Res. 2021 February; 35(2):1099-1112).

Cannabichromenic Acid (CBCA)

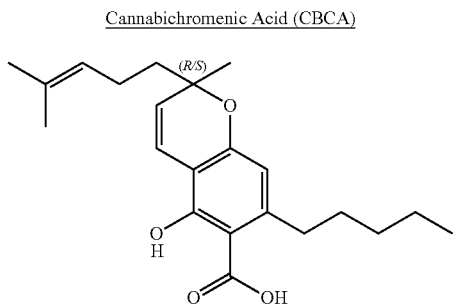

CBCA is the acidic form of CBC. CBCA is produced from CBGA. Geranyl pyrophosphate and olivetolic acid combine to produce CBGA, which is cyclized by the enzyme CBCA synthase to form CBCA. In vitro studies show that CBCA has more potent bactericidal activity than vancomycin, the currently recommended treatment for methicillin-resistant *Staphylococcus aureus* infections. (Antibiotics 2020, 9(8), 523).

Cannabichromene (CBC)

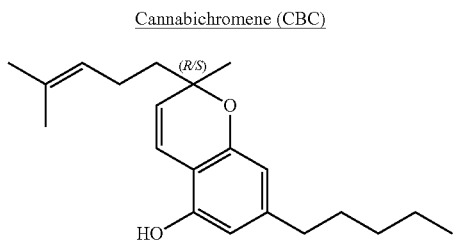 [SMILES: CCCCCc1cc(O)c2c(c1)OC(C)(CCC=C(C)C)C=C2]

CBC is produced from decarboxylation of CBCA. CBC is an agonist of TRPA1 and less potently an agonist of TRPV3 and TRPV4. CBC inhibits nitric oxide production in macrophages and ameliorates murine colitis. (Br J Pharmacol. 2013 May; 169(1): 213-229; Acta Physiol (Oxf). 2012 February; 204(2):255-66).

IIB. Additional Components of *Cannabis*

In addition to cannabinoids, *Cannabis* also comprises non-specific lipid-soluble material or "ballast" e.g. waxes, wax esters and glycerides, unsaturated fatty acid residues, terpenes, chlorophyll, carotenes, flavonoids, pigments, sugars, cellulose compounds, and minerals.

*Cannabis* produces over 120 different terpenes (Russo (2011) British Journal of Pharmacology, 163:1344-1364).

Within the context and verbiage of this document the terms 'terpenoid' and 'terpene' are used interchangeably. In some embodiments, the present disclosure provides compositions comprising one or more terpenes or terpenoids.

In addition to many circulatory and muscular effects, some terpenes interact with neurological receptors. A few terpenes produced by *cannabis* plants also bind weakly to cannabinoid receptors. Some terpenes can alter the permeability of cell membranes and allow in either more or less THC, while other terpenes can affect serotonin and dopamine chemistry as neurotransmitters. Terpenoids are lipophilic, and can interact with lipid membranes, ion channels, a variety of different receptors (including both G-protein coupled odorant and neurotransmitter receptors), and enzymes. Some are capable of absorption through human skin and passing the blood brain barrier.

Terpenoids are mainly synthesized in two metabolic pathways: mevalonic acid pathway (a.k.a. HMG-CoA reductase pathway, which takes place in the cytosol) and MEP/DOXP pathway (a.k.a. The 2-C-methyl-D-erythritol 4-phosphate/1-deoxy-D-xylulose 5-phosphate pathway, non-mevalonate pathway, or mevalonic acid-independent pathway, which takes place in plastids). Geranyl pyrophosphate (GPP), which is used by *cannabis* plants to produce cannabinoids, is formed by condensation of dimethylallyl pyrophosphate (DMAPP) and isopentenyl pyrophosphate (IPP) via the catalysis of GPP synthase. Alternatively, DMAPP and IPP are ligated by FPP synthase to produce farnesyl pyrophosphate (FPP), which can be used to produce sesquiterpenoids. Geranyl pyrophosphate (GPP) can also be converted into monoterpenoids by limonene synthase.

Terpenes are derived biosynthetically from units of isoprene, which have the molecular formula $C_5H_8$. The basic molecular formulae of terpenes are multiples of $(C_5H_8)_n$ where n is the number of linked isoprene units. The isoprene units may be linked together "head to tail" to form linear chains or they may be arranged to form rings.

Within the context of this disclosure, the term "terpene" includes Hemiterpenes, Monoterpenols, Terpene esters, Diterpenes, Monoterpenes, Polyterpenes, Triterpenes, Tetraterpenes, Terpenoid oxides, Sesterterpenes, Sesquiterpenes, Norisoprenoids, as well as their isomers, enantiomers, or derivatives. Within the context of this disclosure, the term terpene includes the α-(alpha), β-(beta), γ-(gamma), oxo-, isomers, or any combinations thereof.

In some embodiments, the present disclosure teaches separating a selected cannabinoid from a solution comprising terpenes. Non-limiting examples of terpenes include: Alpha Pinene, Limonene, Beta Pinene, Alpha Phellandrene, Terpinolene, Nerolidol, Nerol, Myrcene, Beta Caryophyllene, 7,8-dihydro-alpha-ionone, 7,8-dihydro-beta-ionone, Acetanisole, Acetic Acid, Acetyl Cedrene, Anethole, Anisole, Benzaldehyde, Bergamotene (Alpha-cis-Bergamotene) (Alpha-trans-Bergamotene), Bisabolol (Beta-Bisabolol), Alpha Bisabolol, Borneol, Bornyl Acetate, Butanoic/Butyric Acid, Cadinene (Alpha-Cadinene) (Gamma-Cadinene), Cafestol, Caffeic acid, Camphene, Camphor, Capsaicin, Carene (Delta-3-Carene), Carotene, Carvacrol, Dextro-Carvone, Laevo-Carvone, Alpha-Caryophyllene, Beta-Caryophyllene, Caryophyllene oxide, Cedrene (Alpha-Cedrene) (Beta-Cedrene), Cedrene Epoxide (Alpha-Cedrene Epoxide), Cedrol, Cembrene, Chlorogenic Acid, Cinnamaldehyde, Alpha-amyl-Cinnamaldehyde, Alpha-hexyl-Cinnamaldehyde, Cinnamic Acid, Cinnamyl Alcohol, Citronellal, Citronellol, Cryptone, Curcumene (Alpha-Curcumene) (Gamma-Curcumene), Decanal, Dehydrovomifoliol, Diallyl Disulfide, Dihydroactinidiolide, Dimethyl Disulfide, Eicosane/Icosane, Elemene (Beta-Elemene), Estragole, Ethyl acetate, Ethyl Cinnamate, Ethyl maltol, Eucalyptol/1, 8-Cineole, Eudesmol (Alpha-Eudesmol) (Beta-Eudesmol) (Gamma-Eudesmol), Eugenol, Euphol, Farnesene, Farnesol, Fenchol (Beta-Fenchol), Fenchone, Geraniol, Geranyl acetate, Germacrenes, Germacrene B, Guaia-1(10),11-diene, Guaiacol, Guaiene (Alpha-Guaiene), Gurjunene (Alpha-Gurjunene), Herniarin, Hexanaldehyde, Hexanoic Acid, Humulene (Alpha-Humulene) (Beta-Humulene), Ionol (3-oxo-alpha-ionol) (Beta-Ionol), Ionone (Alpha-Ionone) (Beta-Ionone), Ipsdienol, Isoamyl Acetate, Isoamyl Alcohol, Isoamyl Formate, Isoborneol, Isomyrcenol, Isopulegol, Isovaleric Acid, Isoprene, Kahweol, Lavandulol, Limonene, Gamma-Linolenic Acid, Linalool, Longifolene, Alpha-Longipinene, Lycopene, Menthol, Methyl butyrate, 3-Mercapto-2-Methylpentanal, Mercaptan/Thiols, Beta-Mercaptoethanol, Mercaptoacetic Acid, Allyl Mercaptan, Benzyl Mercaptan, Butyl Mercaptan, Ethyl Mercaptan, Methyl Mercaptan, Furfuryl Mercaptan, Ethylene Mercaptan, Propyl Mercaptan, Thenyl Mercaptan, Methyl Salicylate, Methylbutenol, Methyl-2-Methylvalerate, Methyl Thiobutyrate, Myrcene (Beta-Myrcene), Gamma-Muurolene, Nepetalactone, Nerol, Nerolidol, Neryl acetate, Nonanaldehyde, Nonanoic Acid, Ocimene, Octanal, Octanoic Acid, P-Cymene, Pentyl butyrate, Phellandrene, Phenylacetaldehyde, Phenylethanethiol, Phenylacetic Acid, Phytol, Pinene, Beta-Pinene, Propanethiol, Pristimerin, Pulegone, Quercetin, Retinol, Rutin, Sabinene, Sabinene Hydrate, cis-Sabinene Hydrate, trans-Sabinene Hydrate, Safranal, Alpha-Selinene, Alpha-Sinensal, Beta-Sinensal, Beta-Sitosterol, Squalene, Taxadiene, Terpin hydrate, Terpineol, Terpine-4-ol, Alpha-Terpinene, Gamma-Terpinene, Terpinolene, Thiophenol, Thujone, Thymol, Alpha-Tocopherol, Tonka Undecanone, Undecanal, Valeraldehyde/Pentanal, Verdoxan, Alpha-Ylangene, Umbelliferone, and Vanillin.

In some embodiments, the methods of the disclosure comprise separating a selected cannabinoid from a derivative of a terpene. Derivatives of terpenes include terpenoids, hemiterpenoids, monoterpenoids, sesquiterpenoids, sesterterpenoid, sesquarterpenoids, tetraterpenoids, triterpenoids, tetraterpenoids, polyterpenoids, isoprenoids, and steroids. Terpenoids, a.k.a. isoprenoids, are a large and diverse class of naturally occurring organic chemicals similar to terpenes, derived from five-carbon isoprene units assembled and modified in thousands of ways. Non-limiting examples of terpenoids include, Hemiterpenoids, 1 isoprene unit (5 carbons); Monoterpenoids, 2 isoprene units (10 C); Sesquiterpenoids, 3 isoprene units (15 C); Diterpenoids, 4 isoprene units (20 C) (e.g. ginkgolides); Sesterterpenoids, 5 isoprene units (25 C); Triterpenoids, 6 isoprene units (30 C) (e.g. sterols); Tetraterpenoids, 8 isoprene units (40 C) (e.g. carotenoids); and Polyterpenoid with a larger number of isoprene units.

In some embodiments, the methods of the disclosure comprise selectively crystallizing and/or purifying a selected cannabinoid from a solution comprising any of the aforementioned additional components of *Cannabis*.

III. Methods of Selectively Crystallizing and/or Purifying a Selected Cannabinoid from a Cannabinoid Solution In some embodiments, provided herein are methods of selectively crystallizing and/or purifying a selected cannabinoid from a cannabinoid solution. In some embodiments, the solution comprises a plurality of cannabinoids. In some embodiments, the selected cannabinoid is the only cannabinoid in the solution.

In some embodiments, the methods of the disclosure comprise crystallizing or extracting and/or purifying a selected cannabinoid from a solution containing a plurality of cannabinoids. In some embodiments, the solution containing a plurality of cannabinoids refers to a solution containing two or more cannabinoids. For example, the solution containing a plurality of cannabinoids may contain at least two, at least three, at least four, at least five, at least six, at least seven, at least eight, at least nine, at least ten, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 cannabinoids, or any value or range therebetween, including endpoints. The solution containing a plurality of cannabinoids may contain any of the cannabinoids described herein, for example, those described in Section IIA of this disclosure. In some embodiments, the selected cannabinoid is selected from the group consisting of CBD, THC, THCV, CBDA, CBDV, THCA, CBG, CBN, CBNA, CBDVA, CBCA, and CBC.

The solution containing a plurality of cannabinoids may be a *Cannabis* oil. As used herein the term "*Cannabis* oil," which is used interchangeably herein with "Hemp oil," refers to a composition produced by extracting cannabinoids from a *Cannabis* plant or *Cannabis* plant part(s). In some embodiments, the *Cannabis* oil is a primary cannabinoid extract (also referred to as a "primary *cannabis* extract"). In some embodiments, the primary cannabinoid extract is substantially free of any exogenous solvent. That is, in some embodiments, the *cannabis* oil/primary cannabinoid extract comprises less than 5%, 4%, 3%, 2%, 1%, 0.5%, 0.3%, 0.2%, or 0.1% of an exogenous solvent. In some embodiments, the primary cannabinoid extract is the chemical constituents of *Cannabis* (e.g., cannabinoids and terpenes) suspended in MCT derived from the *Cannabis* plant. In some embodiments, the primary *cannabis* extract is a CO2 extraction or an alcohol extraction of a *cannabis* plant. In some embodiments, the primary *cannabis* extract is a CO2 extraction or an alcohol extraction of a cannabinoid-producing microorganism culture.

In some embodiments, a "selected cannabinoid" is present in the solution containing a plurality of cannabinoids at a concentration greater than or equal to its supersaturation point. The term "supersaturation point" is the point at which the cannabinoid's amount in solution (e.g., concentration) exceeds its solubility at a given temperature. In some embodiments, the supersaturation point of the selected cannabinoid is greater than or equal to 20%, 25%, 30%, 40%, or 50% by weight of the solution. For example, the supersaturation point of the selected cannabinoid is greater than or equal to 55%, greater than or equal to 60%, greater than or equal to 65%, greater than or equal to 70%, greater than or equal to 75%, greater than or equal to 80%, greater than or equal to 85%, greater than or equal to 90%, or greater than or equal to 95% by weight of the solution. In some embodiments, the supersaturation point of the selected cannabinoid is from about 50% and about 70% by weight of the solution. For example, the supersaturation point of the selected cannabinoid is about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, or about 70% by weight of the solution, including all values and subranges in between inclusive of endpoints. In some embodiments, the supersaturation point of the selected cannabinoid is between about 50% and about 60% by weight of the solution. In some embodiments, the supersaturation point of the selected cannabinoid is between about 60% and about 70% by weight of the solution.

In some embodiments, the selected cannabinoid is present at a minimum concentration in the solution containing a plurality of cannabinoids or in a solution in which the selected cannabinoid is the only cannabinoid. The term "minimum concentration" refers to the lowest concentration of cannabinoid required for selective crystallization of the cannabinoid.

In some embodiments, the minimum concentration of a selected cannabinoid in a solution is from 1% to 90% by weight of the solution. For example, the minimum concentration of a selected cannabinoid in a solution is about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, or about 90% by weight of the solution. In some embodiments, the minimum concentration of a selected cannabinoid in a solution is from 5% to 30% by weight of the solution. In some embodiments, the minimum concentration of a selected cannabinoid in a solution containing a plurality of cannabinoids is from 10% to 75%. In some embodiments, the minimum concentration of a selected cannabinoid in a solution is about 5% by weight of the solution. In some embodiments, the minimum concentration of a selected cannabinoid is about 10% by weight of the solution. In some embodiments, the minimum concentration of a selected cannabinoid in a solution is about 25% by weight of the solution. In some embodiments, the minimum concentration of a selected cannabinoid in a solution is about 19.6% by weight of the solution.

In some embodiments, the selected cannabinoid is the highest concentration cannabinoid in the solution containing a plurality of cannabinoids. For example, CBD is the selected cannabinoid in a solution comprising 70% w/w CBD, 5% w/w CBN, and 2% w/w THC.

In some embodiments, the selected cannabinoid is present in the solution at a concentration from about 0.5% to about 99% by weight of the solution. For example, the selected cannabinoid may be present at a concentration of about 0.5%, about 0.6%, about 0.7%, about 0.8%, about 0.9%, about 1%, about 1.5%, about 2%, about 2.5%, about 3%, about 3.5%, about 4%, about 4.5%, about 5%, about 5.5%, about 6%, about 6.5%, about 7%, about 7.5%, about 8%, about 8.5%, about 9%, about 9.5%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, or about 70%, about 75%, about 80%, about 85%, about 90%, about 95%, about 96%, about 97%, about 98%, or about 99% by weight of the solution, including all subranges and ranges therebetween. In some embodiments, the selected cannabinoid is present at a concentration of at least about 0.5%, at least about 0.6%, at least about 0.7%, at least about 0.8%, at least about 0.9%, at least about 1%, at least about 1.5%, at least about 2%, at least about 2.5%, at least about 3%, at least about 3.5%, at least about 4%, at least about 4.5%, at least about 5%, at least about 5.5%, at least about 6%, at least about 6.5%, at least about 7%, at least about 7.5%, at least about 8%, at least about 8.5%, at least about 9%, at least about 9.5%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25%, at least about 26%, at least about 27%, at least about 28%, at least about 29%, at least about 30%, at least about 31%, at least about 32%, at least about 33%, at least about 34%, at least about 35%, at least about 36%, at least about 37%, at least about 38%, at least about 39%, at least about 40%, at least about 41%, at least about 42%, at least about 43%, at least about 44%, at least about 45%, at least about 46%, at least about 47%, at least about 48%, at least about 49%, at least about 50%, at least about 51%, at least about 52%, at least about 53%, at least about 54%, at least about 55%, at least about 56%, at least about 57%, at least about 58%, at least about 59%, at least about 60%, at least about 61%, at least about 62%, at least about 63%, at least about 64%, at least about 65%, at least about 66%, at least about 67%, at least about 68%, at least about 69%, or at least about 70%, at least about 75%, at least about 80%, at least about 85%, at least about 90%, at least about 95%, at least about 96%, at least about 97%, at least about 98%, or at least about 99% by weight of the solution, including all ranges and subranges therebetween. In some embodiments, the selected cannabinoid is present in the solution at a concentration from about 0.5% to about 10% by weight of the solution. In some embodiments, the selected cannabinoid is present in the solution at a concentration between about 10% and about 70% by weight of the solution. In some embodiments, the selected cannabinoid is present in the solution at a concentration between about 10% and about 50% by weight of the solution. In some embodiments, the selected cannabinoid is present in the solution at a concentration from about 50% to about 70% by weight of the solution. In some embodiments, the selected cannabinoid is present in the solution at a concentration of at least 10% by weight of the solution. In some embodiments, the selected cannabinoid is present in the solution at a concentration of at least 50% by weight of the solution. In some embodiments, the selected cannabinoid is present in the solution containing a plurality of cannabinoids at a concentration of at least 60% by weight of the solution. In some embodiments, the selected cannabinoid is present in the solution at a concentration of at least about 70% by weight of the solution.

In some embodiments, the selected cannabinoid is soluble in the solution (e.g., a primary cannabinoid extract) when the Hildebrand solubility parameter of the selected cannabinoid is less than 5.1 MPa$^{1/2}$ of the Hildebrand solubility parameter of the solvent (e.g., MCT). In some embodiments, the selected cannabinoid is soluble in the primary cannabinoid extract when it is heated to a temperature between 50° C. and about 79° C., and insoluble in the primary cannabinoid extract at temperatures less than 50° C. The Hildebrand solubility parameters for exemplary compounds present in *Cannabis* are provided in Table 1. The Hildebrand solubility parameters are described in detail in Hansen, Charles M, Hansen Solubility Parameters, A User's Handbook, CRC Press, 2000, which is incorporated by reference herein in its entirety.

TABLE 1

Hildebrand Solubility Parameters for Cannabinoids and Terpenes

| Compound | Solubility Parameter (MPa$^{1/2}$) |
| --- | --- |
| THC | 22.09 |
| CBD | 24.34 |
| THCA | 24.14 |
| CBDA | 25.77 |
| Beta-myrcene | 21.46 |
| Beta-sitosterol | 3.86 |
| Limonene | 16.90 |
| Alpha-pinene | 16.16 |
| p-cymene | 16.57 |
| Beta-caryophyllene | 21.41 |
| D-limonene | 24.46 |
| Pulegone | 25.65 |
| 1,8-cineole | 18.96 |
| alpha-terpineol | 17.10 |
| Terpineol-4-ol | 18.21 |
| Apigenin | 20.80 |
| Quercetin | 25.89 |
| Cannflavin A | 10.35 |

In some embodiments, the solution comprises non-specific lipid-soluble material or "ballast" e.g. waxes, wax esters and glycerides, unsaturated fatty acid residues, terpenes, carotenes, chlorophyll, flavonoids, pigments, sugars, cellulose compounds, and minerals.

In some embodiments, the solution is a *Cannabis* oil that does not contain any cutting agents. Examples of cutting agents include polyethylene glycol and glycerin.

In some embodiments, the solution comprises an organic non-polar solvent. In some embodiments, the organic non-polar solvent is oleic acid, olive oil, coconut oil, canola oil, flaxseed oil, avocado oil, sesame oil, canola oil, palm oil, safflower oil, soybean oil, corn oil, peanut oil, walnut oil, flaxseed oil, sunflower oil, palm oil, palm kernel oil, caproic acid, caprylic acid, hempseed oil, walnut oil, or medium-chain triglyceride (MCT) oil.

In some embodiments, the methods of the disclosure, (e.g., the methods of Sections IIIA and IIIB) do not use toxic solvents, such as pentane, hexane, ethanol, ether, isopropanol, propane, or butane. In some embodiments, the methods of the disclosure are zero waste processes.

IIIA. Method of Selectively Crystallizing a Selected Cannabinoid from a Solution In some embodiments, provided herein is a method of crystallizing a selected cannabinoid from a cannabinoid solution, comprising: (a) providing a solution containing a substantially dissolved selected cannabinoid comprising microbubbles or dissolved air; and (b) exposing the dissolved cannabinoid solution of step (a) to a vacuum for a time period sufficient to crystallize the selected cannabinoid. In some embodiments, the solution containing a substantially dissolved cannabinoid is produced by increasing the temperature of the cannabinoid solution until the selected cannabinoid is substantially dissolved in the solution. In some embodiments, the vacuum is greater than about −5 inHg, about −10 inHg, about −15 inHg, about −20 inHg, or about −25 inHg. Without being bound by theory, exposure of the cannabinoid solution to a vacuum allows microbubbles or dissolved air to expand, facilitating nucleation of crystals of the selected cannabinoid. FIG. 17A shows expansion of microbubbles after exposure to a vacuum.

In some embodiments, provided herein is a method of crystallizing a selected cannabinoid from a cannabinoid solution, comprising: (a) providing a solution containing a substantially dissolved selected cannabinoid; and (b) exposing the dissolved cannabinoid solution of step (a) to a (e.g., one or more) nucleation factor(s) for a time period sufficient to crystallize the selected cannabinoid, wherein the nucleation factor is selected from the group consisting of vacuum, cold shock, introducing a crystal of the selected cannabinoid into the dissolved cannabinoid solution (seed crystal), mechanically agitating the dissolved cannabinoid solution, and combinations thereof. In some embodiments, the solution containing a substantially dissolved cannabinoid is produced by increasing the temperature of the cannabinoid solution until the selected cannabinoid is substantially dissolved in the solution. In some embodiments, vacuum is one of the nucleation factors, and other nucleation factors precede the vacuum.

In some embodiments, provided herein is a method of crystallizing a selected cannabinoid from a cannabinoid solution, comprising: (a) providing a cannabinoid solution containing a substantially dissolved selected cannabinoid, wherein the selected cannabinoid is present in the solution at a concentration greater than or equal to its supersaturation point, and wherein the selected cannabinoid is the highest concentration cannabinoid in the solution, and wherein said solution is substantially free of any exogenous solvent; and (b) exposing the cannabinoid solution of step (a) to nucleation factors comprising mechanical agitation followed by a vacuum for a time period sufficient to crystallize the selected cannabinoid. In some embodiments, the solution containing a substantially dissolved cannabinoid is produced by increasing the temperature of the cannabinoid solution until the selected cannabinoid is substantially dissolved in the solution. In some embodiments, the vacuum is greater than about −5 inHg, about −10 inHg, about −15 inHg, about −20 inHg, or about −25 inHg. Without being bound by theory, exposure of the cannabinoid solution to agitation allows microbubbles to form in the cannabinoid solution and exposure of the solution to a vacuum allows the microbubbles to expand, facilitating nucleation of crystals of the selected cannabinoid.

In some embodiments, provided herein is a method of selectively crystallizing a selected cannabinoid from a solution of cannabinoids, comprising the steps of: (a) providing a solution containing a plurality of cannabinoids, wherein the selected cannabinoid is present in the solution at a concentration greater than or equal to its supersaturation point, and wherein the selected cannabinoid is the highest concentration cannabinoid in the solution; (b) increasing the temperature of the solution until the selected cannabinoid is substantially dissolved in the solution; and (c) decreasing the temperature of the solution to about −5° C. or lower to produce a cooled solution wherein the selected cannabinoid crystallizes out of solution, thereby forming crystals of the selected cannabinoid. In some embodiments, the cooled solution is exposed to a vacuum.

In some embodiments, provided herein is a method of selectively crystallizing a selected cannabinoid from a solution of cannabinoids, comprising the steps of: (a) providing a solution containing a plurality of cannabinoids, wherein the selected cannabinoid is present in the solution at a concentration greater than or equal to 5%, 10%, 20%, or 30% by weight of the solution, (b) increasing the temperature of the solution until the selected cannabinoid is substantially dissolved in the solution; and (c) decreasing the temperature of the solution to about −5° C. or lower to produce a cooled solution wherein the selected cannabinoid crystallizes out of solution, thereby forming crystals of the selected cannabinoid. In some embodiments, the cooled solution is exposed to a vacuum. In some embodiments, the selected cannabinoid is present in the solution at a concentration of greater than or equal to 10% by weight of the solution.

In some embodiments, provided herein is a method of selectively crystallizing a selected cannabinoid from a solution of cannabinoids, comprising the steps of: (a) providing a solution containing a plurality of cannabinoids, (b) increasing the temperature of the solution until the selected cannabinoid is substantially dissolved in the solution; and (c) decreasing the temperature of the solution to about −5° C. or lower to produce a cooled solution wherein the selected cannabinoid crystallizes out of solution, thereby forming crystals of the selected cannabinoid, wherein the selected cannabinoid is present at a minimum concentration of between 10% by weight and 95% by weight of the solution. In some embodiments, the selected cannabinoid is present at a minimum concentration of about 10%, about 15%, or about 20%. In some embodiments, the cooled solution is exposed to a vacuum.

In some embodiments, provided herein is a method of crystallizating a selected cannabinoid from a solution in which the selected cannabinoid is the only cannabinoid in the solution, comprising the steps of (a) providing a solution containing the selected cannabinoid; (b) increasing the temperature of the solution until the selected cannabinoid is substantially dissolved in the solution; and (c) decreasing the temperature of the solution to about −5° C. or lower to produce a cooled solution wherein the selected cannabinoid crystallizes out of solution, thereby forming crystals of the selected cannabinoid. In some embodiments, the selected cannabinoid is present at a minimum concentration of between 5% and 95% by weight of the solution. In some embodiments, the selected cannabinoid is present at a minimum concentration of between 5 and 30% by weight of the solution.

Providing a Solution Containing a Substantially Dissolved Cannabinoid

In some embodiments, the method comprises providing a cannabinoid solution. In some embodiments, the solution contains a substantially dissolved cannabinoid. A cannabinoid that is substantially dissolved is at least 95% dissolved, at least 96% dissolved, at least 97% dissolved, at least 98% dissolved, at least 99% dissolved, or 100% dissolved. The amount of cannabinoid dissolved may be determined using methods known to a person of skill in the art. In some embodiments, the amount of cannabinoid dissolved is determined using a method selected from the group consisting of mass spectrometry, liquid chromatography, ultraviolet spectrophotometry, high performance liquid chromatography, ultraviolet-visible (UV-visible) absorption spectroscopy, and immunoassay. In some embodiments, a solution containing a substantially dissolved cannabinoid is clear (i.e., not opaque or occluded by crystals). In some embodiments, the amount of cannabinoid dissolved is determined using a turbidity measurement.

In some embodiments, temperature of the solution is increased until the selected cannabinoid is substantially dissolved in the solution. In some embodiments however, the cannabinoids are already dissolved, and the heating step can be omitted. Without being bound by theory, heating the solution breaks apart any existing cannabinoid crystals, to allow for the formation of crystals that are homogenous in lattice structure, which in turn aids in purification/separation of the selected cannabinoid.

In some embodiments, the temperature is increased to between about 50° C. and about 79° C., for example, about 50° C., about 51° C., about 52° C., about 53° C., about 54° C., about 55° C., about 56° C., about 57° C., about 58° C., about 59° C., about 60° C., about 61° C., about 62° C., about 63° C., about 64° C., about 65° C., about 66° C., about 67° C., about 68° C., about 69° C., about 70° C., about 71° C., about 72° C., about 73° C., about 74° C., about 75° C., about 76° C., about 77° C., about 78° C., or about 79° C., including all ranges and subranges therebetween. In some embodiments, the temperature is increased to at least about 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., or 80° C., including all ranges the subranges therebetween. In some embodiments, the temperature is increased to about 60° C. In some embodiments, the selected cannabinoid is CBD, THC, THCV, CBDA, CBDV, THCA, CBG, CBGA, CBNA, CBDVA, CBCA, or CBC, and the temperature is increased to about 60° C. In some embodiments, the temperature is increased to about 70° C. In some embodiments, the temperature is increased to about 70° C., and the selected cannabinoid is CBN or CBNA.

Persons having skill in the art will be aware of the consequences of overheating cannabinoid oils. For example, in some embodiments, heating a *cannabis* oil beyond 70° C., 71° C., 72° C., 73° C., 74° C., 75° C., 76° C., 77° C., 78° C., 79° C., or 80° C. for an extended period of time can cause breakdown of component ingredients that may give the oil and subsequent purified cannabinoids an undesirable color or taste. Therefore, in some embodiment, the cannabinoid oil is not heated beyond 70° C., 71° C., 72° C., 73° C., 74° C., 75° C., 76° C., 77° C., 78° C., 79° C., or 80° C. for more than 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 minutes.

In some embodiments, the temperature is increased by about 1° C. every minute, every 5 minutes, every 10 minutes, every 15 minutes, every 20 minutes, every 30 minutes, or every hour. In some embodiments, the temperature of the solution is increased by about 5° C. every minute, every 5 minutes, every 10 minutes, every 15 minutes, every 20 minutes, every 30 minutes, or every hour. In some embodiments, the temperature of the solution is increased by about 10° C. every minute, every 5 minutes, every 10 minutes, every 15 minutes, every 20 minutes, every 30 minutes, or every hour. In some embodiments, the temperature of the solution is increased by about 15° C. every minute, every 5 minutes, every 10 minutes, every 15 minutes, every 20 minutes, every 30 minutes, or every hour. In some embodiments, the temperature of the solution is increased by about 20° C. every minute, every 5 minutes, every 10 minutes, every 15 minutes, every 20 minutes, every 30 minutes, or every hour. In some embodiments, the temperature of the solution is increased by about 30° C. every minute, every 5 minutes, every 10 minutes, every 15 minutes, every 20 minutes, every 30 minutes, or every hour. In some embodiments, the temperature of the solution is increased by about 40° C. every minute, every 5 minutes, every 10 minutes, every 15 minutes, every 20 minutes, every 30 minutes, or every hour. In some embodiments, the temperature of the solution is increased by about 50° C. every minute, every 5 minutes, every 10 minutes, every 15 minutes, every 20 minutes, every 30 minutes, or every hour.

In some embodiments, the temperature is increased using a thermal cycler.

In some embodiments, the solution is stirred or mixed during heating.

The solution may comprise any of the features described in Section III of this disclosure. As used herein, the "selected cannabinoid" is the cannabinoid that is crystallized from the solution, such as a solution containing a plurality of cannabinoids or a solution in which the cannabinoid is the only cannabinoid in the solution. In some embodiments, the selected cannabinoid is selected from the group consisting of cannabidiol (CBD), tetrahydrocannabinol (THC), tetrahydrocannabivarin (THCV), cannabidiolic acid (CBDA), cannabigerolic acid (CBGA), cannabidivarin (CBDV), tetrahydrocannabinolic acid (THCA), cannabigerol (CBG), cannabinol (CBN), cannabinolic acid (CBNA), cannabidivarinic acid (CBDVA), cannabichromenic acid (CBCA), and cannabichromene (CBC).

In some embodiments, the selected cannabinoid is present in the solution wherein at least one of the cannabinoids is at a concentration greater than or equal to its supersaturation point. Table 1 contains the supersaturation points of exemplary cannabinoids.

Exposure to Nucleation Factors

In some embodiments, a solution containing a substantially dissolved cannabinoid is exposed to one or more nucleation factors. A nucleation factor promotes nucleation of a crystal of the selected cannabinoid. In some embodiments, the methods of crystallizing cannabinoids described herein require application of 1, 2, 3, 4, 5, 6, or more nucleation factors. In some embodiments, the methods of crystallizing cannabinoids described herein require vacuum. In some embodiments, the methods of crystallizing cannabinoids described herein require vacuum and one other nucleation factor applied before the vacuum.

In some embodiments, the nucleation factor is selected from the group consisting of introducing a i) seed crystal (adding crystal of the selected cannabinoid into the solution containing a substantially dissolved selected cannabinoid), ii) vacuum (exposing the solution containing a substantially dissolved selected cannabinoid into a vacuum, usually applied as final nucleation factor), iii) agitation (e.g., mechanically agitating the solution containing a substantially dissolved selected cannabinoid), iv) moisture (increasing or maintaining the moisture content of the solution containing a substantially dissolved selected cannabinoid), v) aeration (aerating the solution containing a substantially dissolved selected cannabinoid), and combinations thereof. In some embodiments, the nucleation factor is selected from the group consisting of i) seed crystal (introducing a crystal of the selected cannabinoid into the solution containing a substantially dissolved selected cannabinoid), ii) vacuum (exposing the solution containing a substantially dissolved selected cannabinoid into a vacuum, usually as final nucleation factor), and iii) agitation (mechanically agitating the solution containing a substantially dissolved selected cannabinoid). In some embodiments, the nucleation factor is selected from the group consisting of increasing or maintaining the moisture content of the solution containing a substantially dissolved selected cannabinoid, aerating the solution containing a substantially dissolved selected cannabinoid, and combinations thereof.

In some embodiments, the method of selective crystallization described herein requires exposure of the solution containing a substantially dissolved selected cannabinoid to a vacuum.

In some embodiments, the method of selective crystallization described herein comprises exposing the solution containing a substantially dissolved selected cannabinoid to a vacuum followed by exposing the solution to one or more additional nucleation factors selected from the group consisting of: cold shock, introducing a crystal of the selected cannabinoid into the dissolved cannabinoid solution (seed crystal), mechanically agitating the dissolved cannabinoid solution, and combinations thereof. In some embodiments, the method of selective crystallization described herein comprises exposing the solution containing a substantially dissolved selected cannabinoid to one or more nucleation factors selected from the group consisting of: cold shock, introducing a crystal of the selected cannabinoid into the dissolved cannabinoid solution (seed crystal), mechanically agitating the dissolved cannabinoid solution, and combinations thereof before exposure of the solution to a vacuum.

In some embodiments, the method of selective crystallization requires (i) agitating the solution containing a substantially dissolved cannabinoid and (ii) exposing the solution containing a substantially dissolved selected cannabinoid to a vacuum. In some embodiments, step (i) is performed before step (ii). In some embodiments, step (ii) is performed before step (i). In some embodiments, step (i) and step (ii) are simultaneously performed (e.g., stir bar or sonicator in vacuum chamber).

In some embodiments, the method of selective crystallization comprises: (i) introducing the solution to the nucleation factors, cold shock, (i) mechanical agitation; (iii) introducing a crystal of the selected cannabinoid into the dissolved cannabinoid solution (seed crystal) and (iv) introducing the solution into a vacuum. In some embodiments, step (i) is performed before steps (ii)-(iv). In some embodiments, step (iii) is performed before step (ii) and step (iv) is done last. FIG. 17B shows the effect of cold shock and mechanical agitation. In some embodiments, these nucleation factors thicken the cannabinoid solution and result in bubble formation which aids cannabinoid nucleation.

In some embodiments, exposure of the solution containing a substantially dissolved selected cannabinoid to a nucleation factor increases the rate of crystallization of the selected cannabinoid by about 5% to about 400% compared to the same method that does not expose the solution containing a substantially dissolved selected cannabinoid to a nucleation factor. For example, exposure of the solution containing a substantially dissolved selected cannabinoid to a nucleation factor increases the rate of crystallization by about 5%, about 10%, about 20%, about 30%, about 40%, about 50%, about 60%, about 70%, about 80%, about 90%, about 100%, about 125%, about 150%, about 175%, about 200%, about 225%, about 250%, about 275%, about 300%, about 325%, about 350%, about 375%, or about 400% compared to the same method that does not expose the solution containing a substantially dissolved selected cannabinoid to a nucleation factor, including all values and subranges therebetween inclusive of endpoints. In some embodiments, increased rate of crystallization is measured by % of selected cannabinoid that is crystallized over time (e.g., the percentage of selected cannabinoid by weight or by moles of the solution per time, for example, per minute, per hour, or per day). In some embodiments, the increased rate of crystallization is measured by the total % of selected cannabinoid that crystallized at a given time, for example, at 5 minutes, at 10 minutes, at 15 minutes, at 20 minutes, at 25 minutes, at 30 minutes, at 35 minutes, at 40 minutes, at 45 minutes, at 50 minutes, about 55 minutes, at 1 hour, at 2 hours, at 3 hours, at 4 hours, at 5 hours, at 6 hours, at 7 hours, at 8 hours, at 9 hours, at 10 hours, at 11 hours, at 12 hours, at 13 hours, at 14 hours, at 15 hours, at 16 hours, at 17 hours, at 18 hours, at 19 hours, at 20 hours, about 21 hours, about 22 hours, about 23 hours, about 1 day, about 1.5 days, about 2 days, about 3 days, about 4 days, about 5 days, about 6 days, about 7 days, about 1 week, about 2 weeks, about 3 weeks, about 4 weeks, about 5 weeks, or about 1 month. In some embodiments, nucleation factors improve the quality of crystallization (e.g. providing more uniform crystal size, and/or smaller crystal size).

In some embodiments, exposure of the solution containing a substantially dissolved selected cannabinoid to a vacuum increases the rate of crystallization of the selected cannabinoid by about 5% to about 400% compared to the same method that does not expose the solution containing a substantially dissolved selected cannabinoid to a vacuum. For example, exposure of the solution containing a substantially dissolved selected cannabinoid to a vacuum increases the rate of crystallization by about 5%, about 10%, about 20%, about 30%, about 40%, about 50%, about 60%, about 70%, about 80%, about 90%, about 100%, about 125%, about 150%, about 175%, about 200%, about 225%, about 250%, about 275%, about 300%, about 325%, about 350%, about 375%, or about 400% compared to the same method that does not expose the solution containing a substantially dissolved selected cannabinoid to a vacuum, including all values and subranges therebetween inclusive of endpoints. In some embodiments, increased rate of crystallization is measured by % of selected cannabinoid that is crystallized over time (e.g., the percentage of selected cannabinoid by weight or by moles of the solution per time, for example, per minute, per hour, or per day). In some embodiments, the increased rate of crystallization is measured by the total % of selected cannabinoid that crystallized at a given time, for example, at 5 minutes, at 10 minutes, at 15 minutes, at 20 minutes, at 25 minutes, at 30 minutes, at 35 minutes, at 40 minutes, at 45 minutes, at 50 minutes, about 55 minutes, at 1 hour, at 2 hours, at 3 hours, at 4 hours, at 5 hours, at 6 hours, at 7 hours, at 8 hours, at 9 hours, at 10 hours, at 11 hours, at 12 hours, at 13 hours, at 14 hours, at 15 hours, at 16 hours, at 17 hours, at 18 hours, at 19 hours, at 20 hours, about 21 hours, about 22 hours, about 23 hours, about 1 day, about 1.5 days, about 2 days, about 3 days, about 4 days, about 5 days, about 6 days, about 7 days, about 1 week, about 2 weeks, about 3 weeks, about 4 weeks, about 5 weeks, or about 1 month. In some embodiments, exposure of the solution to a vacuum improves the quality of crystallization (e.g. providing more uniform crystal size, and/or smaller crystal size).

In some embodiments, exposure of the solution containing a substantially dissolved selected cannabinoid to a vacuum and mechanically agitating the solution increases the rate of crystallization of the selected cannabinoid by about 5% to about 400% compared to the same method that does not expose the solution containing a substantially dissolved selected cannabinoid to a vacuum and mechanically agitate the solution. For example, exposure of the solution containing a substantially dissolved selected cannabinoid to a vacuum and mechanical agitation of the solution increases the rate of crystallization by about 5%, about 10%, about 20%, about 30%, about 40%, about 50%, about 60%, about 70%, about 80%, about 90%, about 100%, about 125%, about 150%, about 175%, about 200%, about 225%, about 250%, about 275%, about 300%, about 325%, about 350%, about 375%, or about 400% compared to the same method that does not expose the solution containing a substantially dissolved selected cannabinoid to a vacuum and does not mechanically agitate the solution, including all values and subranges therebetween inclusive of endpoints. In some embodiments, increased rate of crystallization is measured by % of selected cannabinoid that is crystallized over time, (e.g., the percentage of selected cannabinoid by weight or by moles of the solution per time, for example, per minute, per hour, or per day). In some embodiments, the increased rate of crystallization is measured by the total % of selected cannabinoid that crystallized at a given time, for example, at 5 minutes, at 10 minutes, at 15 minutes, at 20 minutes, at 25 minutes, at 30 minutes, at 35 minutes, at 40 minutes, at 45 minutes, at 50 minutes, about 55 minutes, at 1 hour, at 2 hours, at 3 hours, at 4 hours, at 5 hours, at 6 hours, at 7 hours, at 8 hours, at 9 hours, at 10 hours, at 11 hours, at 12 hours, at 13 hours, at 14 hours, at 15 hours, at 16 hours, at 17 hours, at 18 hours, at 19 hours, at 20 hours, about 21 hours, about 22 hours, about 23 hours, about 1 day, about 1.5 days, about 2 days, about 3 days, about 4 days, about 5 days, about 6 days, about 7 days, about 1 week, about 2 weeks, about 3 weeks, about 4 weeks, about 5 weeks, or about 1 month. In some embodiments, exposure of the solution to a vacuum and mechanical agitation of the solution improves the quality of crystallization (e.g. providing more uniform crystal size, and/or smaller crystal size).

In some embodiments, exposure of the solution containing a substantially dissolved selected cannabinoid to a nucleation factor reduces the length of time required to crystallize 95% of the selected cannabinoid from the solution comprising a plurality of cannabinoids. In some embodiments, exposure of the solution containing a substantially dissolved selected cannabinoid to a nucleation factor reduces the time required to crystallize 95% of the selected cannabinoid by about 10%, about 20%, about 30%, about 40%, about 50%, about 60%, about 70%, about 80%, or about 90%, including all ranges and subranges therebetween, as compared to a solution containing a substantially dissolved selected cannabinoid that is not exposed to a nucleation factor.

The following paragraphs describe the aforementioned nucleation factors in more detail:

Nucleation Factor—Seed Crystal

In some embodiments, the nucleation factor comprises introducing a crystal of the selected cannabinoid into the solution containing a substantially dissolved selected cannabinoid, also referred to as a "seed crystal". For example, a CBD crystal may be added to a solution in which CBD is the selected cannabinoid. In some embodiments, the rate of crystallization of a selected cannabinoid from a solution containing a substantially dissolved selected cannabinoid comprising a seed crystal is higher than the rate of crystallization of the selected cannabinoid from a solution containing a substantially dissolved selected cannabinoid that does not contain a seed crystal. In some embodiments, the rate of crystallization of a selected cannabinoid from a solution containing a substantially dissolved selected cannabinoid comprising a seed crystal is about 5% to about 400% higher than the rate of crystallization of the selected cannabinoid from solution containing a substantially dissolved selected cannabinoid that does not contain a seed crystal. For example, the rate of crystallization of a selected cannabinoid from a solution containing a substantially dissolved selected cannabinoid comprising a seed crystal is about 5%, about 10%, about 20%, about 30%, about 40%, about 50%, about 60%, about 70%, about 80%, about 90%, about 100%, about 125%, about 150%, about 175%, about 200%, about 225%, about 250%, about 275%, about 300%, about 325%, about 350%, about 375%, or about 400% higher than the rate of crystallization of the selected cannabinoid from solution containing a substantially dissolved selected cannabinoid that does not contain a seed crystal, including all values and subranges therebetween, inclusive of endpoints.

Nucleation Factor—Mechanical Agitation

In some embodiments, the nucleation factor is mechanical agitation of the solution containing a substantially dissolved selected cannabinoid. Mechanical agitation may comprise any one of vibrating, shaking, stirring, sonicating, or mixing the solution. Without wishing to be bound by any one theory, the instant inventors believe that the mechanical agitation cavitates the solution, creating nucleation sites.

Nucleation Factor—Moisture Content

In some embodiments, the nucleation factor is increasing or maintaining the moisture content of the solution containing a substantially dissolved selected cannabinoid. In some embodiments, moisture is introduced to the solution containing a substantially dissolved selected cannabinoid. In some embodiments, moisture is introduced to the solution containing a substantially dissolved selected cannabinoid via a vacuum oven. In some embodiments, the nucleation factor is increasing or maintaining the humidity of the solution containing a substantially dissolved selected cannabinoid. In some embodiments, humidity is introduced to the solution containing a substantially dissolved selected cannabinoid. In some embodiments, humidity is introduced to the solution containing a substantially dissolved selected cannabinoid via a vacuum oven.

Nucleation Factor—Vacuum

In some embodiments, the nucleation factor is the introduction of the solution containing a substantially dissolved selected cannabinoid to a vacuum. In some embodiments, the pressure of the vacuum is between about −0.1 atm and about 0.25 atm. For example, the pressure of the vacuum is below about −0.1 atm, about −0.09 atm, about −0.08 atm, about −0.07 atm, about −0.06 atm, about −0.05 atm, about −0.04 atm, about −0.03 atm, about −0.02 atm, about −0.01 atm, 0 atm, about 0.01 atm, about 0.02 atm, about 0.03 atm, about 0.04 atm, about 0.05 atm, about 0.06 atm, about 0.07 atm, about 0.08 atm, about 0.09 atm, about 0.1 atm, about 0.15 atm, about 0.2 atm, or about 0.25 atm, including all subranges and values therebetween, inclusive of endpoints. In some embodiments, the pressure of the vacuum is between about 0.03 atm and about 0.06 atm. In some embodiments, the pressure of the vacuum is between about −0.03 atm and about −0.06 atm. In some embodiments, the pressure of the vacuum is less than about 1 μHg. In some embodiments, the pressure of the vacuum is between about −45 inHg and −5 inHg, for example, below about −45 inHg, about −40 inHg, about −35 inHg, about −30 inHg, about −25 inHg, about −20 inHg, about −15 inHg, about −10 inHg, or about −5 inHg. Unless otherwise stated or impossible unless below sea level, the pressures described herein are measured at an altitude of 5,280 feet.

In some embodiments, the vacuum nucleation factor is exposing the solution to less than 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, or 90% of sea level atmospheric pressure, including all ranges and subranges therebetween. In some embodiments, the vacuum nucleation factor is exposing the solution to at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% vacuum, including all ranges and subranges therebetween. In some embodiments, the vacuum is a vacuum oven. In some embodiments, the temperature of the vacuum oven is between 25° C. and about 125° C. For example, the temperature of the vacuum oven is about 25° C., about 30° C., about 35° C., about 40° C., about 45° C., about 50° C., about 55° C., about 60° C., about 65° C., about 70° C., about 75° C., about 80° C., about 85° C., about 90° C., about 90° C., about 95° C., about 100° C., about 105° C., about 110° C., about 115° C., about 120° C., or about 125° C., including all values and subranges therebetween inclusive of endpoints. In some embodiments, the temperature of the vacuum oven is about 33° C. In some embodiments, the temperature of the vacuum oven is about 34° C. In some embodiments, the temperature of the vacuum oven is about 35° C.

Nucleation Factor—Aeration

In some embodiments, the nucleation factor is aerating the solution containing a substantially dissolved selected cannabinoid. In some embodiments, aerating the solution containing a substantially dissolved selected cannabinoid comprises introducing a gas to the cooled solution. In some embodiments, carbon dioxide is introduced to the solution containing a substantially dissolved selected cannabinoid. Persons having skill in the art will be familiar with various techniques and devices for aerating solutions, including air flow below the surface of a liquid (e.g., via a tube or aeration stone).

Nucleation Factor—Cold Shock

In some embodiments, the nucleation factor comprises decreasing the temperature of the solution containing a substantially dissolved selected cannabinoid to about −5° C. or lower (referred to herein as "cold shock"). In some embodiments, cold shock comprises decreasing the temperature of the solution containing a substantially dissolved selected cannabinoid to a temperature between about −5° C. and about −20° C. For example, the temperature of the solution may be decreased to about −5° C., about −6° C., about −7° C., about −8° C., about −9° C., about −10° C., about −11° C., about −12° C., about −13° C., about −14° C., about −15° C., about −16° C., about −17° C., about −18° C., about −19° C., or about −20° C., including all values and subranges therebetween. In some embodiments, cold shock comprises decreasing the temperature of the solution to about −20° C.

In some embodiments, cold shock comprises reducing the temperature of the solution as quickly as possible. In some embodiments, cold shock only requires achieving a desired temperature, without regard to the speed of the temperature change. That is, in some embodiments, the cold shock treatment thickens the cannabinoid solution, thereby increasing the effectiveness of the agitation and or vacuum step. Thus, in some embodiments, the rate of cooling is only a matter of convenience.

In some embodiments, the temperature of the solution is decreased by about 1° C. every minute, every 5 minutes, every 10 minutes, every 15 minutes, every 20 minutes, every 30 minutes, or every hour. In some embodiments, the temperature of the solution is decreased by about 5° C. every minute, every 5 minutes, every 10 minutes, every 15 minutes, every 20 minutes, every 30 minutes, or every hour. In some embodiments, the temperature of the solution is decreased by about 10° C. every minute, every 5 minutes, every 10 minutes, every 15 minutes, every 20 minutes, every 30 minutes, or every hour. In some embodiments, the temperature of the solution is decreased by about 15° C. every minute, every 5 minutes, every 10 minutes, every 15 minutes, every 20 minutes, every 30 minutes, or every hour. In some embodiments, the temperature of the solution is decreased by about 20° C. every minute, every 5 minutes, every 10 minutes, every 15 minutes, every 20 minutes, every 30 minutes, or every hour. In some embodiments, the temperature of the solution is decreased by about 30° C. every minute, every 5 minutes, every 10 minutes, every 15 minutes, every 20 minutes, every 30 minutes, or every hour. In some embodiments, the temperature of the solution is decreased by about 40° C. every minute, every 5 minutes, every 10 minutes, every 15 minutes, every 20 minutes, every 30 minutes, or every hour. In some embodiments, the temperature of the solution is decreased by about 50° C. every minute, every 5 minutes, every 10 minutes, every 15 minutes, every 20 minutes, every 30 minutes, or every hour.

In some embodiments, the temperature of the solution containing the substantially dissolved cannabinoid is decreased to from about −5° C. and about −20° C. within about 2 hours. In some embodiments, the temperature is decreased to from about −5° C. and about −20° C. within about 15 minutes. In some embodiments, the solution containing the substantially dissolved selected cannabinoid is cold shocked and held at a temperature from about −5° C. to about −20° C. for from about 5 minutes to about 24 hours. For example, the temperature of the solution containing the substantially dissolved selected cannabinoid may be held at a temperature of about −5° C., about −6° C., about −7° C., about −8° C., about −9° C., about −10° C., about −11° C., about −12° C., about −13° C., about −14° C., about −15° C., about −16° C., about −17° C., about −18° C., about −19° C., or about −20° C., including all values and ranges therebetween, inclusive of endpoints, for about 5 minutes, about 10 minutes, about 15 minutes, about 20 minutes, about 25 minutes, about 30 minutes, about 35 minutes, about 40 minutes, about 45 minutes, about 50 minutes, about 55 minutes, about 60 minutes, about 1.5 hours, about 2 hours, about 2.5 hours, about 3 hours, about 3.5 hours, about 4 hours, about 4.5 hours, about 5 hours, about 5.5 hours, about 6 hours, about 6.5 hours, about 7 hours, about 7.5 hours, about 8 hours, about 8.5 hours, about 9 hours, about 9.5 hours, about 10 hours, about 10.5 hours, about 11 hours, about 11.5 hours, about 12 hours, about 12.5 hours, about 13 hours, about 13.5 hours, about 14 hours, about 14.5 hours, about 15 hours, about 15.5 hours, about 16 hours, about 16.5 hours, about 17 hours, about 17.5 hours, about 18 hours, about 18.5 hours, about 19 hours, about 19.5 hours, about 20 hours, about 20.5 hours, about 21 hours, about 21.5 hours, about 22 hours, about 22.5 hours, about 23 hours, about 23.5 hours, or about 24 hours, including all values and ranges therebetween, inclusive of endpoints. In embodiments, the temperature is held at about −20° C. for about 15 minutes.

Crystals of the Selected Cannabinoid

In some embodiments, the method separates cannabinoids by selectively crystalizing the selected cannabinoid. In some embodiments, the nucleation factors of the present disclosure trigger controlled crystallization that selectively crystallizes the selected cannabinoid while reducing the amount of contaminants in the lattice structure. In some embodiments, the crystals of the selected cannabinoid are between about 2 µm and about 5 µm in size, for example, about 2 µm, about 2.5 µm, about 3 µm, about 3.5 µm, about 4 µm, about 4.5 µm, or about 5 µm. In some embodiments, the crystals of the selected cannabinoid are greater than 2 µm in size, for example, about 2 µm, about 2.5 µm, about 3 µm, about 3.5 µm, about 4 µm, about 4.5 µm, about 5 µm, about 6 µm, about 7 µm, about 8 µm, about 9 µm, about 10 µm, about 11 µm, about 12 µm, about 13 µm, about 14 µm, about 15 µm, about 16 µm, about 17 µm, about 18 µm, about 19 µm, about 20 µm, about 21 µm, about 22 µm, about 23 µm, about 24 µm, about 25 µm, about 26 µm, about 27 µm, about 28 µm, about 29 µm, about 30 µm, or greater. As used herein, the term "size" may refer to a largest crystal's diameter or length. In some embodiments, the crystals of the selected cannabinoid are greater than or equal to about 5 µm, about 10 µm, about 15 µm, about 20 µm, about 25 µm, or about 30 µm in size. In some embodiments, the crystals of the selected cannabinoid are greater than or equal to about 25 µm in size, for example, 25 µm, about 26 µm, about 27 µm, about 28 µm, about 29 µm, about 30 µm, about 31 µm, about 32 µm, about 33 µm, about 34 µm, about 35 µm, or more. Thus, a rod-shaped crystal would have a particle size roughly equivalent to the length of the crystal. Crystal size may be measured using any one of the following techniques: x-ray scattering, small angle x-ray scattering, wide angle x-ray scattering, dynamic light scattering, analytical ultracentrifugation, size exclusion chromatography, and photon correlation spectroscopy.

In some embodiments, the method provides crystals of the selected cannabinoid that are at least 2 µm, 3 µm, 4 µm, 5 µm, 6 µm, 7 µm, 8 µm, 9 µm, 10 µm, 11 µm, 12 µm, 13 µm, 14 µm, 15 µm, 16 µm, 17 µm, 18 µm, 19 µm, 20 µm, 21 µm, 22 µm, 23 µm, 24 µm, 25 µm, 26 µm, 27 µm, 28 µm, 29 µm, 30 µm, 31 µm, 32 µm, 33 µm, 34 µm, 35 µm, 36 µm, 37 µm, 38 µm, 39 µm, 40 µm, 41 µm, 42 µm, 43 µm, 44 µm, 45 µm, 46 µm, 47 µm, 48 µm, 49 µm, 50 µm, 51 µm, 52 µm, 53 µm, 54 µm, 55 µm, 56 µm, 57 µm, 58 µm, 59 µm, 60 µm, 61 µm, 62 µm, 63 µm, 64 µm, 65 µm, 66 µm, 67 µm, 68 µm, 69 µm, 70 µm, 71 µm, 72 µm, 73 µm, 74 µm, 75 µm, 76 µm, 77 µm, 78 µm, 79 µm, 80 µm, or 81 µm in size, including all ranges and subranges therebetween. In some embodiments, the average crystal size of the selected cannabinoid are at least 2 µm, 3 µm, 4 µm, 5 µm, 6 µm, 7 µm, 8 µm, 9 µm, 10 µm, 11 µm, 12 µm, 13 µm, 14 µm, 15 µm, 16 µm, 17 µm, 18 µm, 19 µm, 20 µm, 21 µm, 22 µm, 23 µm, 24 µm, 25 µm, 26 µm, 27 µm, 28 µm, 29 µm, 30 µm, 31 µm, 32 µm, 33 µm, 34 µm, 35 µm, 36 µm, 37 µm, 38 µm, 39 µm, 40 µm, 41 µm, 42 µm, 43 µm, 44 µm, 45 µm, 46 µm, 47 µm, 48 µm, 49 µm, 50 µm, 51 µm, 52 µm, 53 µm, 54 µm, 55 µm, 56 µm, 57 µm, 58 µm, 59 µm, 60 µm, 61 µm, 62 µm, 63 µm, 64 µm, 65 µm, 66 µm, 67 µm, 68 µm, 69 µm, 70 µm, 71 µm, 72 µm, 73 µm, 74 µm, 75 µm, 76 µm, 77 µm, 78 µm, 79 µm, 80 µm, or 81 µm in size, including all ranges and subranges therebetween. In some embodiments, the method provides crystals of the selected cannabinoid that are greater than or equal to about 5 µm, about 10 µm, about 15 µm, about 20 µm, about 25 µm, or about 30 µm in size. In some embodiments, the method provides crystals of the selected cannabinoid that are greater than or equal to about 25 µm in size, for example, 25 µm, about 26 µm, about 27 µm, about 28 µm, about 29 µm, about 30 µm, about 31 µm, about 32 µm, about 33 µm, about 34 µm, about 35 µm, or more. In some embodiments, the method provides crystals that are less than about 100 µm, less than about 110 µm, less than about 120 µm, less than about 130 µm, less than about 140 µm, or less than about 150 µm. In some embodiments, the method provides crystals between about 2 µm and 150 µm, 2 µm and 140 µm, 2 µm and 130 µm, 2 µm and 120 µm, 2 µm and 110 µm, 2 µm and 100 µm, 10 µm and 150 µm, 10 µm and 140 µm, 10 µm and 130 µm, 10 µm and 120 µm, 2 µm and 110 µm, 10 µm and 100 µm, 20 µm and 150 µm, 20 µm and 140 µm, 20 µm and 130 µm, 20 µm and 120 µm, 20 µm and 110 µm, or 20 µm and 100 µm in size.

In some embodiments, at least 85%, 86%, 87%, 88%, 89%, 90%, 91%, 92%, 93%, 94%, or 95% of the cannabinoid in a cannabinoid solution forms into crystals of at least 2 µm, 3 µm, 4 µm, 5 µm, 6 µm, 7 µm, 8 µm, 9 µm, 10 µm, 11 µm, 12 µm, 13 µm, 14 µm, 15 µm, 16 µm, 17 µm, 18 µm, 19 µm, 20 µm, 21 µm, 22 µm, 23 µm, 24 µm, 25 µm, 26 µm, 27 µm, 28 µm, 29 µm, 30 µm, 31 µm, 32 µm, 33 µm, 34 µm, 35 µm, 36 µm, 37 µm, 38 µm, 39 µm, 40 µm, 41 µm, 42 µm, 43 µm, 44 µm, 45 µm, 46 µm, 47 µm, 48 µm, 49 µm, 50 µm, 51 µm, 52 µm, 53 µm, 54 µm, 55 µm, 56 µm, 57 µm, 58 µm, 59 µm, 60 µm, 61 µm, 62 µm, 63 µm, 64 µm, 65 µm, 66 µm, 67 µm, 68 µm, 69 µm, 70 µm, 71 µm, 72 µm, 73 µm, 74 µm, 75 µm, 76 µm, 77 µm, 78 µm, 79 µm, 80 µm, or 81 µm in size, including all ranges and subranges therebetween.

In some embodiments, the method provides crystals of the selected cannabinoid that are substantially homogenous in size. The term "substantially homogenous in size" means that greater than 70%, greater than 75%, greater than 80%, greater than 85%, greater than 90%, greater than 95%, greater than 96%, greater than 97%, greater than 98%, greater than 99%, or 100% of the crystals of the selected cannabinoid exhibit a size that is within about plus or minus 20%, 30%, 40%, 50%, 75%, or 100% of the mean crystal size.

In some embodiments, at least 90%, for example, at least 91%, at least 92%, at least 93%, at least 94%, at least 95%, at least 96%, at least 97%, at least 98%, at least 99%, or 100% of the selected cannabinoid is crystallized from the solution containing a substantially dissolved cannabinoid. In some embodiments, at least 95%, for example, at least 95%, at least 96%, at least 97%, at least 98%, at least 99%, or 100% of the selected cannabinoid is crystallized from the solution containing a substantially dissolved cannabinoid.

In some embodiments, at least 90%, for example, at least 91%, at least 92%, at least 93%, at least 94%, at least 95%, at least 96%, at least 97%, at least 98%, at least 99%, or 100% of the selected cannabinoid is crystallized from the solution containing a substantially dissolved cannabinoid, within about 1 hour to about 24 hours, within about 4 hours to about 10 hours, within about 10 hours to about 16 hours, or within about 16 to about 24 hours, including all values and ranges in between, including about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours. In some embodiments, greater than or equal to about 95% of the selected cannabinoid is crystallized out of solution within about 10 hours.

IIIB. Method of Purifying a Selected Cannabinoid from a Mixture of Cannabinoids

In some embodiments, provided herein is a method of purifying a selected cannabinoid from a mixture of cannabinoids, said method comprising: (a) providing a mixture of cannabinoids comprising a crystallized cannabinoid, wherein the crystallized cannabinoid comprises crystals that are at least about 25 µm in size; (b) forcing the mixture of cannabinoids through a filter, said filter having a pore size smaller than about 2 µm or smaller than about 25 µm; wherein this step is performed at a temperature below the melting point of the crystallized cannabinoid, wherein the crystallized cannabinoid remains on the filter; and (c) collecting the crystallized cannabinoid from the filter, thereby purifying the selected cannabinoid. In some embodiments, the selected cannabinoid is selected from the group consisting of CBN, CBD, THC, THCV, CBDA, CBDV, THCA, CBG, CBGA, CBNA, CBDVA, CBCA, and CBC. In some embodiments, the method comprises purifying a selected cannabinoid from non-specific lipid-soluble material. In some embodiments, the method comprises purifying a selected cannabinoid from one or more other cannabinoids.

Providing a Mixture Comprising a Crystallized Cannabinoid

In some embodiments, the method comprises providing a mixture comprising a crystallized cannabinoid. In some embodiments, the method comprises providing a mixture of cannabinoids comprising a crystallized cannabinoid. In some embodiments, the crystallized cannabinoid comprises crystals that are at least about 2 µm in size, for example, at least about 2 µm, at least about 3 µm, at least about 4 µm, at least about 5 µm, at least about 6 µm, at least about 7 µm, at least about 8 µm, at least about 9 µm, at least about 10 µm, at least about 11 µm, at least about 12 µm, at least about 13 µm, at least about 14 µm, at least about 15 µm, at least about 16 µm, at least about 17 µm, at least about 18 µm, at least about 19 µm, or at least about 20 µm in size. In some embodiments, the crystallized cannabinoid comprises crystals that are between about 2 µm and 5 µm in size, for example, about 2 µm, about 2.5 µm, about 3 µm, about 3.5 µm, about 4 µm, about 4.5 µm, or about 5 µm in size. In some embodiments, the crystals of the selected cannabinoid are greater than or equal to about 5 µm, about 10 µm, about 15 µm, about 20 µm, about 25 µm, or about 30 µm in size. In some embodiments, the crystals of the selected cannabinoid are greater than or equal to about 25 µm in size, for example, about 25 µm, about 26 µm, about 27 µm, about 28 µm, about 29 µm, about 30 µm, about 31 µm, about 32 µm, about 33 µm, about 34 µm, about 35 µm, or more. In some embodiments, at least 85%, 86%, 87%, 88%, 89%, 90%, 91%, 92%, 93%, 94%, or 95% of the cannabinoid in a cannabinoid solution forms into crystals of at least 2 µm, 3 µm, 4 µm, 5 µm, 6 µm, 7 µm, 8 µm, 9 µm, 10 µm, 11 µm, 12 µm, 13 µm, 14 µm, 15 µm, 16 µm, 17 µm, 18 µm, 19 µm, 20 µm, 21 µm, 22 µm, 23 µm, 24 µm, 25 µm, 26 µm, 27 µm, 28 µm, 29 µm, 30 µm, 31 µm, 32 µm, 33 µm, 34 µm, 35 µm, 36 µm, 37 µm, 38 µm, 39 µm, 40 µm, 41 µm, 42 µm, 43 µm, 44 µm, 45 µm, 46 µm, 47 µm, 48 µm, 49 µm, 50 µm, 51 µm, 52 µm, 53 µm, 54 µm, 55 µm, 56 µm, 57 µm, 58 µm, 59 µm, 60 µm, 61 µm, 62 µm, 63 µm, 64 µm, 65 µm, 66 µm, 67 µm, 68 µm, 69 µm, 70 µm, 71 µm, 72 µm, 73 µm, 74 µm, 75 µm, 76 µm, 77 µm, 78 µm, 79 µm, 80 µm, or 81 µm in size, including all ranges and subranges therebetween.

In some embodiments, the mixture comprising a crystallized cannabinoid is produced using the methods of Section IIIA In some embodiments, the mixture is a mixture of two or more cannabinoids. In some embodiments, the mixture comprising a crystallized cannabinoid contains a single cannabinoid present in both a crystallized and dissolved state.

In some embodiments, a mixture comprising a crystallized cannabinoid is produced by allowing *Cannabis* oil to age for at least one week, at least two weeks, at least three weeks, at least four weeks, at least five weeks, at least 1 month, at least 2 months, at least 3 months, at least 4 months, at least 5 months, at least 6 months, at least 7 months, at least 8 months, at least 9 months, at least 10 months, at least 11 months, or at least 12 months.

In some embodiments, a mixture comprising a crystallized cannabinoid comprises non-specific lipid-soluble material or "ballast" e.g. waxes, wax esters and glycerides, unsaturated fatty acid residues, terpenes, carotenes, chlorophyll, flavonoids, pigments, sugars, cellulose compounds, and minerals. In some embodiments, a mixture comprising a crystallized cannabinoid comprises one or more additional cannabinoids. Examples of cannabinoids are provided throughout this disclosure.

Forcing the Mixture Through a Filter

In some embodiments, the method comprises forcing a mixture comprising a crystallized cannabinoid through a filter, said filter having a pore size smaller than about 2 µm or smaller than about 25 µm; wherein this step is performed at a temperature below the melting point of the crystallized cannabinoid, and wherein the crystallized cannabinoid remains on the filter. In some embodiments, the mixture is a mixture of cannabinoids.

In some embodiments, the method comprises forcing a mixture comprising a crystallized cannabinoid through a filter, said filter having a pore size smaller than about 2 µm or smaller than about 25 µm; wherein this step is performed at a temperature below the melting point of the crystallized cannabinoid, and wherein the crystallized cannabinoid remains on the filter.

In some embodiments, the filtration step is conducted between about 0.1° C. and about 20° C. below the melting point of the crystallized cannabinoid, for example, at least about 0.1° C., about 0.2° C., about 0.3° C., about 0.4° C., about 0.5° C., about 0.6° C., about 0.7° C., about 0.8° C., about 0.9° C., about 1° C., about 2° C., about 3° C., about 4° C., about 5° C., about 6° C., about 7° C., about 8° C., about 9° C., about 10° C., about 11° C., about 12° C., about 13° C., about 14° C., about 15° C., about 16° C., about 17° C., about 18° C., about 19° C., or about 20° C. below the melting point of the crystallized cannabinoid, including all values and ranges there between, inclusive of endpoints. In some embodiments, the filtration step is conducted between about 0.5° C. and 10° C. below the melting point of the crystallized cannabinoid.

In some embodiments, the method comprises forcing the mixture comprising a crystallized cannabinoid through a filter having a pore size smaller than 70%, 80%, 90%, or 95% of the crystallized cannabinoid. Thus, in some embodiments, the method comprises forcing the mixture comprising a crystallized cannabinoid through a filter having a pore size smaller than about 25 µm, for example, smaller than about 25 µm, smaller than about 24 µm, smaller than about 23 µm, smaller than about 22 µm, smaller than about 21 µm, smaller than about 20 µm, smaller than about 19 µm, smaller than about 18 µm, smaller than about 17 µm, smaller than about 16 µm, smaller than about 15 µm, smaller than about 14 µm, smaller than about 13 µm, smaller than about 12 µm, smaller than about 11 µm, smaller than about 10 µm, smaller than about 9 µm, smaller than about 8 µm, smaller than about 7 µm, smaller than about 6 µm, smaller than about 5 µm, smaller than about 4 µm, smaller than about 3 µm, smaller than about 2 µm, smaller than about 1.9 µm, smaller than about 1.8 µm, smaller than about 1.7 µm, smaller than about 1.6 µm, smaller than about 1.5 µm, smaller than about 1.4 µm, smaller than about 1.3 µm, smaller than about 1.2 µm, smaller than about 1.1 µm, smaller than about 1.0 µm, smaller than about 0.9 µm, smaller than about 0.8 µm, smaller than about 0.7 µm, smaller than about 0.6 µm, smaller than about 0.5 µm, smaller than about 0.4 µm, smaller than about 0.3 µm, smaller than about 0.2 µm, or smaller than about 0.1 µm. In some embodiments, the filter comprises hydrophilized poly(vinylildene difluoride) (PVDF), polyetheresulfone (PES), cellulose phosphate, diethylaminoethyl cellulose, polysufone, regenerated cellulose, nylon, cellulose nitrate, cellulose acetate, paper, pegylated PES, modified polyethersulfone, and sulfonated PES, or modified derivatives thereof.

In some embodiments, the method comprises forcing the mixture through the filter via centrifugation, application of force, (e.g. gravity, centripetal, pressure, or vacuum).

In some embodiments, the method comprises forcing the mixture comprising a crystallized cannabinoid through the filter via centrifugation. In some embodiments, the mixture is centrifuged at a speed between about 1000 rpm and about 20,000 rpm, for example, at least about 1000 rpm, about 2000 rpm, about 3000 rpm, about 4000 rpm, about 5000 rpm, about 6000 rpm, about 7000 rpm, about 8000 rpm, about 9000 rpm, about 10,000 rpm, about 11000 rpm, about 12000 rpm, about 13,000 rpm, about 14,000 rpm, about 15,000 rpm, about 16,000 rpm, about 17,000 rpm, about 18,000 rpm, about 19,000 rpm, and about 20,000 rpm, including all ranges and subranges therebetween. In some embodiments, the mixture of cannabinoids is centrifuged at a speed between about 1000 rpm and about 7500 rpm. In some embodiments, the mixture of cannabinoids is centrifuged at a speed between about 7500 rpm and about 20,000 rpm. In some embodiments, the mixture comprising a crystallized cannabinoid is centrifuged at a speed greater than or equal to about 20,000 rpm. In some embodiments, the mixture comprising a crystallized cannabinoid is centrifuged at a speed between about 1000 rpm and about 20,000 rpm for about 30 minutes, about 45 minutes, about 1 hour, about 1.5 hours, about 2 hours, about 2.5 hours, about 3 hours, about 3.5 hours, about 4 hours, or more.

In some embodiments, the method comprises forcing the mixture comprising a crystallized cannabinoid through the filter via centrifugation, and increasing temperature of the mixture during centrifugation. In some embodiments, the present disclosure teaches increasing the temperature, to a point below the melting temperature of the crystallized cannabinoid. Without wishing to be bound by any one theory, the inventors believe that increasing the temperature allows non-cannabinoid components to melt/soften and be pulled through the filter, thus removing impurities from the crystallized cannabinoid.

In some embodiments, the temperature of the mixture is increased to between about 20° C. and about 60° C., for example, about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., about 50° C., about 51° C., about 52° C., about 53° C., about 54° C., about 55° C., about 56° C., about 57° C., about 58° C., about 59° C., or about 60° C., including all values and ranges therebetween, inclusive of endpoints. In some embodiments, the temperature of the mixture is increased to about 40° C. during centrifugation. In some embodiments, after centrifugation, the mixture is cooled (e.g., allowed to naturally return) to ambient temperature (e.g., about 25° C.). In some embodiments, the mixture of cannabinoids is not cooled to ambient temperature after centrifugation.

In some embodiments, the mixture comprising a crystallized cannabinoid is centrifuged once, and subsequently, the filtrate which contains byproduct is removed. In some embodiments, the process is repeated one or more times. For example, the method may comprise (i) subjecting the mixture comprising a crystallized cannabinoid to centrifugation; (ii) removing the filtrate containing the byproduct, and repeating steps (i) and (ii). In some embodiments, steps (i) and (ii) are repeated at least once, at least twice, at least three times, at least four times, at least five times, at least six times, at least seven times, at least eight times, at least nine times, or at least ten times. In some embodiments, the mixture of cannabinoids is centrifuged at about 5000 rpm for about 90 minutes twice.

In some embodiments, the method comprises: (i) centrifuging the mixture comprising a crystallized cannabinoid and increasing the temperature during centrifugation; (ii) removing the filtrate and cooling the mixture to ambient temperature; (iii) centrifuging the mixture and increasing the temperature during centrifugation; and (iv) removing the filtrate and cooling the mixture to ambient temperature. In some embodiments filtering the mixture comprising a crystallized cannabinoid via centrifuge, with increased temperature (below the melting point of the crystal) results in a highly pure cannabinoid product.

In some embodiments, the method comprises: (i) centrifuging the mixture comprising a crystallized cannabinoid and increasing the temperature during centrifugation; (ii) removing the filtrate; (iii) centrifuging the mixture and increasing the temperature during centrifugation; and (iv) removing the filtrate.

In some embodiments, the method comprises: (i) centrifuging the mixture comprising a crystallized cannabinoid at a speed of at least about 3000 rpm (e.g., about 3000 rpm) for at least about 30 minutes and increasing the temperature to at least about 40° C. during centrifugation; (ii) removing the filtrate and cooling the mixture to ambient temperature; and repeating (i) and (ii) at least one time. In some embodiments, during step (i) or in the repeat of step (i), the temperature of the mixture increases to above 40° C., for example, a temperature of about 41° C., about 42° C., about 43° C., about 44° C., about 45° C., about 46° C., about 47° C., about 48° C., about 49° C., about 50° C., about 51° C., about 52° C., about 53° C., about 54° C., about 55° C., about 56° C., about 57° C., about 58° C., about 59° C., or about 60° C.

In some embodiments, the method comprises forcing the mixture through the filter via pressure. In some embodiments, the force is about 10-20,000 times the force of gravity (g), for example, about 10 g, about 50 g, about 100 g, about 200 g, about 300 g, about 400 g, about 500 g, about 600 g, about 700 g, about 800 g, about 900 g, about 1000 g, about 1250 g, about 1500 g, about 1750 g, about 2000 g, about 2250 g, about 2500 g, about 2750 g, about 3000 g, about 3250 g, about 3500 g, about 3750 g, about 4000 g, about 4250 g, about 4500 g, about 4750 g, about 5000 g, about 5250 g, about 5500 g, about 5750 g, about 6000 g, about 6250 g, about 6500 g, about 6750 g, about 7000 g, about 7250 g, about 7500 g, about 7750 g, about 8000 g, about 8250 g, about 8500 g, about 8750 g, about 9000 g, about 9250 g, about 9500 g, about 9750 g, about 10,000 g, about 10,250 g, about 10,500 g, about 10,750 g, about 11,000 g, about 11,250 g, about 11,500 g, about 11,750 g, about 12,000 g, about 12,250 g, about 12,500 g, about 12,750 g, about 13,000 g, about 13,250 g, about 13,500 g, about 13,750 g, about 14,000 g, about 14,250 g, about 14,500 g, about 14,750 g, about 15,000 g, about 15,250 g, about 15,500 g, about 15,750 g, about 16,000 g, about 16,250 g, about 16,500 g, about 16,750 g, about 17,000 g, about 17,250 g, about 17,500 g, about 17,750 g, about 18,000 g, about 18,250 g, about 18,500 g, about 18,750 g, about 19,000 g, about 19,250 g, about 19,500 g, about 19,750 g, about 20,000 g, or any value or range therebetween, inclusive of endpoints. In some embodiments, the pressure is between about 3 kg/cm$^2$ and about 7 kg/cm$^2$, for example, about 3 kg/cm$^2$, about 3.5, about 4 kg/cm$^2$, about 4.5 kg/cm$^2$, about 5 kg/cm$^2$, about 5.5 kg/cm$^2$, about 6 kg/cm$^2$, about 6.5 kg/cm$^2$, about 7 kg/cm$^2$, or any value or range therebetween, inclusive of endpoints. In some embodiments, the pressure is gravity. In some embodiments, the pressure is hydrostatic pressure. In some embodiments, the pressure is air pressure.

In some embodiments, the method comprises forcing the mixture through the filter via a vacuum. In some embodiments, the pressure of the vacuum is between about 0.001 atm and about 0.1 atm, for example, about 0.001 atm, about 0.005 atm, about 0.01 atm, about 0.02 atm, about 0.03 atm, about 0.04 atm, about 0.05 atm, about 0.06 atm, about 0.07 atm, about 0.08 atm, about 0.09 atm, or about 0.1 atm. In some embodiments, the pressure of the vacuum is between about −45 mmHg and −5 mmHg, for example, about −45 mmHg, about −40 mmHg, about −35 mmHg, about −30 mmHg, about −25 mmHg, about −20 mmHg, about −15 mmHg, about −10 mmHg, or about −5 mmHg. In some embodiments, the pressure of the vacuum is less than about 1 micron. In some embodiments, the pressure of the vacuum is less than about 1 micron. In some embodiments, the pressure of the vacuum is between about −45 inHg and −5 inHg, for example, about −45 inHg, about −40 inHg, about −35 inHg, about −30 inHg, about −25 inHg, about −20 inHg, about −15 inHg, about −10 inHg, or about −5 inHg. In some embodiments, the pressure of the vacuum is about −25 mmHg. In some embodiments, the pressure of the vacuum is about −25 inHg.

In some embodiments, after forcing the mixture through the filter, crystals of the selected cannabinoid are retained on the filter.

Collecting the Crystallized Cannabinoid from the Filter

In some embodiments, the crystallized cannabinoid is collected from the filter, thereby purifying the selected cannabinoid. In some embodiments, the crystallized cannabinoid is selected from the group consisting of CBN, CBD, THC, THCV, CBDA, CBDV, THCA, CBG, CBGA, CBNA, CBDVA, CBCA, and CBC. In some embodiments, the collected crystallized cannabinoid is at least 85%, at least 86%, at least 87%, at least 89%, at least 90%, at least 91%, at least 92%, at least 93%, at least 94%, at least 95%, at least 96%, at least 97%, at least 98%, or at least 99% pure. In some embodiments, the collected crystallized cannabinoid is at least 98% pure. In some embodiments, the collected crystallized cannabinoid comprises crystals that are at least about 2 μm in size, for example, at least about 2 μm, at least about 3 μm, at least about 4 μm, at least about 5 μm, at least about 6 μm, at least about 7 μm, at least about 8 μm, at least about 9 µm, at least about 10 µm, at least about 11 µm, at least about 12 µm, at least about 13 µm, at least about 14 µm, at least about 15 µm, at least about 16 µm, at least about 17 µm, at least about 18 µm, at least about 19 µm, or at least about 20 µm in size. In some embodiments, the collected crystallized cannabinoid comprises crystals that are between about 2 µm and 5 µm in size, for example, about 2 µm, about 2.5 µm, about 3 µm, about 3.5 µm, about 4 µm, about 4.5 µm, or about 5 µm, in size. In some embodiments, the collected crystallized cannabinoid comprises crystals that are at least about 5 µm, about 10 µm, about 15 µm, about 20 µm, about 25 µm, or about 30 µm in size. In some embodiments, the collected crystallized cannabinoid comprises crystals that are at least about 25 µm in size, for example, 25 µm, about 26 µm, about 27 µm, about 28 µm, about 29 µm, about 30 µm, about 31 µm, about 32 µm, about 33 µm, about 34 µm, about 35 µm, or more.

Optional Additional Purification and Processing Steps

In some embodiments, the crystallized cannabinoid is subjected to one or more additional purification steps.

In some embodiments, the crystallized cannabinoid is washed with a solvent. In some embodiments, washing occurs in a glass container, for example, a beaker or a flask. In some embodiments, the solvent is water. In some embodiments, the solvent comprises a salt. Non-limiting examples of salts include sodium chloride, potassium chloride, ammonium chloride, sodium acetate, sodium citrate, copper sulfate, sodium iodide, ammonium sulfate, and sodium sulfate.

In some embodiments, the solvent comprises a buffer. The buffer may be an inorganic or an organic buffer. Non-limiting examples of buffers include phosphate buffered saline (PBS), phosphate, succinate, citrate, borate, maleate, cacodylate, N-(2-Acetamido)iminodiacetic acid (ADA), 2-(N-morpholino)-ethanesulfonic acid (MES), N-(2-acetamido)-2-aminoethanesulfonic acid (ACES), piperazine-N,N'-2-ethanesulfonic acid (PIPES), 2-(N-morpholino)-2-hydroxypropanesulfonic acid (MOPSO), N,N-bis-(hydroxyethyl)-2-aminoethanesulfonic acid (BES), 3-(N-morpholino)-propanesulfonic acid (MOPS), N-tris-(hydroxymethyl)-2-ethanesulfonic acid (TES), N-2-hydroxyethyl-piperazine-N-2-ethanesulfonic acid (HEPES), 3-(N-tris-(hydroxymethyl) methylamino)-2-hydroxypropanesulfonic acid (TAPSO), 3-(N,N-Bis[2-hydroxyethyl] amino)-2-hydroxypropanesulfonic acid (DIPSO), N-(2-Hydroxyethyl)piperazine-N'-(2-hydroxypropanesulfonic acid) (HEPPSO), 4-(2-Hydroxyethyl)-1-piperazinepropanesulfonic acid (EPPS), N-[Tris(hydroxymethyl)methyl]glycine (Tricine), N,N-Bis(2-hydroxyethyl)glycine (Bicine), (2-Hydroxy-1,1-bis(hydroxymethyl)ethyl)amino]-1-propanesulfonic acid (TAPS), N-(1,1-Dimethyl-2-hydroxyethyl)-3-amino-2-hydroxypropanesulfonic acid (AMPSO), tris (hydroxy methyl) amino-methane (Tris), TRIS-Acetate-EDTA (TAE), glycine, bis[2-hydroxyethyl]iminotris[hydroxymethyl]methane (BisTris), or combinations thereof.

In some embodiments, the concentration of a buffer and/or salt is between about 0.1 mM and 1 M, for example, between about 10 mM to about 1 M, between about 20 mM and about 500 mM, between about 50 mM and about 300 mM, between about 0.1 mM and about 50 mM, or between about 0.5 mM and about 20 mM. In some embodiments, the concentration of the buffer and/or salt is about 0.1 mM, about 0.2 mM, about 0.3 mM, about 0.4 mM, about 0.5 mM, about 0.6 mM, about 0.7 mM, about 0.8 mM, about 0.9 mM, about 1 mM, about 10 mM, about 20 mM, about 30 mM, about 40 mM, about 50 mM, about 60 mM, about 70 mM, about 80 mM, about 90 mM, about 100 mM, about 110 mM, about 120 mM, about 130 mM, about 140 mM, about 150 mM, about 160 mM, about 170 mM, about 180 mM, about 190 mM, about 200 mM, about 210 mM, about 220 mM, about 230 mM, about 240 mM, about 250 mM, about 260 mM, about 270 mM, about 280 mM, about 290 mM, about 300 mM, about 310 mM, about 320 mM, about 330 mM, about 340 mM, about 350 mM, about 360 mM, about 370 mM, about 380 mM, about 390 mM, about 400 mM, about 410 mM, about 420 mM, about 430 mM, about 440 mM, about 450 mM, about 460 mM, about 470 mM, about 480 mM, about 490 mM, about 500 mM, about 510 mM, about 520 mM, about 530 mM, about 540 mM, about 550 mM, about 560 mM, about 570 mM, about 580 mM, about 590 mM, about 600 mM, about 610 mM, about 620 mM, about 630 mM, about 640 mM, about 650 mM, about 660 mM, about 670 mM, about 680 mM, about 690 mM, about 700 mM, about 710 mM, about 720 mM, about 730 mM, about 740 mM, about 750 mM, about 760 mM, about 770 mM, about 780 mM, about 790 mM, about 800 mM, about 810 mM, about 820 mM, about 830 mM, about 840 mM, about 850 mM, about 860 mM, about 870 mM, about 880 mM, about 890 mM, about 900 mM, about 910 mM, about 920 mM, about 930 mM, about 940 mM, about 950 mM, about 960 mM, about 970 mM, about 980 mM, about 990 mM, or about 1 M, including all ranges and subranges therebetween.

In some embodiments, the crystallized cannabinoid is washed with a solvent at a temperature between about 0.1° C. and about 30° C., for example, about 0.1° C., about 0.2° C., about 0.3° C., about 0.4° C., about 0.5° C., about 0.6° C., about 0.7° C., about 0.8° C., about 0.9° C., about 1° C., about 2° C., about 3° C., about 4° C., about 5° C., about 6° C., about 7° C., about 8° C., about 9° C., about 10° C., about 11° C., about 12° C., about 13° C., about 14° C., about 15° C., about 16° C., about 17° C., about 18° C., about 19° C., about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., about 50° C., about 51° C., about 52° C., about 53° C., about 54° C., about 55° C., about 56° C., about 57° C., about 58° C., about 59° C., or about 60° C. including all values and ranges therebetween, inclusive of endpoints. In some embodiments, the crystallized cannabinoid is washed with a solvent at a temperature between about 1° C. and about 8° C.

In some embodiments, the pH of the solvent is between about 5.5 and about 8.5. For example, the pH of the solvent is about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, or about 8.5, including all values and ranges therebetween, inclusive of endpoints. In some embodiments, the pH of the solvent is about 6.5.

In some embodiments, the crystallized cannabinoid is dried. In some embodiments, the crystallized cannabinoid is dried in a vacuum oven, in a desiccator, or using a filtration flask. Suitable temperatures and pressures for the vacuum oven are described throughout this disclosure, for example, in Section IIIA In some embodiments, the pressure of the vacuum is from about −45 inHg to −5 inHg. For example, the pressure of the vacuum may be stronger than about −45 inHg, about −40 inHg, about −35 inHg, about −30 inHg, about −25 inHg, about −20 inHg, about −15 inHg, about −10 inHg, or about −5 inHg.

In some embodiments, the temperature of the vacuum oven is from 25° C. to about 125° C. For example, the temperature of the vacuum oven may be about 25° C., about 30° C., about 35° C., about 40° C., about 45° C., about 50° C., about 55° C., about 60° C., about 65° C., about 70° C., about 75° C., about 80° C., about 85° C., about 90° C., about 90° C., about 95° C., about 100° C., about 105° C., about 110° C., about 115° C., about 120° C., about 125° C., including subranges and ranges therebetween. In some embodiments, the temperature of the vacuum oven is about 35° C.

In some embodiments, the same pressures may be used to dry a crystallized cannabinoid using a desiccator or by vacuum filtration using a filtration flask.

In some embodiments, the crystallized cannabinoid is homogenized. In some embodiments, homogenizing a crystallized cannabinoid comprises breaking the crystallized cannabinoid apart into small particles. In some embodiments, the crystallized cannabinoid is homogenized using a rotor stator homogenizer (e.g., with the crystals suspended in water). In some embodiments, the crystallized cannabinoid is homogenized at a speed from about 5000 rpm to about 50,000 rpm, for example, about 5000 rpm, about 6000 rpm, about 7000 rpm, about 8000 rpm, about 9000 rpm, about 10,000 rpm, about 11,000 rpm, about 12,000 rpm, about 13,000 rpm, about 14,000 rpm, about 15,000 rpm, about 16,000 rpm, about 17,000 rpm, about 18,000 rpm, about 19,000 rpm, about 20,000 rpm, about 21,000 rpm, about 22,000 rpm, about 23,000 rpm, about 24,000 rpm, about 25,000 rpm, about 26,000 rpm, about 27,000 rpm, about 28,000 rpm, about 29,000 rpm, about 30,000 rpm, about 31,000 rpm, about 32,000 rpm, about 33,000 rpm, about 34,000 rpm, about 35,000 rpm, about 36,000 rpm, about 37,000 rpm, about 38,000 rpm, about 39,000 rpm, about 40,000 rpm, about 41,000 rpm, about 42,000 rpm, about 43,000 rpm, about 44,000 rpm, about 44,000 rpm, about 45,000 rpm, about 46,000 rpm, about 47,000 rpm, about 48,000 rpm, about 49,000 rpm, or about 50,000 rpm, including all values and ranges therebetween. In some embodiments, the crystallized cannabinoid is homogenized at a speed of 15,000 rpm. In some embodiments, the crystallized cannabinoid is homogenized for about 1 minute (min) to about 120 min, for example, about 1 min, about 2 min, about 3 min, about 4 min, about 5 min, about 6 min, about 7 min, about 8 min, about 9 min, about 10 min, about 11 min, about 12 min, about 13 min, about 14 min, about 15 min, about 16 min, about 17 min, about 18 min, about 19 min, about 20 min, about 21 min, about 22 min, about 23 min, about 24 min, about 25 min, about 26 min, about 27 min, about 28 min, about 29 min, about 30 min, about 31 min, about 32 min, about 33 min, about 34 min, about 35 min, about 36 min, about 37 min, about 38 min, about 39 min, about 40 min, about 41 min, about 42 min, about 43 min, about 44 min, about 45 min, about 46 min, about 47 min, about 48 min, about 49 min, about 50 min, about 51 min, about 52 min, about 53 min, about 54 min, about 55 min, about 56 min, about 57 min, about 58 min, about 59 min, about 60 min, about 61 min, about 62 min, about 63 min, about 64 min, about 65 min, about 66 min, about 67 min, about 68 min, about 69 min, about 70 min, about 71 min, about 72 min, about 73 min, about 74 min, about 75 min, about 76 min, about 77 min, about 78 min, about 79 min, about 80 min, about 81 min, about 82 min, about 83 min, about 84 min, about 85 min, about 86 min, about 87 min, about 88 min, about 89 min, about 90 min, about 91 min, about 92 min, about 93 min, about 94 min, about 95 min, about 96 min, about 97 min, about 98 min, about 99 min, about 100 min, about 101 min, about 102 min, about 103 min, about 104 min, about 105 min, about 106 min, about 107 min, about 108 min, about 109 min, about 110 min, about 111 min, about 112 min, about 113 min, about 114 min, about 115 min, about 116 min, about 117 min, about 118 min, about 119 min, or about 120 min, including all values and ranges therebetween, inclusive of endpoints.

In some embodiments, the methods of the disclosure provide cannabinoid compositions containing a substantially pure selected cannabinoid. In some embodiments, the cannabinoid composition comprises at least about 95%, at least about 96%, at least about 97%, at least about 98%, or at least about 99% of the selected cannabinoid by weight of the solution. In some embodiments, the substantially pure cannabinoid is at least about 95%, at least about 96%, at least about 97%, at least about 98%, or at least about 99% pure.

Processing of Byproducts

In some embodiments, byproducts of the methods described herein are processed to yield additional products. In some embodiments, the product is a purified cannabinoid, a wax, or a terpene.

In some embodiments, a byproduct is the filtrate resulting from forcing the crystallized cannabinoid solution through a filter. In some embodiments, the byproduct is processed to selectively crystallize and/or purify a cannabinoid. In some embodiments, processing the byproduct comprises (i) subjecting the filtrate to a technique which results in a solution comprising a second selected cannabinoid with a concentration greater than or equal to its supersaturation point; (ii) increasing the temperature of the solution until the second selected cannabinoid is substantially dissolved in the solution; and (iii) decreasing the temperature of the solution to about −5° C. or lower to produce a cooled solution wherein the second selected cannabinoid crystallizes out of solution, thereby forming crystals of the second selected cannabinoid. In some embodiments, the second selected cannabinoid is the same as the initial selected cannabinoid that is purified. In some embodiments, the second selected cannabinoid is different than the initial selected cannabinoid that is purified. In some embodiments, the technique used to create a solution comprising a second selected cannabinoid with a concentration greater than or equal to its supersaturation point is distillation, for example, fractional distillation. In some embodiments, a mixture comprising crystals of the second selected cannabinoid is purified by (i) forcing the mixture through a filter, said filter having a pore size smaller than about 2 µm; wherein this step is performed at a temperature below the melting point of the second crystallized cannabinoid, wherein the crystallized cannabinoid remains on the filter; and (ii) collecting the second crystallized cannabinoid from the filter, thereby purifying the second selected cannabinoid.

In some embodiments, washing the crystallized cannabinoid creates a byproduct formed on the surface of the container used for washing. In some embodiments, the byproduct contains fats and waxes.

EXAMPLES

Figure 1:
FIG. 1 shows CBD crystals resulting from the method of selective crystallization of cannabinoids described herein.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby Example 1A—Crystallization of a Selected Cannabinoid from a Solution Comprising a Plurality of Cannabinoids CBD was crystallized from a solution comprising a plurality of cannabinoids. Table A1 shows the cannabinoids within the CBD-rich solution comprising a plurality of cannabinoids. The solution contained CBD at a concentration of 76.87% by weight. The solution of Table A1 was heated to 60° C. until the cannabinoid was substantially dissolved in the solution (e.g. for about five minutes). The fully dissolved solution was then exposed to the following nucleation factors: agitation (intense stirring) and cold shock (cooling the solution to −20° C.). Subsequently, a cannabinoid seed crystal was introduced to the cooled solution, and the solution was exposed to a vacuum at a pressure of −25 inHg and a temperature of 34.4° C. The solution was left in the vacuum overnight. Then, the solution was removed from the vacuum, and the temperature and pressure were gradually adjusted to ambient temperature (~25° C.) and pressure (1 atm) over the course of two hours. The solution was incubated at ambient temperature for 4-10 hours. The method resulted in the formation of CBD crystals (FIG. 1).

TABLE A1

CBD-rich Solution Comprising a Plurality of Cannabinoids.

| Compound | % by weight (w/w) |
|---|---|
| THCA | ND |
| Delta 9-tetrahydrocannabinol (Δ9-THC) | 3.67 |
| CBDA | 1.04 |
| CBD | 76.87 |
| Delta 8-tetrahydrocannabinol (Δ8-THC) | ND |
| CBNA | ND |
| CBN | 0.13 |
| Cannabigerolic acid (CBGA) | ND |
| CBG | 1.97 |
| THCVA | ND |
| THCV | 0.30 |
| CBDVA | ND |
| CBDV | 0.58 |
| CBCA | ND |
| CBC | 3.95 |

"ND" refers to a cannabinoid that is not detected.

Figure 2:
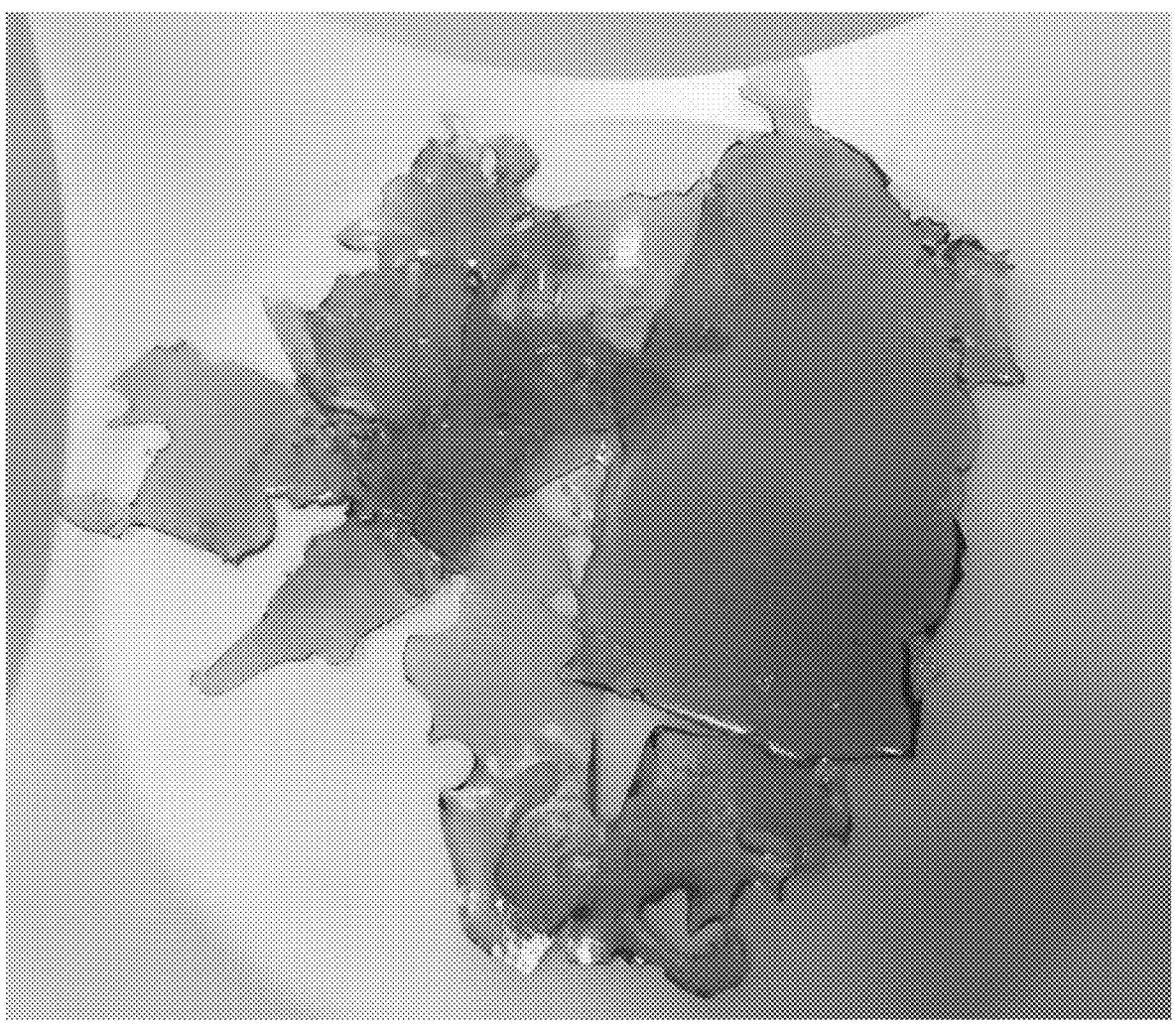
FIG. 2 is an image of THC-rich starting material for crystallization.
Figure 3A:
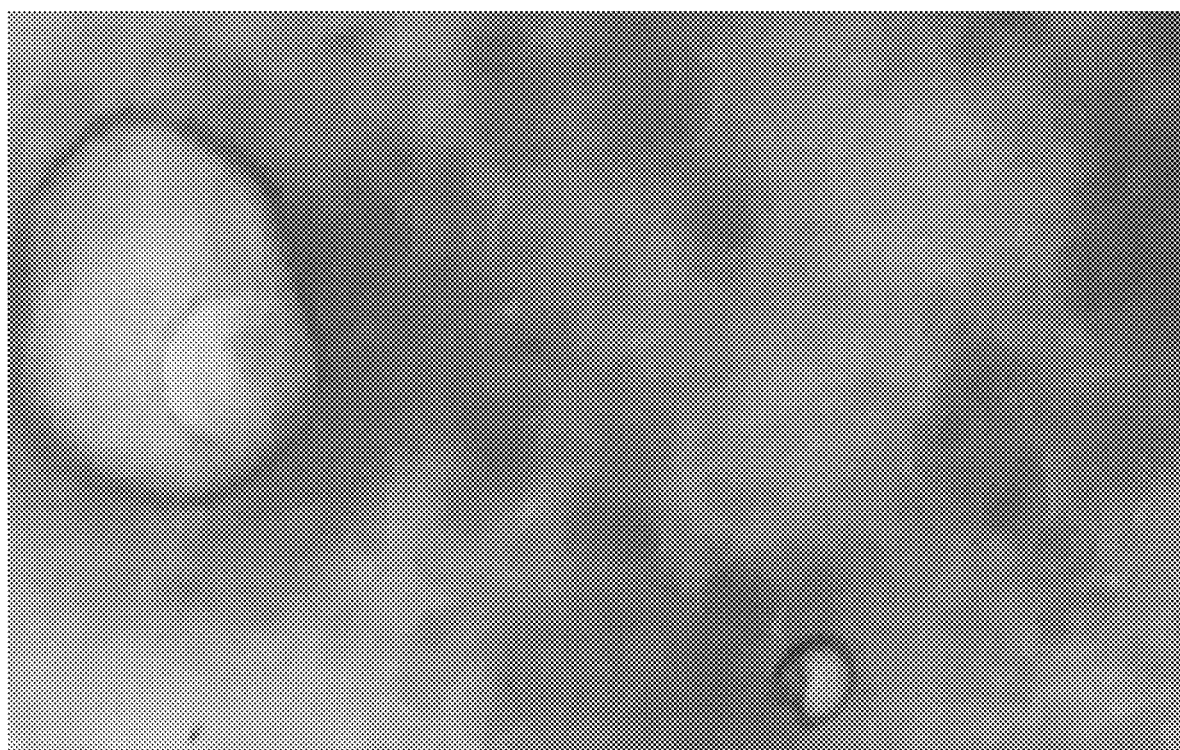
FIG. 3A is an image of THC crystals beginning to form after the THC-rich solution is cooled.
Figure 3B:
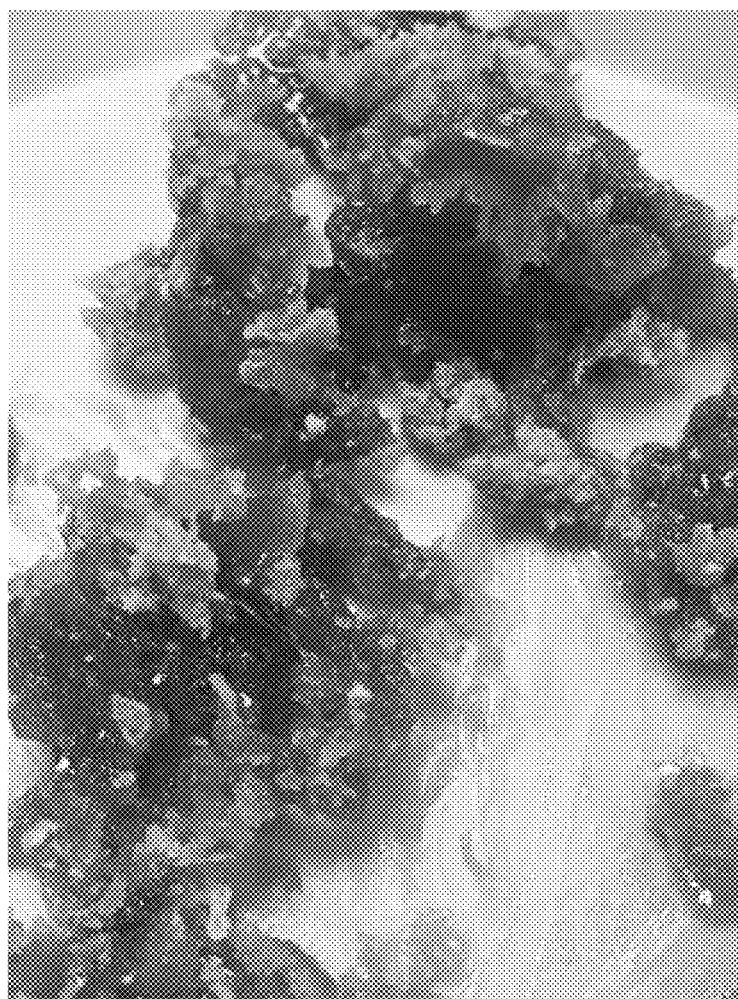
FIG. 3B is an image of THC crystals resulting from the method of selective crystallization of cannabinoids described herein.

THC was crystallized from a solution comprising a plurality of cannabinoids. FIG. 2 shows an image of THC-rich starting material. The THC-rich starting material contained 68% THCA, <1 THC, and <1 THCV. The THC-rich solution was heated to 60° C. The solution was mixed until the THC was dissolved. Subsequently, the heated solution was cold shocked (cooling the solution to −20° C.) and agitated. The cooled mixture was placed in a vacuum oven at a temperature of 34.4° C. at a pressure of −25 inHg, and a seed crystal of THC was introduced to the cooled mixture. The temperature and pressure were gradually adjusted to ambient temperature (~25° C.) and pressure (1 atm) over the course of two hours. The solution was incubated at ambient temperature for 4-10 hours. This procedure resulted in THC crystals (FIG. 3A and FIG. 3B).

Selective crystallization of CBNA, CBN, CBGA, CBG, THCVA, THCV, CBDVA, CBDV, CBCA, and CBD is performed using the methods described above.

Example 1B—A Method of Separating a Selected Cannabinoid from a Solution Comprising a Plurality of Cannabinoids The THC crystals and CBD crystals formed in Example 1A were separated from solution according to the following method. The solution was placed on a filter with a pore size less than 25 μm (Whatman paper), the filter was placed above a filtration flask, and the filtration flask was spun in a centrifuge at a speed of 5000 rpm for 90 minutes. During centrifugation, the temperature was increased from ambient temperature to 40° C. After centrifugation, the solution was cooled to ambient temperature. Subsequently, the solution was centrifuged again at 5000 rpm for 90 minutes.

After centrifugation, the crystallized CBD and/or THC was collected from the filter, and the byproduct (e.g. the filtrate) was saved for crystallization and/or purification of other cannabinoids. The crystallized CBD was 91.86% pure. Table A2 shows the composition of the CBD crystals.

TABLE A2

Composition of Cooled Solution Comprising CBD crystals

| Compound | % by weight (w/w) |
|---|---|
| THCA | ND |
| Delta 9-tetrahydrocannabinol (Δ9-THC) | 0.46 |
| CBDA | 0.22 |
| CBD | 91.86 |
| Delta 8-tetrahydrocannabinol (Δ8-THC) | ND |
| CBNA | ND |
| CBN | ND |
| Cannabigerolic acid (CBGA) | ND |
| CBG | 0.28 |
| THCVA | ND |
| THCV | ND |
| CBDVA | ND |
| CBDV | 0.43 |
| CBCA | ND |
| CBC | 0.56 |

"ND" refers to a cannabinoid that is not detected.

Additional purification/cleanup steps were conducted as follows: the THC and/or CBD powder was washed in water and shaken with a rotostator, and then centrifuged again. These steps are described below in more detail.

Figure 4A:
FIG. 4A is an image of a THC powder produced by (i) crystallizing THC from a solution containing a plurality of cannabinoids; (ii) separating the THC crystals from the solution by applying them to a filter; (iii) washing the THC crystals in cold water; and (iv) drying the THC crystals in a vacuum oven.
Figure 4B:
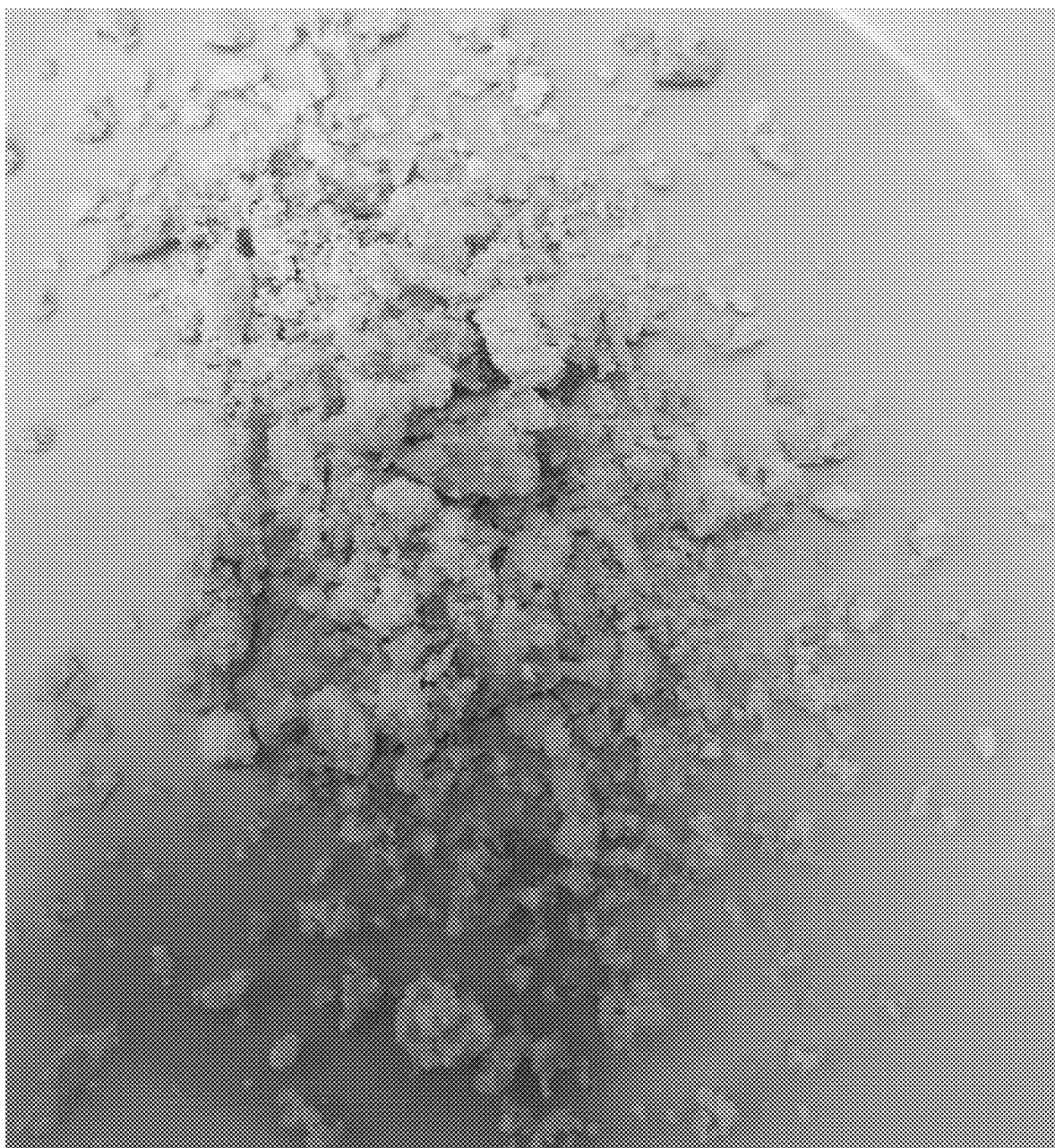
FIG. 4B is another image of a THC powder produced by (i) crystallizing THC from a solution containing a plurality of cannabinoids; (ii) separating the THC crystals from the solution by applying them to a filter; (iii) washing the THC crystals in cold water; and (iv) drying the THC crystals in a vacuum oven.

Oils, waxes, fats, and terpenes were removed from the THC and/or CBD crystals according to the following process. The THC and/or CBD crystals were placed into a beaker of water at a temperature between 1° C. and 8° C. at a pH of 6.5. A rotor stator homogenizer was applied to the water for five minutes at a speed of 15,000 rpm to disperse the CBD and/or THC crystals throughout the water. The CBD and/or THC mixture was forced through Whatman paper covering a 25 μm filtration flask. The filtrate contained terpenes and fats, and the walls of the beaker of the container contained fats and waxes. The CBD and/or THC remained on the filter. The CBD and/or THC was washed with water and collected from the filter. The CBD and/or THC was placed in a vacuum oven to purge water and dissolved terpenes. FIG. 4A and FIG. 4B show the resultant THC powder. Table A3 shows the composition of the resultant CBD powder. The composition of CBD contains 0% terpenes by weight.

TABLE A3

Composition of CBD crystals after washing with water and drying in a vacuum oven

| Compound | % by weight (w/w) |
| --- | --- |
| THCA | ND |
| Delta 9-tetrahydrocannabinol (Δ9-THC) | 0.49 |
| CBDA | 0.16 |
| CBD | 95.73 |
| Delta 8-tetrahydrocannabinol (Δ8-THC) | ND |
| CBNA | ND |
| CBN | ND |
| Cannabigerolic acid (CBGA) | ND |
| CBG | ND |
| THCVA | ND |
| THCV | ND |
| CBDVA | ND |
| CBDV | 0.42 |
| CBCA | ND |
| CBC | ND |
| Terpenes | ND |

"ND" refers to a cannabinoid that is not detected.

Figure 5:
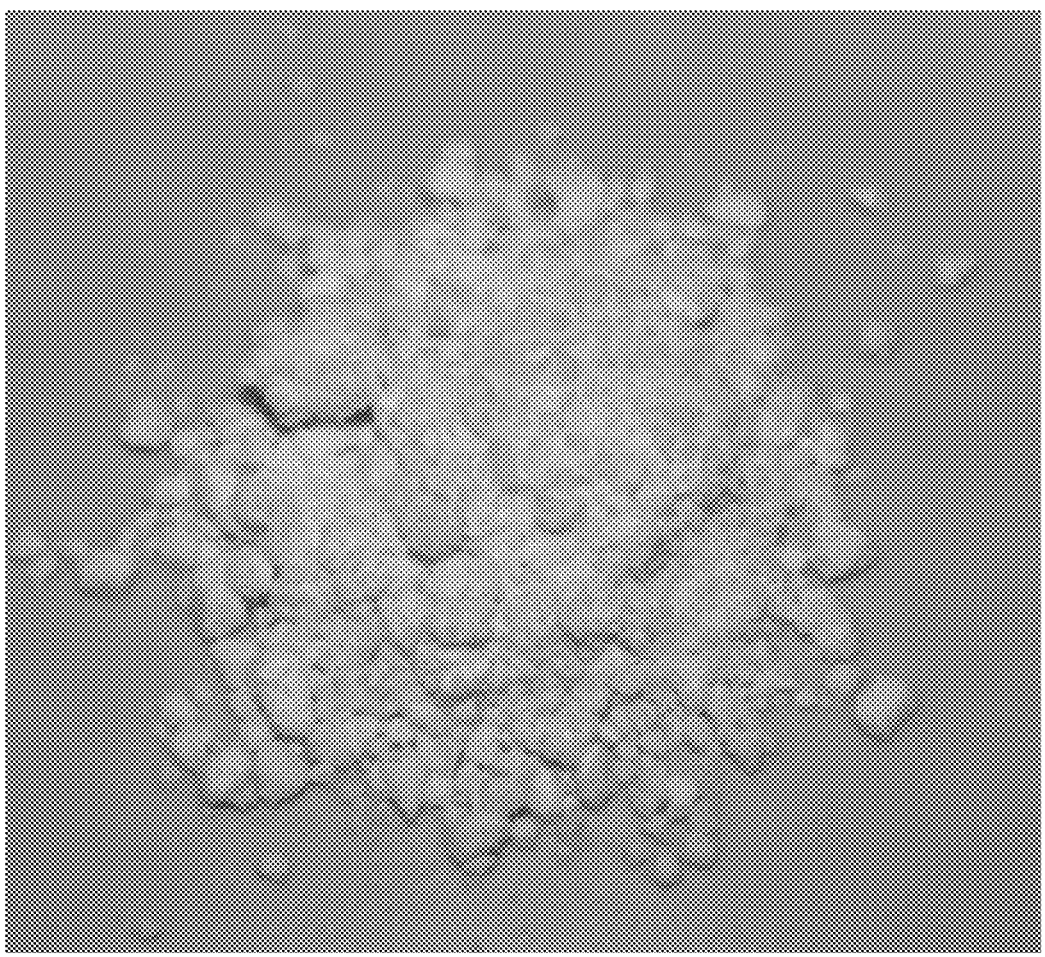
FIG. 5 is an image of CBD crystals that are 99.5% pure.
Figure 6:
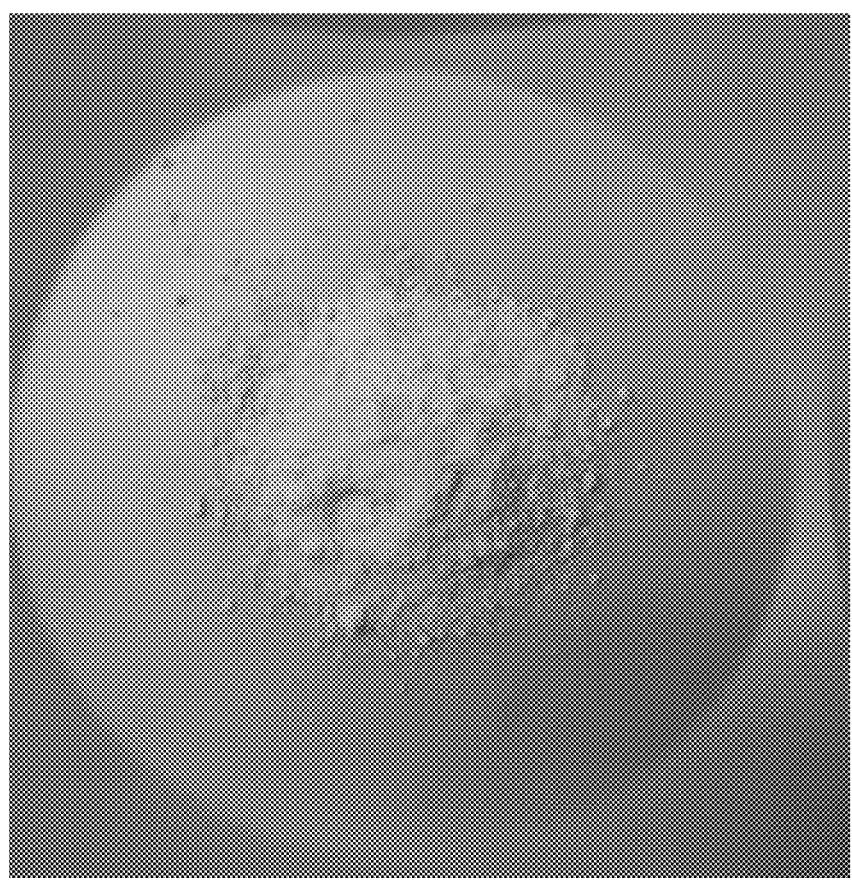
FIG. 6 is an image of THC crystals that are 100% pure.

The CBD and/or THC powder was further refined to remove the residual cannabinoids. Briefly, the method comprised (i) placing the CBD and/or THC powder on a filter on top of a filtration flask; (ii) centrifuging the CBD and/or THC powder at 5000 rpm for 90 minutes and increasing the temperature to 40° C. during centrifugation; (iii) removing the CBD and/or THC powder from the filter, and placing it on a new filter; and (iv) centrifuging the CBD and/or THC powder at 5000 rpm for 90 minutes. The CBD/and or THC powder was removed from the filter and placed in a vacuum oven at 33.3° C. and a pressure of −25 inHg for 24 hours. After this refinement step, the CBD was 99.5% pure, and the THC was 100% pure. FIG. 5 shows a picture of the CBD crystals. FIG. 6 shows a picture of THC crystals.

CBNA, CBN, CBGA, CBG, THCVA, THCV, CBDVA, CBDV, CBCA, and CBC crystals are similarly purified from a mixture of cannabinoids using the methods described above.

Example 2—Effect of Various Nucleation Factors on the Crystallization and/or Purification of a Selected Cannabinoid The effect of a nucleation factor on the crystallization and/or purification of a selected cannabinoid was evaluated. Briefly, a solution comprising a plurality of cannabinoids (i.e., a primary *cannabis* extract), wherein the selected cannabinoid is present in the solution at a concentration greater than or equal to its supersaturation point, and wherein the selected cannabinoid is the highest concentration cannabinoid in the solution is provided. All samples containing the plurality of cannabinoids were heated until the selected cannabinoid is substantially dissolved in the solution (e.g. 60° C. for about five minutes). These substantially dissolved solutions were then processed with one or more of the nucleation factors of the present disclosure, including: cold shock, vacuum, seed crystal, and mechanical agitation. Samples that did not receive cold shock treatment were allowed to cool naturally to room temperature sitting on the counter before further nucleation factors were applied. Crystallization of the cannabinoid was evaluated for each sample after 24 hours. The yield, purity, crystal size, and homogeneity of the crystals is measured. Experimental design and results are shown in Table A4.

TABLE A4

Solutions Evaluated in Example 2

| Solutions | Nucleation Factor(s) | Observation | Photograph of Solution after 24 hours |
| --- | --- | --- | --- |
| 1 | Cold Shock (reducing temperature to −5° C.) | The oil appears unchanged and resembles the control in every aspect. Cold shock alone not sufficient to crystallize selected cannabinoid. | FIG. 7A |
| 2 | Vacuum (−20 inHg for 24 hours) | Crystallization did not occur. Vacuum alone was not sufficient to crystallize the selected cannabinoid in this solution. Without wishing to be bound by any theory, Applicant believes that the lack of microbubbles rendered the vacuum ineffective. | FIG. 7B |
| 3 | Agitation (intense stirring) | Agitation was very effective in rapidly starting crystal formation. The intense agitation also dissolved microbubbles throughout the material which set up nucleation sites for crystallization at normal pressures. The material took on a thicker, more waxy appearance and texture. The light is much more diffuse across the surface and tight specular highlights are not seen. From visual inspection, it appeared that crystallization was incomplete. | FIG. 7C |

TABLE A4-continued

Solutions Evaluated in Example 2

| Solutions | Nucleation Factor(s) | Observation | Photograph of Solution after 24 hours |
|---|---|---|---|
| 4 | Seed crystal | No crystallization. Seed crystals alone were insufficient to crystallize the selected cannabinoid. | FIG. 7D |
| 5 | Cold Shock (reducing temperature to −5° C.) Agitation (intense stirring) Seed Crystal | This image shows partial microbubble formation that will lead to crystal formation. However, microbubble formation is non-homogenous. This is evident in an image, because different sides are different colors. Additionally, the surface of the oil has a tight specular sheen. These observations mean there aren't enough crystals or microbubble sites to diffuse or scatter the light across the surface. Without being bound by theory, it is possible that cold shock reduced the effectiveness of agitation (hand stirring) for crystallization by thickening the solution, without following up with vacuum capable of expanding/propagating the microbubbles. Stronger agitation of the more viscous cooled solution would be expected to increase crystallization. | FIG. 7F |
| 6 | Cold Shock Agitation (intense stirring) Vacuum (−20 inHg) | Solution 6 formed a crystalline solid. The air bubbles within the solution are composed of thin layers of crystals that have been suspended in a "foam". This product crystallized top down, with the lower portion being the non-crystallized components. Solution 6 is ideal for purification. | FIG. 7G |
| 7 | Agitation (intense stirring) Seed crystal Vacuum (−20 inHg) | Once again this is ideal. The material has lightened due to the crystal formation and the rising of the bubbles/foam inside of the vacuum oven, creating very thin films where crystals form. Solution 7 is ideal for purification. Applicant expects that only agitation and vacuum would also result in viable crystal formation. | FIG. 7H |
| 8 | Cold Shock Seed crystal Vacuum (−20 inHg) | Solution 8 did not yield a viable product. The image shows the seed crystals, unchanged, and with nothing growing from them, as well as larger bubbles from the vacuum process that do not act as good nucleation sites for crystal formation. The color is unchanged as there are no crystals to diffuse, scatter, or bend the light as it passes through. | FIG. 7I |

Figure 7A:
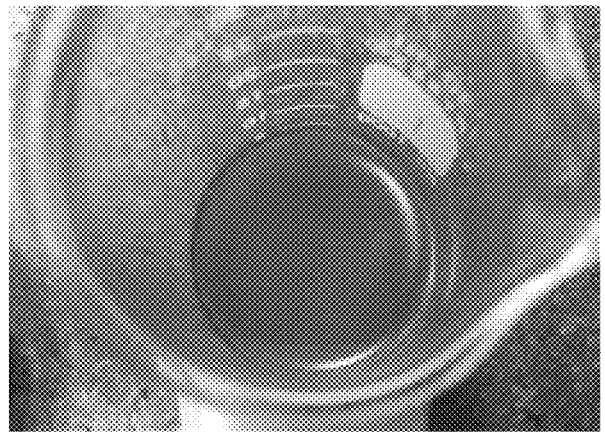
FIGS. 7A-7J are images of a solution containing a plurality of cannabinoids before or 24 hours after optional exposure to a nucleation factor, wherein the selected cannabinoid is CBD.
Figure 7B:
Figure 7C:
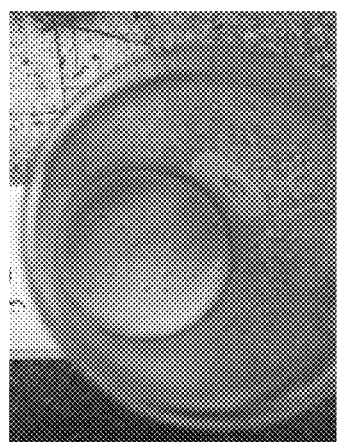
Figure 7D:
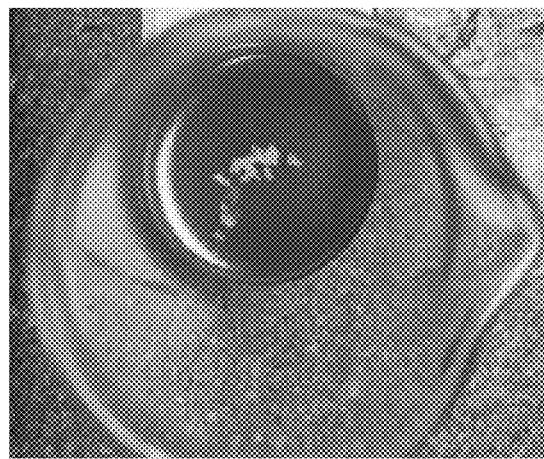
Figure 7E:
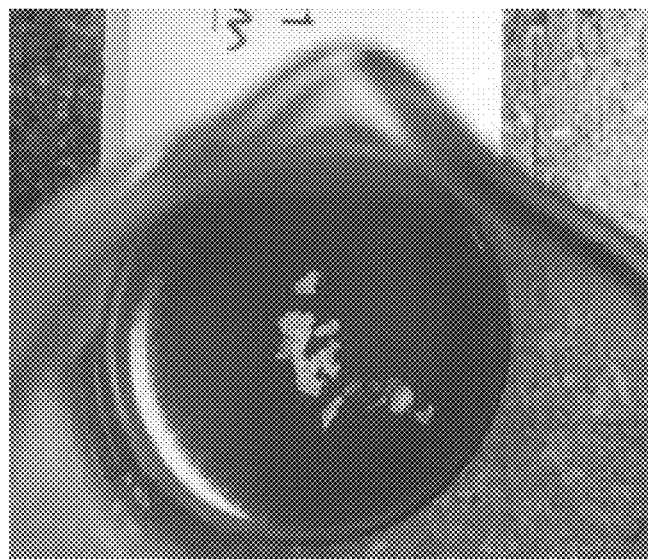
Figure 7F:
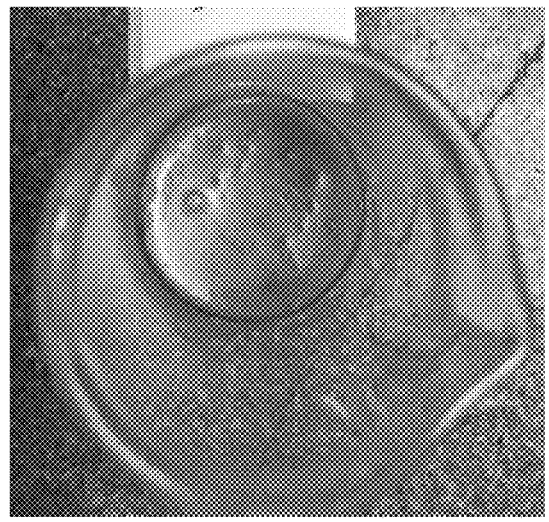
Figure 7G:
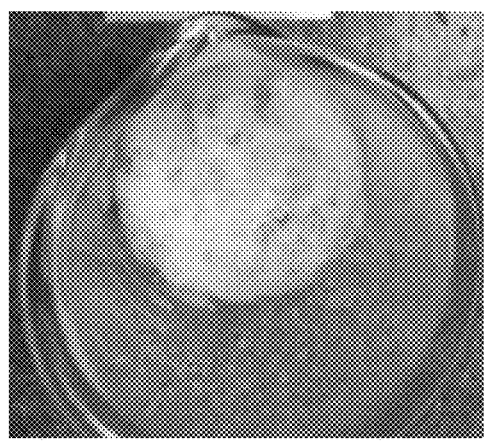
Figure 7H:
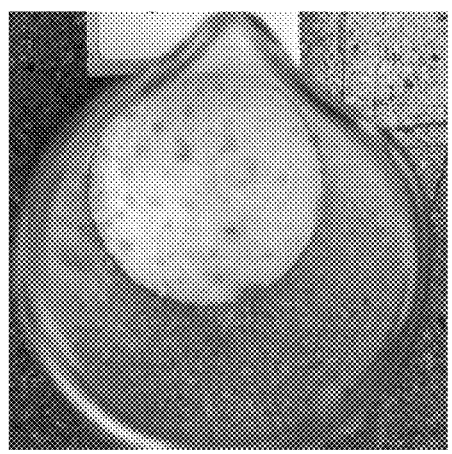
Figure 7I:
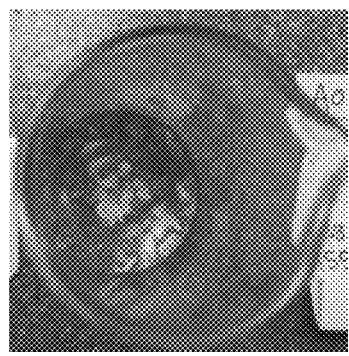
Figure 7J:
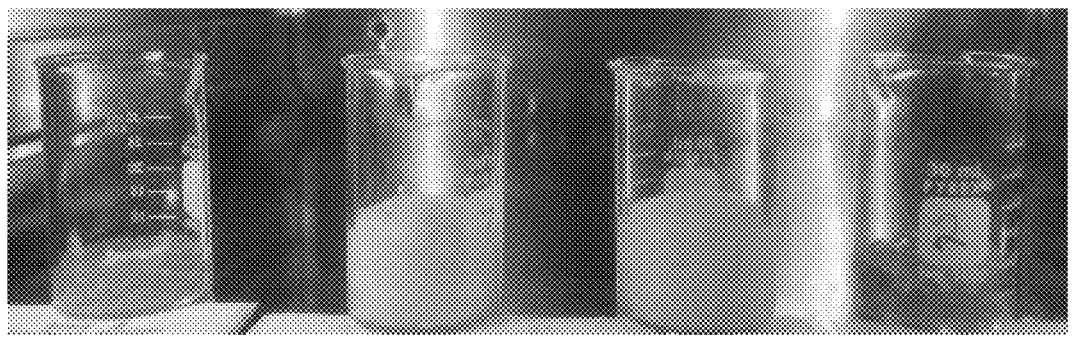

No crystallization of the selected cannabinoid (CBD) was observed using only the cold shock nucleation factor (Solution 1, FIG. 7A). Mechanical agitation of the solution containing the selected cannabinoid (CBD) led to some crystal formation, but the crystallization was incomplete, leaving a large portion of the selected cannabinoid in solution (Solution 3, FIG. 7C). Introduction of a seed crystal to the solution containing the selected cannabinoid (CBD) was not sufficient to crystallize the selected cannabinoid within 24 hours (Solution 4, FIG. 7D) beyond the initially present seed crystal (Solution 4, FIG. 7E). Introduction of a seed crystal, mechanical agitation, and cold shock resulted in partial crystallization of the selected cannabinoid (Solution 5, FIG. 7F). Mechanical agitation, cold shock, and a vacuum led to complete crystallization within 24 hours. (Solution 6, FIG. 7G). Mechanical agitation, the introduction of a seed crystal, and vacuum resulted in complete crystallization within 24 hours. (Solution 7, FIG. 7H). Seed crystal, cold shock, and vacuum resulted in incomplete crystallization within 24 hours. (Solution 8, FIG. 7I). FIG. 7J shows crystallization after 24 hours of samples 8, 7, 6, and 2 (left to right).

Table A5 shows the relative amount of each cannabinoid present in the crystals after crystallization according to the methods described above. Selective crystallization of samples 3, 6, 7, and 8 resulted in enrichment for the selected cannabinoid (CBD) and a decrease in minor cannabinoids such as THC compared to the starting material (base oil). These analyses were conducted prior to the centrifuge separation steps described below. Samples 6 and 7 exhibited the highest amount of crystallization as a proportion of the sample, resulting in a greater % of recovery of the selected cannabinoid (i.e. greater yield). This experiment showed that mechanical agitation of a solution containing a selected cannabinoid and exposure of the same solution to a vacuum resulted in the best crystal formation and purification. The presence of a seed crystal may also aid in enhancing the purification of the selected cannabinoid (CBD). The ability of alternate nucleation factors to influence crystallization, such as increasing/maintaining moisture content and aeration of the solution containing the dissolved cannabinoid, is undergoing validation.

TABLE A6

Composition of Byproduct

| Compound | % by weight (w/w) |
| --- | --- |
| THCA | ND |
| Delta 9-tetrahydrocannabinol (Δ9-THC) | 6.73 |
| CBDA | 1.87 |
| CBD | 56.98 |
| Delta 8-tetrahydrocannabinol (Δ8-THC) | ND |
| CBNA | ND |
| CBN | 0.25 |
| Cannabigerolic acid (CBGA) | ND |
| CBG | 3.50 |
| THCVA | ND |
| THCV | 0.53 |
| CBDVA | ND |
| CBDV | 0.63 |
| CBCA | ND |
| CBC | 6.76 |

The byproduct is fractionally distilled to increase the concentration of a selected cannabinoid, for example, THC, CBDA, CBD, CBN, CBG, THCV, CBDV, or CBC, such that the selected cannabinoid is the highest cannabinoid concentration in the composition and the selected cannabinoid's concentration is above the supersaturation point of the selected cannabinoid.

The solution containing the selected cannabinoid is heated to between 50° C. and 79° C. and mixed until the selected cannabinoid is dissolved. Subsequently, the heated solution is subjected to one or more of the nucleation factors (e.g., vacuum and intense agitation). The crystallized selected cannabinoid is then separated from the solution as described in Example 1B.

TABLE A5

Cannabinoids Present in Each Crystal after Selective Crystallization

| Component (unit) | Base Oil | Solution | | | | | | | |
| --- | --- | --- | --- | --- | --- | --- | --- | --- | --- |
| | | 1 | 2 | 3 | 4 | 5 | 6 | 7 | 8 |
| CBC (mg/g) | 42.7 | 44 | 41.2 | 41.7 | 48.3 | 43.4 | 41.7 | 41.1 | 43.0 |
| Cannabicitran (CBT) (mg/g) | 2.12 | 2.02 | 2.06 | 2.02 | 2 | 2.08 | 2.03 | 2.12 | 2.06 |
| CBD (mg/g) | 693 | 738 | 733 | 742 | 734 | 736 | 747 | 748 | 751 |
| CBDA (mg/g) | 12.5 | 12.4 | 12.3 | 12.6 | 11.9 | 12.4 | 12.3 | 12.1 | 11.4 |
| CBDV (mg/g) | 6.27 | 6.2 | 6.53 | 6.08 | 5.78 | 5.88 | 6.35 | 5.56 | 5.70 |
| CBG (mg/g) | 15.5 | 15.3 | 14.8 | 15.3 | 14.8 | 15.3 | 14.9 | 14.9 | 15.0 |
| CBN (mg/g) | 2.63 | 2.02 | 2.02 | 2.06 | 2.04 | 2.08 | 2.00 | 2.06 | 2.05 |
| THC (% by weight) | 3.61 | 3.55 | 3.55 | 3.51 | 3.52 | 3.53 | 3.43 | 3.49 | 3.34 |
| THCA (% by weight) | <0.01 | <0.01 | <0.01 | <0.01 | <0.01 | <0.01 | <0.01 | <0.01 | <0.01 |
| Potential CBD (% by weight) | 70.4 | 74.9 | 74.4 | 75.3 | 74.5 | 74.7 | 75.8 | 75.9 | 76.1 |
| Potential THC (% by weight) | 3.61 | 3.55 | 3.55 | 3.51 | 3.52 | 3.53 | 3.43 | 3.49 | 3.34 |
| THCV (mg/g) | 1.35 | 1.50 | 1.33 | 1.38 | 1.57 | 1.42 | 1.33 | 1.32 | 1.25 |

Example 3—Selective Crystallization and Purification of a Cannabinoid from the Byproduct of Example 1B The byproduct from the CBD purification described in Example 1B is collected and used as starting material for the crystallization and purification of additional cannabinoids. The composition of the byproduct is shown in Table A6.

Example 4—Unpredictable Natural Crystallization of Cannabinoids from Various Hemp Oils The presently disclosed methods provide a fast and reliable method for achieving high levels of crystallization of selected cannabinoids without the use of exogenous solvents. Persons having skill in the art will be aware that cannabinoid solutions, such as cannabinoid extracts are capable of naturally crystallizing over time. These crystallizations, however, occur slowly, are highly unpredictable, result in non-homogenous and often contaminated crystals, and incomplete crystallization. This example tests the natural crystallization of various samples to provide a comparison point against the artificially induced crystallizations achieved by the presently disclosed methods.

100 grams of each of ten different hemp oil samples (referred to as sample, 1, 2, 3, 4, 5, 6, 7, 8, 9, or 10) were heated to a temperature of 60° C. and incubated for five minutes. Each hemp oil sample was subsequently incubated at room temperature and observed visually every 12 hours. None of the ten samples formed crystals after 4 days. After 95 days, samples 9 (FIG. 15A), 4 (FIG. 15B), 1 (FIG. 15C), and 8 (FIG. 15D) crystallized, and samples 2 (FIG. 15E), 5 (FIG. 15F), 3 (FIG. 15G), 6 (FIG. 15H), 7 (FIG. 15I), and 10 (FIG. 15J) did not crystallize. This example highlights the unpredictability of natural crystallization.

Example 5—Nucleation Factors Improve Crystallization

Crystallization of CBD from a CBD solution in the absence and presence of nucleation factors was evaluated. A first sample of the CBD solution was not exposed to any nucleation factors. The first sample was heated to 60° C., incubated for five minutes, and allowed to cool to room temperature. A second sample of the CBD solution was heated to 60° C. until the CBD was dissolved in the solution and subsequently exposed to the following nucleation factors: cold shock, agitation, seed crystal, and a vacuum of −25 inHg. Cold shock entailed cooling the heated solution to −20° C. and agitation was conducted via vigorous hand mixing.

Figure 11A:
FIG. 11A is an image of a solution containing a plurality of cannabinoids 24 hours after the solution is heated to 60° C. for five minutes and allowed to cool to room temperature.
Figure 11B:
FIG. 11B is an image of CBD crystals formed from a solution containing a plurality of cannabinoids 24 hours after the solution has been heated to 60° C., mixed until the CBD was dissolved, and cooled to −20° C. The cooled solution has been mechanically agitated and exposed to a vacuum oven and a CBD seed crystal.

After 24 hours, in the absence of nucleation factors, visual inspection of the CBD solution appeared to show that the CBD remained in solution (FIG. 11A). In contrast, CBD crystallized in the presence of nucleation factors started forming light crystals within 1 hour (FIG. 11B).

Figure 11C:
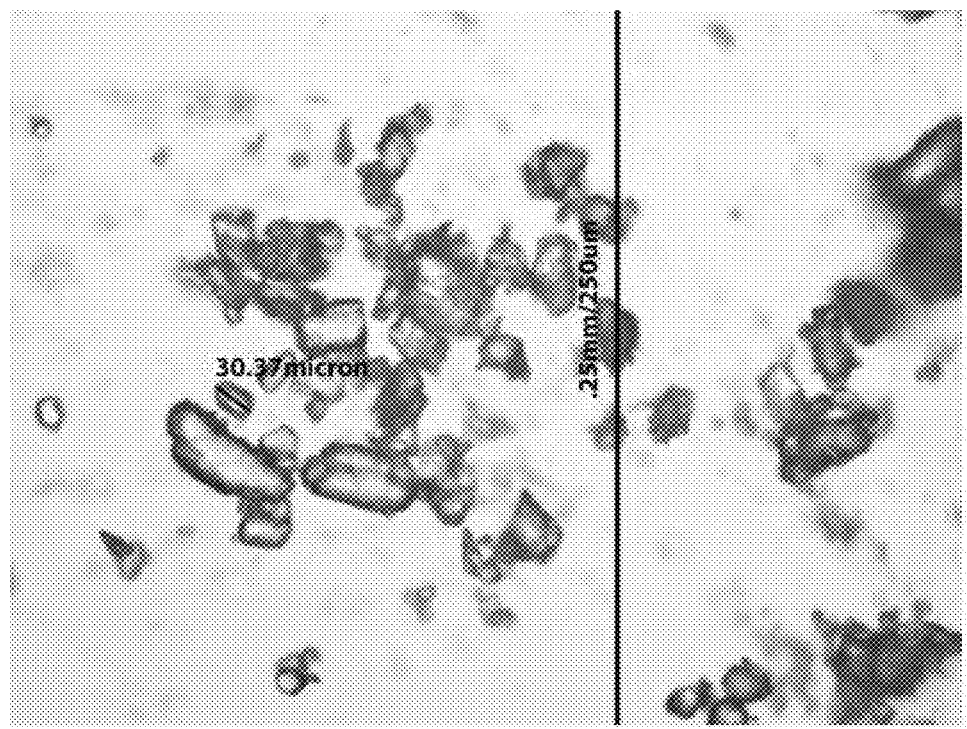
FIG. 11C is a micrograph that shows the size of the CBD crystals of FIG. 11B.
Figure 11D:
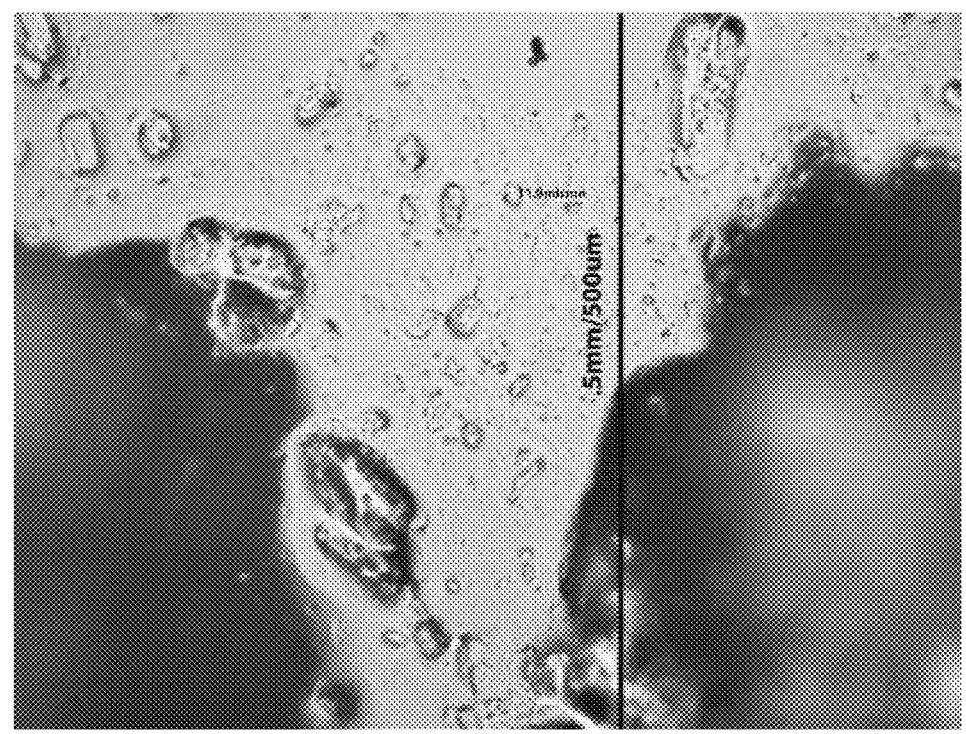
FIG. 11D is a micrograph that shows the size of the CBD crystals of FIG. 11A.

Each sample was subsequently analyzed with a microscope. Under the microscope, the first sample, which was not exposed to nucleation factors, contained some microscopic heterogeneous crystals that were smaller than 25 μm in size (FIG. 11D). These crystals were also contaminated by oils. The sample that is not exposed to nucleation factors is not ideal for cannabinoid purification. In contrast, when the second sample that is exposed to nucleation factors is evaluated under the microscope, homogeneous crystals are observed that are the ideal size for purification (≥25 μm in size) (FIG. 11C). The crystals were also clean, clear, and pure.

Example 6A—Determination of the Minimum Concentration of Cannabinoid Required for Crystallization when the Cannabinoid is the Only Cannabinoid in the Solution The minimum concentration required to crystallize a cannabinoid (e.g., CBD and THCA) in a solution containing only one cannabinoid was determined by evaluating the ability of the cannabinoid (e.g., CBD or THCA) to crystallize at various concentrations. The ability of solutions containing about 75%, about 70%, about 65%, about 60%, about 55%, about 50%, about 45%, about 40%, about 35%, about 30%, about 25%, about 20%, about 15%, about 10%, or about 5% of a selected cannabinoid was evaluated. The cannabinoids were suspended in oleic acid. All samples were heated until the cannabinoid was substantially dissolved in the solution (e.g. 60° C. for about five minutes). These fully dissolved solutions were then exposed to the following nucleation factors: agitation (intense stirring), cold shock (cooling the solution to −20° C. and mixing), introduction of a cannabinoid seed crystal, and exposure to a vacuum at a pressure of −25 inHg). Photographs of the crystallized cannabinoids were taken after 24 hours.

Figure 12A:
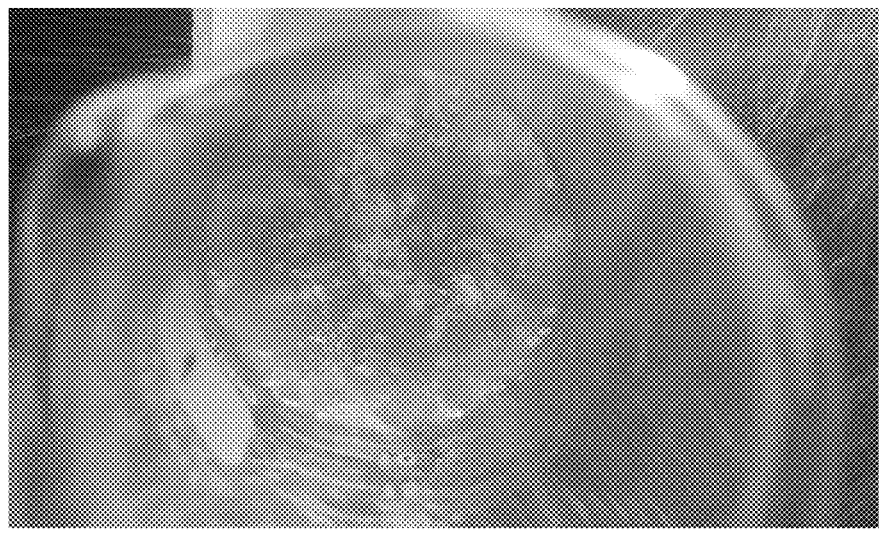
FIGS. 12A-D show CBD crystallization from a solution containing CBD as the only cannabinoid in the solution at concentrations of 60% CBD (FIG. 12A), 50% CBD (FIG. 12B), 40% CBD (FIG. 12C), and 30% CBD (FIG. 12D). After each solution of FIGS. 12A-D was heated to 60° C., the solutions were exposed to the following nucleation factors: agitation (intense stirring), cold shock (cooling solution to −20° C. and mixing), introduction of a CBD seed crystal, and exposure to a vacuum at a pressure of −25 inHg.
Figure 12B:
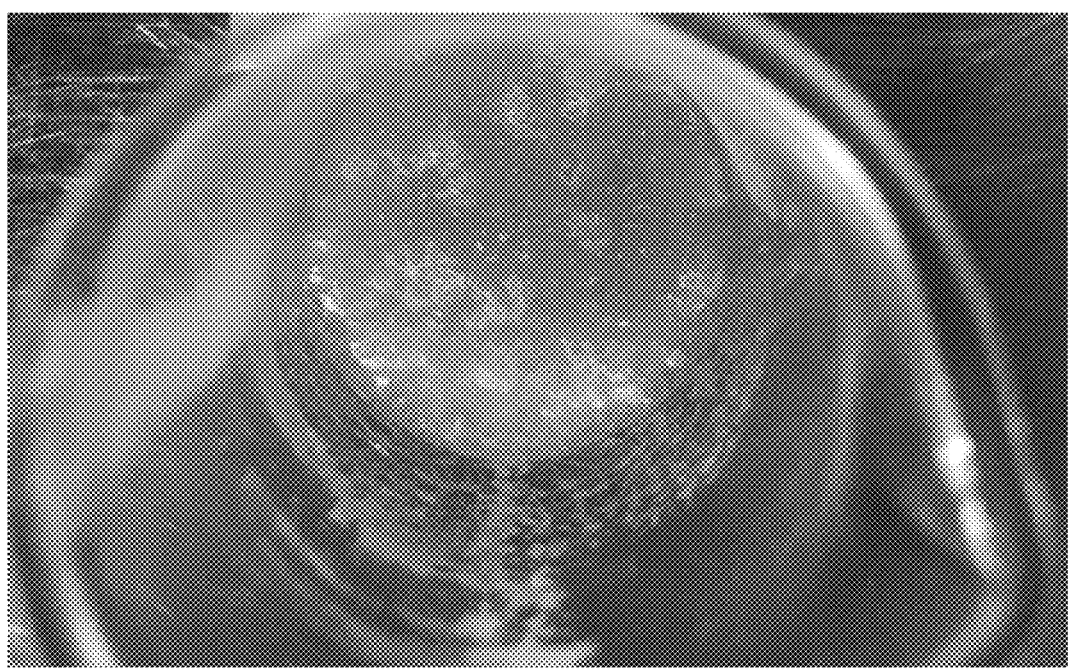
Figure 12C:
Figure 12D:
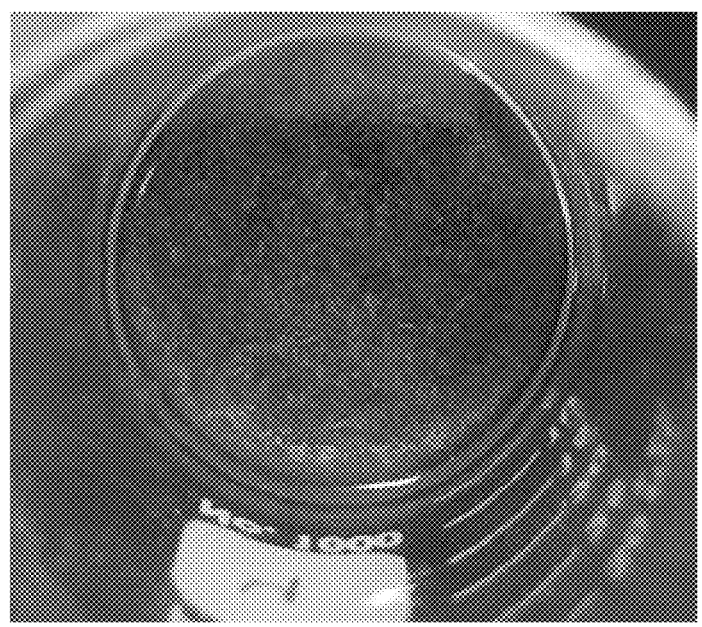
Figure 13A:
FIGS. 13A-D show THCA crystallization from a solution containing THCA as the only cannabinoid in the solution at concentrations of 60% THCA (FIG. 13A), 50% THCA (FIG. 13B), 40% THCA (FIG. 13C), and 30% THCA (FIG. 13D). After each solution of FIGS. 13A-D was heated to 60° C., the solutions were exposed to the following nucleation factors: agitation (intense stirring), cold shock (cooling solution to −20° C. and mixing), introduction of a THCA seed crystal, and exposure to a vacuum at a pressure of −25 inHg.
Figure 13B:
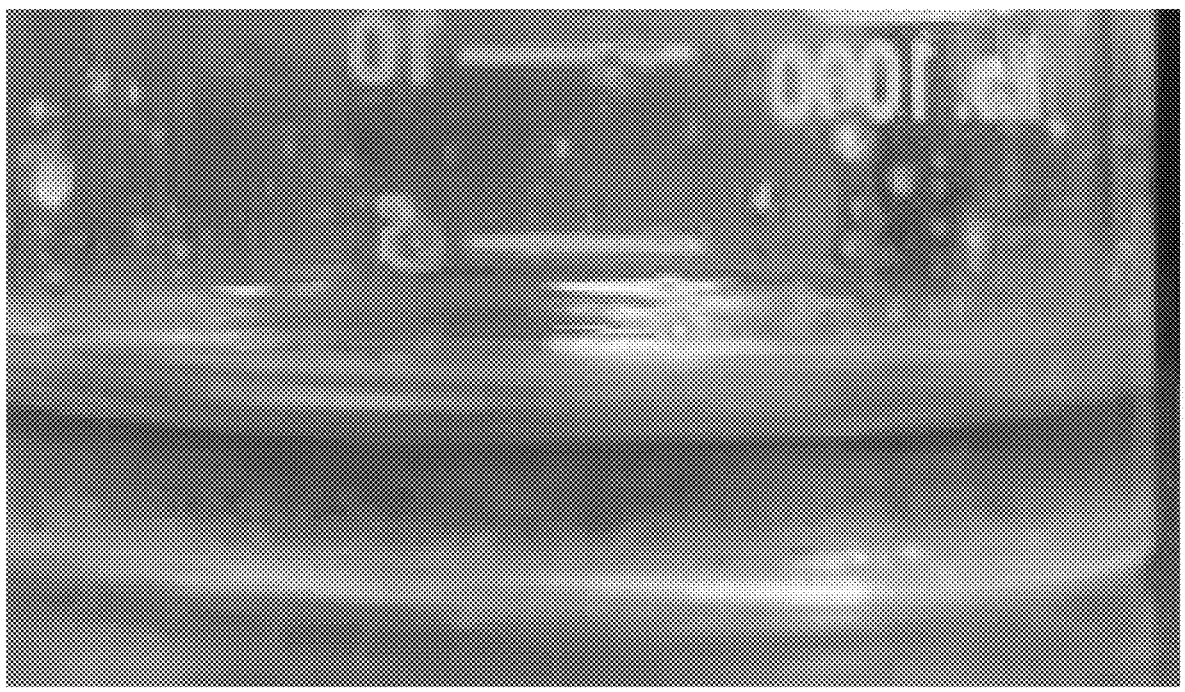
Figure 13C:
Figure 13D:

CBD crystallized from solutions containing 60% CBD (FIG. 12A), 50% CBD (FIG. 12B), 40% CBD (FIG. 12C), and 30% CBD (FIG. 12D). Similarly, THCA crystallized from solutions containing 60% THCA (FIG. 13A), 50% THCA (FIG. 13B), 40% THCA (FIG. 13C), and 30% THCA (FIG. 13D). Thus, all tested concentrations of THCA and CBD crystallized. As expected, higher concentration solutions exhibited more crystals in solution.

Example 6B—Determination of the Minimum Concentration of Selected Cannabinoid Required for Crystallization from a Solution Containing a Plurality of Cannabinoids The minimum concentration of CBD required for selective crystallization from a solution containing a plurality of cannabinoids was evaluated. The composition of the CBD-rich solution comprising a plurality of cannabinoids is shown in Table A7.

TABLE A7

CBD-rich Solution Comprising a Plurality of Cannabinoids.

| Compound | % by weight (w/w) |
| --- | --- |
| THCA | ND |
| Delta 9-tetrahydrocannabinol (Δ9-THC) | 3.85 |
| CBDA | 0.83 |
| CBD | 78.25 |
| Delta 8-tetrahydrocannabinol (Δ8-THC) | ND |
| CBNA | ND |
| CBN | ND |
| Cannabigerolic acid (CBGA) | ND |
| CBG | 1.74 |
| THCVA | ND |
| THCV | 0.24 |
| CBDVA | ND |
| CBDV | 0.54 |
| CBCA | ND |
| CBC | 3.68 |

"ND" refers to a cannabinoid that is not detected.

The ability of CBD to crystallize at the following concentrations was evaluated: 31.3% w/w, 19.6% w/w, 15.7% w/w, 11.7% w/w, 7.8% w/w, and 3.9% w/w. was evaluated. The CBD-rich solution shown in Table A7 was diluted in MCT coconut oil to the aforementioned CBD concentrations. The samples were heated to 60° C. for about five minutes. Then, each solution was subjected to the following nucleation factors: agitation (intense stirring), cold shock (cooling solution to −20° C. and mixing), introduction of a CBD seed crystal, and exposure to a vacuum at a pressure of −25 inHg). Photographs of the crystallized cannabinoids were taken after 24 hours. Table A8 summarizes observations of the solutions at each CBD concentration.

TABLE A8

Observation of Crystallization of CBD from CBD-rich Solution Comprising a Plurality of Cannabinoids

Figure 14A:
FIGS. 14A-F show crystallization of CBD from a CBD-rich solution containing a plurality of cannabinoids. After each solution of FIGS. 14A-D was heated to 60° C., the solutions were exposed to the following nucleation factors: agitation (intense stirring), cold shock (cooling solution to −20° C. and mixing), introduction of a CBD seed crystal, and exposure to a vacuum at a pressure of −25 inHg.

| CBD Concentration (% w/w) | Observation | Figure |
| --- | --- | --- |
| 31.3 | CBD crystallized. The crystals can be isolated using the protocol of Example 1B. | FIG. 14A |

TABLE A8-continued

Observation of Crystallization of CBD from CBD-rich Solution Comprising a Plurality of Cannabinoids

Figure 14B:
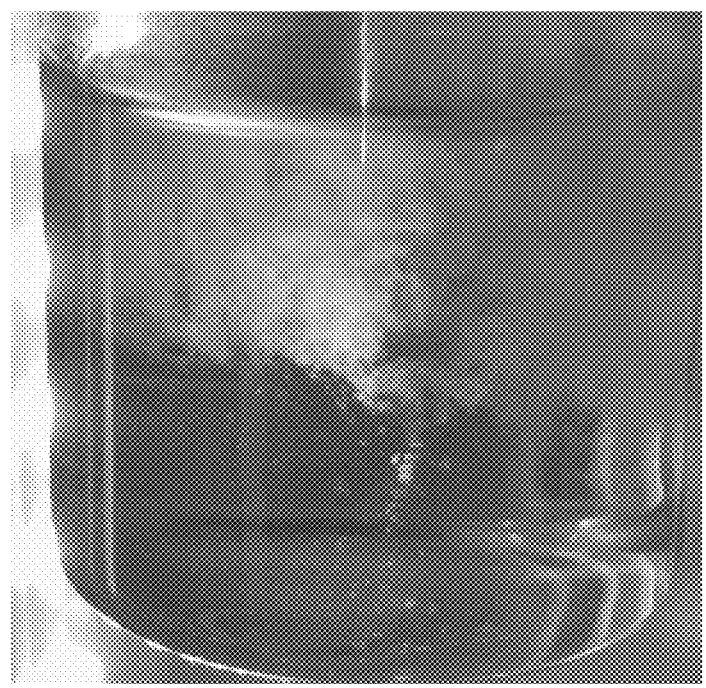
Figure 14C:
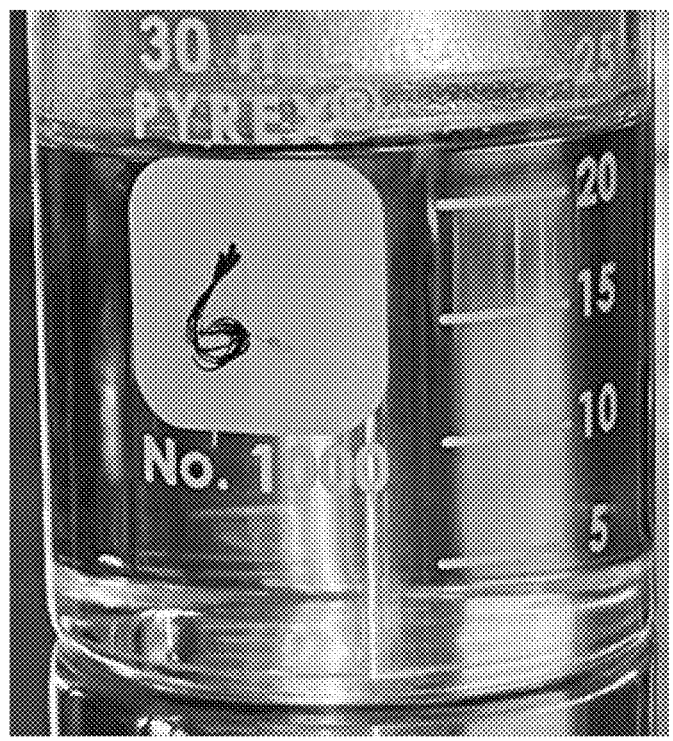
Figure 14D:
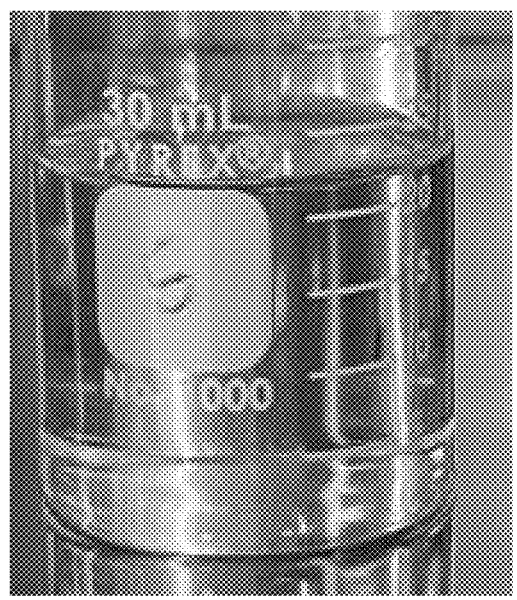
Figure 14E:
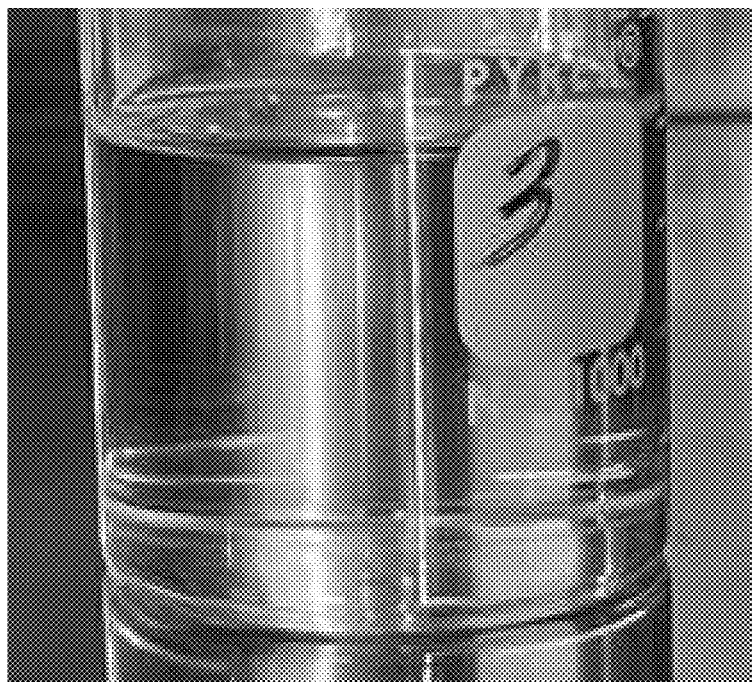
Figure 14F:

| CBD Concentration (% w/w) | Observation | Figure |
|---|---|---|
| 19.6 | CBD crystallized. The crystals can be isolated using the protocol of Example 1B. | FIG. 14B |
| 15.7 | CBD did not crystallize after 24 hours. | FIG. 14C |
| 11.7 | CBD did not crystallize after 24 hours. | FIG. 14D |
| 7 8 | CBD did not crystallize after 24 hours. | FIG. 14E |
| 3.9 | CBD did not crystallize after 24 hours. | FIG. 14F |

The lowest tested concentration of CBD in MCT oil that exhibited crystallization via the presently claimed methods was 19.6%. The experiment was also repeated using mixtures of cannabinoid CBD and THCa isolates in oleic acid. The lowest tested concentration of CBD that crystallized was 24% (FIG. 16), though lower concentrations may also crystallize if tested.

These results were surprising, because traditional solvent-based methods require a minimum selected cannabinoid concentration of at least 80%. The results also demonstrated that the crystallization methods work in different solvents, and in solutions that are completely free from other compounds other than cannabinoids, or in complex mixtures, such as primary cannabinoid extracts.

This process is repeated to determine the minimum concentration of crystallization for alternative cannabinoids, including THC, THCV, CBDA, CBDV, THCA, CBG, CBN, CBDVA, CBNA, CBGA, CBCA, and CBC. This process is also repeated to determine the minimum concentration of crystallization of cannabinoids in alternative solvents, such as olive oil, coconut oil, canola oil, flaxseed oil, avocado oil, sesame oil, canola oil, palm oil, safflower oil, soybean oil, corn oil, peanut oil, walnut oil, flaxseed oil, sunflower oil, palm oil, palm kernel oil, caproic acid, caprylic acid, hempseed oil, and walnut oil.

Figure 8A:
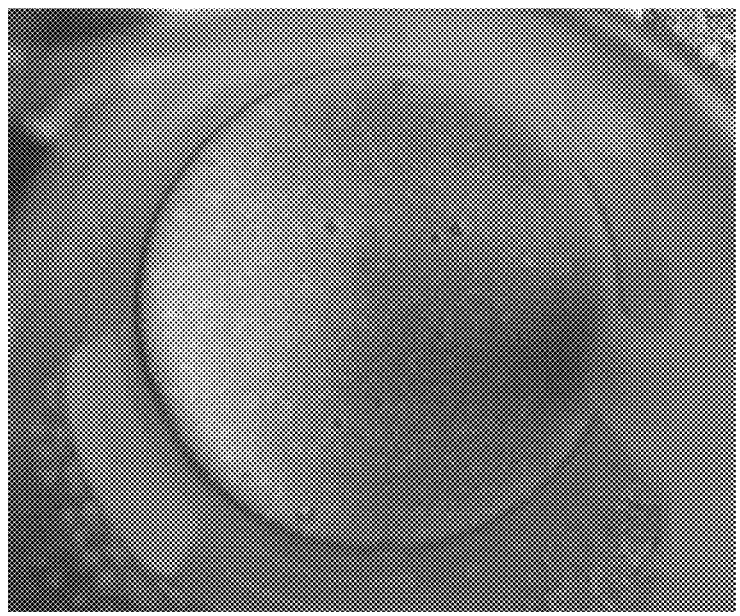
FIGS. 8A-8D are images of a CBD solution containing a plurality of cannabinoids that has heated to 60° C., mixed until the CBD was dissolved, cooled to −20° C., and exposed to a vacuum oven at pressures of −5 inHg (FIG. 8A), −10 inHg (FIG. 8B), −15 inHg (FIG. 8C), or −20 inHg (FIG. 8D). Images are collected one hour after exposure to the vacuum oven.
Figure 8B:
Figure 8C:
Figure 8D:
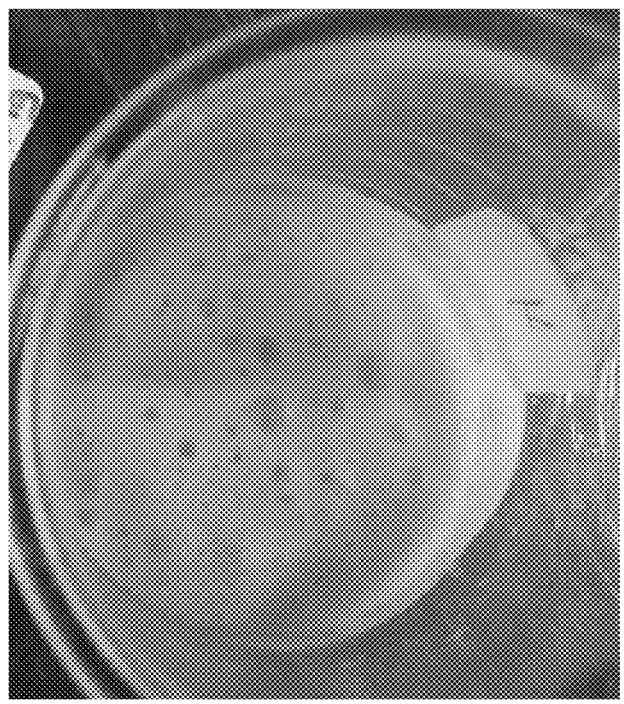

Example 7—Effect of Vacuum Strength on Crystallization of a Selected Cannabinoid The effect of vacuum strength on cannabinoid crystallization was evaluated. All samples were heated to 60° C. for about five minutes. Each solution was then subjected to the following nucleation factors: agitation (intense stirring), cold shock (cooling solution to −20° C. and mixing), introduction of a CBD seed crystal, and exposure to a vacuum oven at a temperature of 34.4° C. for one hour. The following vacuum oven pressures were evaluated: −5 inHg (FIG. 8A), −10 inHg (FIG. 8B), −15 inHg (FIG. 8C), and −20 inHg (FIG. 8D) vacuum.

Cannabinoid crystals exhibit a matte finish, are opaque, have a firm texture, and contain microbubbles. These factors were used to evaluate overall crystallization.

Exposure to all four vacuum pressures resulted in crystallization. Higher vacuum pressures increased the rate of crystallization, which led to the appearance of crystals that appeared matte.

Example 8—Effect of Rotor Stator Homogenizer on Crystal Appearance and Purity CBD was crystallized from a solution containing a plurality of cannabinoids according to the methods of Example 1A. CBD crystals were separated from solution according to the following method. The solution was placed on a filter with a pore size less than 25 µm (Whatman paper), the filter was placed above a filtration flask, and the filtration flask was spun in a centrifuge at a speed of 5000 rpm for 90 minutes. During centrifugation, the temperature was increased from ambient temperature to 40° C. After centrifugation, the solution was cooled to ambient temperature. Subsequently, the solution was centrifuged again at 5000 rpm for 90 minutes. During centrifugation, the temperature was increased from ambient temperature to 40° C. After centrifugation, the crystallized CBD was collected from the filter.

Figure 9A:
FIG. 9A is an image of a CBD crystal washed in the presence of a rotor stator homogenizer.
Figure 9B:
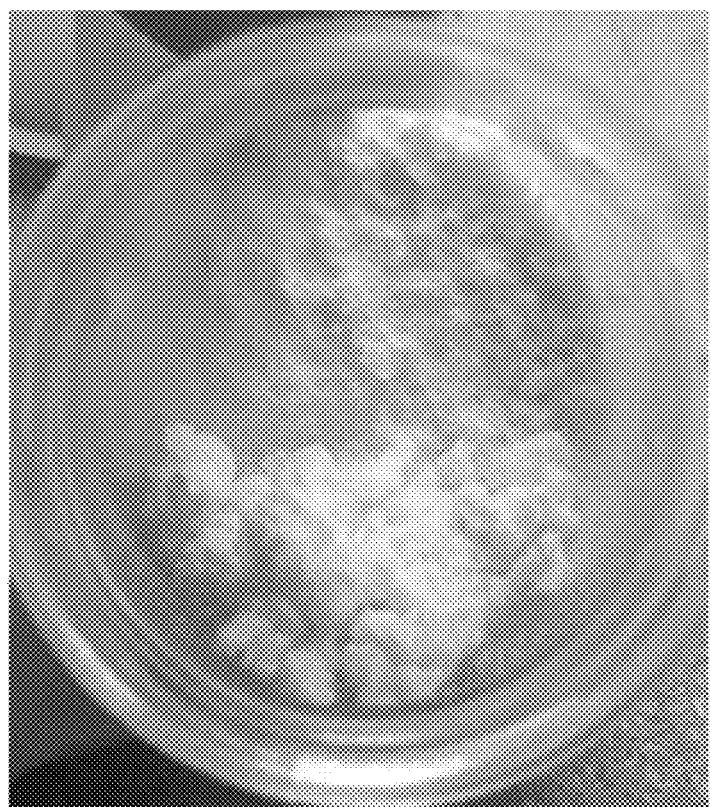
FIG. 9B is an image of a CBD crystal washed in the absence of a rotor stator homogenizer.

The CBD was subsequently placed into a beaker of water at a temperature between 1° C. and 8° C. at a pH of 6.5 with or without a rotor stator homogenizer. If the rotor stator homogenizer was applied to the water containing the CBD crystals, it was applied to the water for five minutes at a speed of 15,000 rpm to disperse the cannabinoid crystals throughout the water. After washing, the CBD mixture was forced through a Whatman paper covering over a 25 µm filtration flask to remove the water. The CBD was collected from the Whatman paper and desiccated to remove any remaining traces of water. The appearance of the crystals was visualized, and the purity of the CBD was determined. The CBD crystals that were washed in the presence of a rotor stator homogenizer was brilliant white with no smell (FIG. 9A). In contrast, CBD crystals washed in the absence of a rotor stator homogenizer were off-white with larger clumps and a characteristic hemp smell (FIG. 9B). Washing in the presence of a rotor stator homogenizer increased the purity of the CBD (Table A9) by 1.3%. Washing also reduced the oil content of the CBD crystals, as determined visually in FIG. 9A and FIG. 9B. As noted above, the consumer qualities of the crystals were significantly improved by the rotostator wash. Persons having skill in the art will recognize other tools that could be used to disperse/mix the crystals with water. Cannabinoid crystals are insoluble in water. Persons having skill in the art will be aware of other solvents that could be used in this wash.

TABLE A9

Cannabinoids Present in Each Solution after Washing with or without a Rotor Stator Homogenizer

| Component (unit) | Washing in the presence of a rotor stator homogenizer | Washing in the absence of a rotor stator homogenizer |
|---|---|---|
| CBC (mg/g) | 4.81 | 4.67 |
| Cannabicitran (CBT) (mg/g) | 0.293 | 0.239 |
| CBD (mg/g) | 936 | 923 |
| CBDA (mg/g) | 2.19 | 2.00 |
| CBDV (mg/g) | 5.33 | 5.31 |
| CBG (mg/g) | 1.79 | 1.77 |
| CBN (mg/g) | 0.335 | 0.316 |
| THC (% by weight) | 0.468 | 0.467 |
| THCA (% by weight) | <0.01 | <0.01 |
| Potential CBD (% by weight) | 93.7 | 92.5 |
| Potential THC (% by weight) | 0.468 | 0.467 |
| THCV (mg/g) | 0.824 | 0.679 |

Example 9—Comparing the Effect of Filtration Techniques on Purity and Appearance of CBD Crystals CBD was crystallized from a solution containing a plurality of cannabinoids according to the methods of Example 1A. The solution was divided into two samples, and the CBD crystals of each sample were separated from solution.

In one sample, the CBD crystals were separated from solution according to the following method. The solution was placed on a filter with a pore size less than 25 μm (Whatman paper), the filter was placed above a filtration flask, and the filtration flask was spun in a centrifuge at a speed of 5000 rpm for 90 minutes. During centrifugation, the temperature was increased from ambient temperature to 40° C. After centrifugation, the solution was cooled to ambient temperature. Subsequently, the solution was centrifuged again at 5000 rpm for 90 minutes. During centrifugation, the temperature was increased from ambient temperature to 40° C. After centrifugation, the crystallized CBD was collected from the filter.

In the other sample, CBD was separated from the solution using vacuum filtration. The CBD crystals obtained from each method were desiccated.

The purity and appearance of each sample was compared.

Figure 10A:
FIG. 10A is an image of a CBD crystal that is separated from a solution containing a plurality of cannabinoids using centrifugation.
Figure 10B:
FIG. 10B is an image of a CBD crystal that is separated from a solution containing a plurality of cannabinoids using vacuum filtration.

Separation of the CBD crystals from solution using the centrifugation procedure resulted in brilliant white, dry CBD crystals that did not have a smell (FIG. 10A). Separation of the CBD crystals from solution using vacuum filtration resulted in orange-yellow CBD crystals that were oily to the touch (FIG. 10B). Separation of the CBD crystals from solution by centrifugation resulted in the formation of CBD crystals that were more pure, e.g., 94.6% pure, than CBD crystals separated from solution by vacuum filtration, e.g., 76.2% pure. Separation of the CBD crystals from solution by centrifugation also resulted in a superior removal of terpenes than CBD crystals separated from solution by vacuum filtration. The cannabinoid profile and terpene profile of the crystals are displayed in Table A10 and Table A11, respectively.

TABLE A10

Cannabinoids Present in Each Solution after Centrifugation or Vacuum Filtration

| Cannabinoid (unit) | CBD Crystals Isolated from solution by centrifugation | CBD Crystals Isolated from solution by by vacuum filtration |
|---|---|---|
| CBC (mg/g) | 4.68 | 39.5 |
| Cannabicitran (CBT) (mg/g) | 0.248 | 2.08 |
| CBD (mg/g) | 945 | 752 |
| CBDA (mg/g) | 1.93 | 11.9 |
| CBDV (mg/g) | 5.17 | 5.48 |
| CBG (mg/g) | 1.71 | 15.2 |
| CBN (mg/g) | 0.351 | 1.99 |
| THC (% by weight) | 0.447 | 3.47 |
| THCA (% by weight) | <0.01 | <0.01 |
| Potential CBD (% by weight) | 94.6 | 76.2 |
| Potential THC (% by weight) | 0.447 | 3.47 |
| THCV (mg/g) | 0.85 | 1.38 |

TABLE A11

Terpenes Present in Each Solution after Centrifugation or Vacuum Filtration

| Terpene (unit) | CBD Crystals Isolated from solution by centrifugation | CBD Crystals Isolated from solution by vacuum filtration |
|---|---|---|
| (-)-alpha-bisabolol | 20.7 mg/kg | 118 mg/kg |
| (-)-beta-pinene | ND | 0.2 mg/kg |
| (-)-guaiol | 25.6 mg/kg | 52.2 mg/kg |
| (-)-isopulegol | ND | ND |
| Alpha-humulene | 6.7 mg/kg | 45.2 mg/kg |
| Alpha-pinene | ND | ND |
| Alpha-terpinene | 4.1 mg/kg | 6.1 mg/kg |
| Beta-caryophyllene | 18.4 mg/kg | 106 mg/kg |
| Beta-myrcene | ND | 11.4 mg/kg |
| Camphene | ND | ND |
| Delta-3-carene | 1.0 mg/kg | 1.7 mg/kg |
| d-limonene | 2.5 mg/kg | 4.1 mg/kg |
| Gamma-terpinene | 2.2 mg/kg | 3.5 mg/kg |
| Geraniol | ND | ND |
| Linalool | 33.1 mg/kg | 33.1 mg/kg |
| Nerolidol | ND | 48.9 mg/kg |
| Ocimene | ND | ND |
| p-isopropyltoluene (p-cymene) | ND | ND |
| terpinolene | 2.6 mg/kg | 3.1 mg/kg |

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as, an acknowledgment or any form of suggestion that they constitute valid prior art or form part of the common general knowledge in any country in the world.

ADDITIONAL NUMBERED EMBODIMENTS OF THE INVENTION

The following embodiments are also envisioned by the present disclosure:

1. A method of crystallizing a selected cannabinoid from a cannabinoid solution, comprising:
   (a) providing a solution containing a substantially dissolved selected cannabinoid;
   (b) exposing the dissolved cannabinoid solution of step (a) to a vacuum for a time period sufficient to crystallize the selected cannabinoid.

1.1 The method of embodiment 1, wherein the solution containing a substantially dissolved cannabinoid contains microbubbles or dissolved air that causes bubbling of the solution when exposed to vacuum.

2. The method of embodiment 1 or 1.1, wherein the solution comprises a plurality of cannabinoids, wherein the selected cannabinoid is present in the solution at a concentration greater than or equal to its supersaturation point, and wherein the selected cannabinoid is the highest concentration cannabinoid in the solution.

2.1 The method of any one of embodiments 1-2, wherein said solution is substantially free of any exogenous solvent.

3. The method of embodiment 2 or 2.1, wherein the supersaturation point is greater than or equal to 19%, or 30% by weight of the solution.

3.1 The method of embodiment 2 or 2.1, wherein the supersaturation point is greater than or equal to 24% by weight of the solution.

4. The method of any one of embodiments 1-3.1, wherein the solution of (a) is produced by increasing the temperature of the cannabinoid solution until the selected cannabinoid is substantially dissolved in the solution.

5. The method of any one of embodiments 1-4, wherein the time period sufficient to crystallize the selected cannabinoid is about 15 minutes, about 30 minutes, about 45 minutes, about 1 hour, about 2 hours, about 3 hours, about 4 hours, about 5 hours, about 6 hours, about 7 hours, about 8 hours, about 9 hours, about 10 hours, or more.

6. The method of any one of embodiments 1-5, wherein the cannabinoid solution is a primary *cannabis* extract.

6.1 The method of embodiment 6, wherein the primary *cannabis* extract is a CO2 extraction or an alcohol extraction of a *cannabis* plant.

6.2 The method of embodiment 6, wherein the primary *cannabis* extract is a CO2 extraction or an alcohol extraction of a cannabinoid-producing microorganism culture.

7. The method of any one of embodiments 4-6.2, wherein the temperature is increased to between about 50° C. and about 79° C.

8. The method of any one of embodiments 1-7, comprising exposing the dissolved cannabinoid solution to an additional nucleation factor after step (b), wherein the nucleation factor is selected from the group consisting of: cold shock, introducing a crystal of the selected cannabinoid into the dissolved cannabinoid solution (seed crystal), mechanically agitating the dissolved cannabinoid solution, and combinations thereof.

9. The method of any one of embodiments 1-7, comprising exposing the dissolved cannabinoid solution to an additional nucleation factor before step (b), wherein the nucleation factor is selected from the group consisting of: cold shock, introducing a crystal of the selected cannabinoid into the dissolved cannabinoid solution (seed crystal), mechanically agitating the dissolved cannabinoid solution, and combinations thereof.

10. The method of any one of embodiments 1-7, comprising mechanically agitating the dissolved cannabinoid solution before step (b).

11. The method of any one of embodiments 1-7, comprising mechanically agitating the dissolved cannabinoid solution after step (b).

12. The method of any one of embodiments 1-11, comprising exposing the dissolved cannabinoid solution to an additional nucleation factor after step (b), wherein the nucleation factor is selected from the group consisting of: increasing or maintaining the moisture content of the solution, aerating the solution, and combinations thereof.

13. The method of any one of embodiments 1-11, comprising exposing the dissolved cannabinoid solution to an additional nucleation factor before step (b), wherein the nucleation factor is selected from the group consisting of: increasing or maintaining the moisture content of the solution, aerating the solution, and combinations thereof.

14. The method of any one of embodiments 1-13, wherein the selected cannabinoid is selected from the group consisting of cannabidiol (CBD), tetrahydrocannabinol (THC), tetrahydrocannabivarin (THCV), cannabidiolic acid (CBDA), cannabidivarin (CBDV), tetrahydrocannabinolic acid (THCA), cannabigerol (CBG), cannabinol (CBN), cannabinolic acid (CBNA), cannabidivarinic acid (CBDVA), cannabigerolic acid (CBGA), cannabichromenic acid (CBCA), and cannabichromene (CBC).

15. The method of any one of embodiments 1-14, wherein the cannabinoid solution is a *Cannabis* oil that is substantially free of cutting agents.

16. The method of any one of embodiments 1-15, wherein the cannabinoid solution comprises less than 1%, 0.9%, 0.8%, 0.7%, 0.6%, 0.5%, 0.4%, 0.3%, 0.2%, or 0.1% by weight of exogenous solvents.

17. The method of any one of embodiments 1-16, wherein at least 80% of the selected cannabinoid is crystallized out of the solution.

18. The method of any one of embodiments 1-17, wherein the selected cannabinoid is crystallized out of solution within about 10 hours.

19. The method of any one of embodiments 1-18, wherein crystals of the selected cannabinoid comprise crystals that are greater than or equal to about 25 μm in size.

20. The method of any one of embodiments 1-19, wherein the vacuum is greater than about −5 inHg, about −10 inHg, about −15 inHg, about −20 inHg, or about −25 inHg.

21. The method of any one of embodiments 1-20, wherein the selected cannabinoid is at least about 75%, at least about 80%, at least about 85%, at least about 90%, at least about 95%, or about 100% dissolved in the solution at the time step (a) is performed.

21.1. The method of any one of embodiments 1-21, wherein the selected cannabinoid is selectively crystallized from the cannabinoid solution.

22. A method of crystallizing a selected cannabinoid from a cannabinoid solution, said method comprising:
(a) providing a solution containing a substantially dissolved selected cannabinoid; and
(b) exposing the dissolved cannabinoid solution of step (a) to a nucleation factor for a time period sufficient to crystallize the selected cannabinoid, wherein the nucleation factor is selected from the group consisting of vacuum, cold shock, introducing a crystal of the selected cannabinoid into the dissolved cannabinoid solution (seed crystal), mechanically agitating the dissolved cannabinoid solution, and combinations thereof.

22.1 The method of embodiment 22, wherein the solution containing a substantially dissolved cannabinoid contains microbubbles or dissolved air that causes bubbling of the solution when exposed to vacuum.

23. The method of embodiment 22 or 22.1, wherein the solution comprises a plurality of cannabinoids, wherein the selected cannabinoid is present in the solution at a concentration greater than or equal to its supersaturation point, and wherein the selected cannabinoid is the highest concentration cannabinoid in the solution.

23.1 The method of any one of embodiments 22-23, wherein said solution is substantially free of any exogenous solvent.

24. The method of embodiment 23 or 23.1, wherein the supersaturation point is greater than or equal to 19%, or 30% by weight of the solution.

24.1 The method of embodiment 23, 23.1, or 24, wherein the supersaturation point is greater than or equal to 24% by weight of the solution.

25. The method of any one of embodiments 22-24.1, wherein the cannabinoid solution of (a) is produced by increasing the temperature of the cannabinoid solution until the selected cannabinoid is substantially dissolved in the solution.

26. The method of any one of embodiments 22-25, wherein at least 50% of the selected cannabinoid is crystallized within about 15 minutes, about 30 minutes, about 45 minutes, about 1 hour, about 2 hours, about 3 hours, about 4 hours, about 5 hours, about 6 hours, about 7 hours, about 8 hours, about 9 hours, or about 10 hours.

27. The method of any one of embodiments 22-26, wherein the cannabinoid solution is a primary *cannabis* extract.

27.1 The method of embodiment 27, wherein the primary *cannabis* extract is a CO2 extraction or an alcohol extraction of a *cannabis* plant.

27.2 The method of embodiment 27, wherein the primary *cannabis* extract is a CO2 extraction or an alcohol extraction of a cannabinoid-producing microorganism culture.

28. The method of any one of embodiments 25-27.2, wherein the temperature is increased to between about 50° C. and about 79° C.

29. The method of any one of embodiments 22-28, comprising exposing the dissolved cannabinoid solution to an additional nucleation factor after step (b), wherein the nucleation factor is selected from the group consisting of: increasing or maintaining the moisture content of the solution, aerating the solution, and combinations thereof.

30. The method of any one of embodiments 22-28, comprising exposing the dissolved cannabinoid solution to an additional nucleation factor before step (b), wherein the nucleation factor is increasing or maintaining the moisture content of the solution, aerating the solution, and combinations thereof.

31. The method of any one of embodiments 22-30, wherein the selected cannabinoid is selected from the group consisting of cannabidiol (CBD), tetrahydrocannabinol (THC), tetrahydrocannabivarin (THCV), cannabidiolic acid (CBDA), cannabidivarin (CBDV), tetrahydrocannabinolic acid (THCA), cannabigerol (CBG), cannabinol (CBN), cannabinolic acid (CBNA), cannabidivarinic acid (CBDVA), cannabigerolic acid (CBGA), cannabichromenic acid (CBCA), and cannabichromene (CBC).

32. The method of any one of embodiments 22-31, wherein the cannabinoid solution is a *Cannabis* oil that is substantially free of cutting agents.

33. The method of any one of embodiments 22-32, wherein the cannabinoid solution comprises less than 1%, 0.9%, 0.8%, 0.7%, 0.6%, 0.5%, 0.4%, 0.3%, 0.2%, or 0.1% exogenous solvents by weight.

34. The method of any one of embodiments 22-33, wherein at least 80% of the selected cannabinoid is crystallized out of the cannabinoid solution.

35. The method of any one of embodiments 22-34, wherein at least 50% of the selected cannabinoid crystalized out of solution within about 10 hours.

36. The method of any one of embodiments 22-35, wherein the crystals of the selected cannabinoid comprise crystals that are greater than or equal to about 25 µm in size.

37. The method of any one of embodiments 22-36, wherein the nucleation factor is vacuum.

38. The method of embodiment 37, wherein the vacuum is greater than about −5 inHg, about −10 inHg, about −15 inHg, about −20 inHg, or about −25 inHg.

39. The method of any one of embodiments 22-38, wherein the selected cannabinoid is at least about 75%, at least about 80%, at least about 85%, at least about 90%, at least about 95%, or about 100% dissolved in the cannabinoid solution at the time step (a) is performed.

39.1. The method of any one of embodiments 22-39, wherein the selected cannabinoid is selectively crystallized from the cannabinoid solution.

40. A method of purifying a selected cannabinoid from a mixture of cannabinoids, said method comprising:
 (a) providing a mixture of cannabinoids comprising a crystallized cannabinoid, wherein the crystallized cannabinoid comprises crystals that are at least about 25 µm in size;
 (b) forcing the mixture of cannabinoids through a filter, said filter having a pore size smaller than about 25 µm; wherein this step is performed at a temperature below the melting point of the crystallized cannabinoid, wherein the crystallized cannabinoid remains on the filter; and
 (c) collecting the crystallized cannabinoid from the filter, thereby purifying the selected cannabinoid.

41. The method of embodiment 40, wherein the crystallized cannabinoid is produced by the method of any one of embodiments 1-39.

42. The method of embodiment 40 or 41, wherein step (b) is performed between about 0.5° C. and 10° C. below the melting point of the crystallized cannabinoid.

43. The method of any one of embodiments 40-42, wherein the selected cannabinoid is selected from the group consisting of consisting of cannabidiol (CBD), tetrahydrocannabinol (THC), tetrahydrocannabivarin (THCV), cannabidiolic acid (CBDA), cannabidivarin (CBDV), tetrahydrocannabinolic acid (THCA), cannabigerol (CBG), cannabigerolic acid (CBGA), cannabinol (CBN), cannabinolic acid (CBNA), cannabidivarinic acid (CBDVA), cannabichromenic acid (CBCA), and cannabichromene (CBC).

44. The method of any one of embodiments 40-43, comprising forcing the mixture of cannabinoids through the filter via centrifugation, application of pressure, or application of a vacuum.

45. The method of any one of embodiments 40-43, comprising forcing the mixture of cannabinoids through the filter via centrifugation.

46. The method of any one of embodiments 40-45, comprising washing the crystallized cannabinoid with a solvent.

47. The method of any one of embodiments 40-46, wherein the collected crystallized cannabinoid is at least 98% pure by weight.

48. A method of purifying a selected cannabinoid from a cannabinoid solution, said method comprising:
 (a) crystallizing the selected cannabinoid from the cannabinoid solution by exposing the cannabinoid solution to a vacuum for a time period sufficient to crystallize the selected cannabinoid, thereby producing cannabinoid crystals; and
 (b) separating the selected cannabinoid crystals from the cannabinoid solution;
 wherein the selected cannabinoid is substantially dissolved in the cannabinoid solution at the time of step (a).

48.1 The method of embodiment 48, wherein the solution containing a substantially dissolved cannabinoid contains microbubbles or dissolved air that causes bubbling of the solution when exposed to vacuum.

49. The method of embodiment 48 or 48.1, wherein the cannabinoid solution comprises a plurality of cannabinoids, wherein the selected cannabinoid is present in the solution at a concentration greater than or equal to its supersaturation point, and wherein the selected cannabinoid is the highest concentration cannabinoid in the solution, and wherein said cannabinoid solution is substantially free of any exogenous solvent.

49.1 The method of any one of embodiments 48-49, wherein said solution is substantially free of any exogenous solvent.

50. The method of embodiment 49 or 49.1, wherein the supersaturation point is greater than or equal to 19%, or 30%, by weight of the cannabinoid solution.

50.1 The method of any one of embodiments 49-50, wherein the supersaturation point is greater than or equal to 24% by weight of the cannabinoid solution.

51. The method of any one of embodiments 48-50.1, wherein the cannabinoid solution of (a) is produced by increasing the temperature of the cannabinoid solution until the selected cannabinoid is substantially dissolved in the solution.

52. The method of any one of embodiments 48-51, wherein at least 95% of the selected cannabinoid crystallizes out of the solution into cannabinoid crystals.

53. The method of any one of embodiments 48-52, wherein step (b) comprises:
    (i) forcing the cannabinoid solution through a filter; wherein this step is performed at a temperature below the melting point of the crystallized cannabinoid; and
    (ii) collecting the crystallized cannabinoid from the filter, thereby separating the selected cannabinoid from the cannabinoid solution.

54. The method of embodiment 53, comprising forcing the cannabinoid solution through the filter via centrifugation, application of pressure, or application of a vacuum.

55. The method of embodiment 53, comprising forcing the cannabinoid solution through the filter via centrifugation.

56. The method of any one of embodiments 48-55, wherein the filter comprises a pore size that is smaller than 2 μm.

57. The method of any one of embodiments 48-56, wherein the cannabinoid solution of (a) is produced by increasing the temperature of the solution to between about 50° C. and about 79° C.

58. The method of any one of embodiments 48-57, comprising exposing the cannabinoid solution to an additional nucleation factor after step (a), wherein the nucleation factor is selected from the group consisting of: cold shock, introducing a crystal of the selected cannabinoid into the dissolved cannabinoid solution (seed crystal), mechanically agitating the dissolved cannabinoid solution, and combinations thereof.

59. The method of any one of embodiments 48-57, comprising exposing the cannabinoid solution to an additional nucleation factor before step (a), wherein the nucleation factor is selected from the group consisting of: cold shock, introducing a crystal of the selected cannabinoid into the dissolved cannabinoid solution (seed crystal), mechanically agitating the dissolved cannabinoid solution, and combinations thereof.

60. The method of any one of embodiments 48-59, comprising exposing the cannabinoid solution to an additional nucleation factor after step (a), wherein the nucleation factor is increasing or maintaining the moisture content of the solution, aerating the solution, and combinations thereof.

61. The method of any one of embodiments 48-59, comprising exposing the cannabinoid solution to an additional nucleation factor before step (a), wherein the nucleation factor is increasing or maintaining the moisture content of the solution, aerating the solution, and combinations thereof.

62. The method of any one of embodiments 48-61, wherein the selected cannabinoid is selected from the group consisting of cannabidiol (CBD), tetrahydrocannabinol (THC), tetrahydrocannabivarin (THCV), cannabidiolic acid (CBDA), cannabidivarin (CBDV), tetrahydrocannabinolic acid (THCA), cannabigerol (CBG), cannabigerolic acid (CBGA), cannabinol (CBN), cannabinolic acid (CBNA), cannabidivarinic acid (CBDVA), cannabichromenic acid (CBCA), and cannabichromene (CBC).

63. The method of any one of embodiments 48-62, wherein the cannabinoid solution is a *Cannabis* oil that does not contain any cutting agents.

63.1 The method of any one of embodiments 48-63, wherein the cannabinoid solution is a primary *cannabis* extract.

63.2 The method of embodiment 63.1, wherein the primary *cannabis* extract is a CO2 extraction or an alcohol extraction of a *cannabis* plant.

63.3 The method of embodiment 63.1, wherein the primary *cannabis* extract is a CO2 extraction or an alcohol extraction of a cannabinoid-producing microorganism culture.

64. The method of any one of embodiments 48-63.3, wherein the cannabinoid solution comprises less than 1%, 0.9%, 0.8%, 0.7%, 0.6%, 0.5%, 0.4%, 0.3%, 0.2%, or 0.1% exogenous solvents by weight.

65. The method of any one of embodiments 48-64, wherein at least 95% of the selected cannabinoid is crystallized out of the solution.

66. The method any one of embodiments 48-65, wherein at least 50% of the selected cannabinoid crystallizes out of solution within about 10 hours.

67. The method of any one of embodiments 48-66 wherein the crystals of the selected cannabinoid comprise crystals that are at least about 25 μm in size.

68. The method of any one of embodiments 48-67, wherein the mixture of cannabinoids is forced through the filter via centrifugation.

68.1 The method of any one of embodiments 48-68, wherein the selected cannabinoid is selectively crystallized from the cannabinoid solution.

69. A method of purifying a selected cannabinoid from a cannabinoid solution, said method comprising:
    (a) crystallizing the selected cannabinoid from the solution by: exposing the cannabinoid solution to a nucleation factor for a time period sufficient to crystallize the selected cannabinoid, wherein the nucleation factor is selected from the group consisting of vacuum, cold shock, introducing a crystal of the selected cannabinoid into the cannabinoid solution (seed crystal), mechanically agitating the cannabinoid solution, and combinations thereof for a time period sufficient to crystallize the selected cannabinoid, thereby producing cannabinoid crystals; and
    (b) separating the selected cannabinoid crystals from the cannabinoid solution;
wherein the selected cannabinoid is substantially dissolved in the cannabinoid solution at the time of step (a).

69.1 The method of embodiment 69, wherein the solution containing a substantially dissolved cannabinoid contains microbubbles or dissolved air that causes bubbling of the solution when exposed to vacuum.

70. The method of embodiment 69 or 69.1, wherein the cannabinoid solution comprises a plurality of cannabinoids, wherein the selected cannabinoid is present in the solution at a concentration greater than or equal to its supersaturation point, and wherein the selected cannabinoid is the highest concentration cannabinoid in the solution.

70.1 The method of any one of embodiments 69-70, wherein said solution is substantially free of any exogenous solvent.

71. The method of embodiment 70 or 70.1, wherein the supersaturation point is greater than or equal to 19%, or 30%, by weight of the solution.

71.1 The method of embodiment 70 or 70.1, wherein the supersaturation point is greater than or equal to 24% by weight of the solution.

72. The method of any one of embodiments 69-71.1, wherein the cannabinoid solution of step (a) is produced by increasing the temperature of the cannabinoid solution until the selected cannabinoid is substantially dissolved in the solution.

73. The method of any one of embodiments 69-72, wherein at least 95% of the selected cannabinoid crystallizes out of the solution into cannabinoid crystals.

74. The method of any one of embodiments 69-73, wherein step (b) comprises:

(i) forcing the cannabinoid solution through a filter; wherein this step is performed at a temperature below the melting point of the crystallized cannabinoid; and (ii) collecting the crystallized cannabinoid from the filter, thereby separating the selected cannabinoid from the cannabinoid solution.

75. The method of embodiment 74, comprising forcing the cannabinoid solution through the filter via centrifugation, application of pressure, or application of a vacuum.

76. The method of embodiment 74, comprising forcing the cannabinoid solution through the filter via centrifugation.

77. The method of any one of embodiments 74-76, wherein the filter comprises a pore size that is smaller than 2 μm.

78. The method of any one of embodiments 69-77, wherein the cannabinoid solution of step (a) is produced by increasing the temperature of the solution to between about 50° C. and about 79° C.

79. The method of any one of embodiments 69-78, comprising exposing the cannabinoid solution to an additional nucleation factor after step (a), wherein the nucleation factor is increasing or maintaining the moisture content of the solution, aerating the solution, and combinations thereof.

80. The method of any one of embodiments 69-78, comprising exposing the cannabinoid solution to an additional nucleation factor before step (a), wherein the nucleation factor is increasing or maintaining the moisture content of the solution, aerating the solution, and combinations thereof.

81. The method of any one of embodiments 69-80, wherein the selected cannabinoid is selected from the group consisting of cannabidiol (CBD), tetrahydrocannabinol (THC), tetrahydrocannabivarin (THCV), cannabidiolic acid (CBDA), cannabidivarin (CBDV), tetrahydrocannabinolic acid (THCA), cannabigerol (CBG), cannabigerolic acid (CBGA), cannabinol (CBN), cannabinolic acid (CBNA), cannabidivarinic acid (CBDVA), cannabichromenic acid (CBCA), and cannabichromene (CBC).

82. The method of any one of embodiments 69-81, wherein the cannabinoid solution is a *Cannabis* oil that does not contain any cutting agents.

82.1 The method of any one of embodiments 69-82, wherein the cannabinoid solution is a primary *cannabis* extract.

82.2 The method of embodiment 82.1, wherein the primary *cannabis* extract is a CO2 extraction or an alcohol extraction of a *cannabis* plant.

82.3 The method of embodiment 82.1, wherein the primary *cannabis* extract is a CO2 extraction or an alcohol extraction of a cannabinoid-producing microorganism culture.

83. The method of any one of embodiments 69-82.3, wherein the cannabinoid solution comprises less than 1%, 0.9%, 0.8%, 0.7%, 0.6%, 0.5%, 0.4%, 0.3%, 0.2%, or 0.1% exogenous solvents by weight.

84. The method of any one of embodiments 69-83, wherein at least 95% of the selected cannabinoid is crystallized out of the solution.

85. The method any one of embodiments 69-84, wherein at least 50% selected cannabinoid crystallizes out of solution within about 10 hours.

86. The method of any one of embodiments 69-85, wherein the crystals of the selected cannabinoid comprise crystals that are at least about 25 μm in size.

87. The method of any one of embodiments 69-86, wherein the cannabinoid solution is forced through the filter via centrifugation.

88. The method of any one of embodiments 69-87, wherein the nucleation factor is vacuum.

89. The method of embodiment 88, wherein the vacuum is greater than about −5 inHg, about −10 inHg, about −15 inHg, about −20 inHg, or about −25 inHg.

90. The method of any one of embodiments 69-89, wherein the selected cannabinoid is at least about 75%, at least about 80%, at least about 85%, at least about 90%, at least about 95%, or about 100% dissolved in the solution at the time step (a) is conducted.

90.1 The method of any one of embodiments 69-90, wherein the selected cannabinoid is selectively crystallized from the cannabinoid solution.

91. A method of crystallizing a selected cannabinoid from a cannabinoid solution, comprising:

(a) providing a cannabinoid solution containing a substantially dissolved selected cannabinoid, wherein the selected cannabinoid is present in the solution at a concentration greater than or equal to its supersaturation point, and wherein the selected cannabinoid is the highest concentration cannabinoid in the solution;

(b) exposing the cannabinoid solution of step (a) to nucleation factors comprising a vacuum and mechanical agitation for a time period sufficient to crystallize the selected cannabinoid.

91.1 The method of embodiment 91, wherein the solution containing a substantially dissolved cannabinoid contains microbubbles or dissolved air that causes bubbling of the solution when exposed to vacuum.

91.2 The method of embodiment 91 or 91.1, wherein said solution is substantially free of any exogenous solvent.

92. The method of embodiment 91, 91.1, or 91.2, wherein the supersaturation point is greater than or equal to 19%, or 30%, by weight of the solution.

93. The method of embodiment 91, 91.1, or 91.2 wherein the supersaturation point is greater than or equal to 24% by weight of the solution.

93.1 The method of any one of embodiments 91-93, wherein the cannabinoid solution is a primary *cannabis* extract.

93.2 The method of embodiment 93.1, wherein the primary *cannabis* extract is a CO2 extraction or an alcohol extraction of a *cannabis* plant.

93.3 The method of embodiment 93.1, wherein the primary *cannabis* extract is a CO2 extraction or an alcohol extraction of a cannabinoid-producing microorganism culture.

94. The method of any one of embodiments 91-93.3, wherein the vacuum is greater than about −5 inHg, −10 inHg, −15 inHg, −20 inHg, or −25 inHg.

95. The method of any one of embodiments 91-94, wherein the selected cannabinoid is selectively crystallized from the cannabinoid solution.

96. A method of purifying a selected cannabinoid from a solution containing a selected cannabinoid, comprising:

(a) selectively crystallizing the selected cannabinoid from the solution by:

(i) providing a cannabinoid solution containing a substantially dissolved selected cannabinoid, wherein the selected cannabinoid is present in the solution at a concentration greater than or equal to its supersaturation point, and wherein the selected cannabinoid is the highest concentration cannabinoid in the solution;

(ii) exposing the cannabinoid solution of step (a)(i) to a nucleation factor for a time period sufficient to crystallize the selected cannabinoid for a time period sufficient to crystallize the selected cannabinoid, wherein the nucleation factor is vacuum and mechanical agitation, thereby producing cannabinoid crystals; and (b) separating the selected cannabinoid crystals from the cannabinoid solution of step (a)(ii).

96.1 The method of embodiment 96, wherein the solution containing a substantially dissolved cannabinoid contains microbubbles or dissolved air that causes bubbling of the solution when exposed to vacuum.

96.2 The method of embodiment 96 or 96.1, wherein said solution is substantially free of any exogenous solvent.

97. The method of embodiment 96, 96.1, or 96.2, wherein the supersaturation point is greater than or equal to 19%, or 30%, by weight of the solution.

98. The method of embodiment 96, 96.1, or 96.2, wherein the supersaturation point is greater than or equal to 24% by weight of the solution.

98.1 The method of any one of embodiments 96-98, wherein the cannabinoid solution is a primary *cannabis* extract.

98.2 The method of embodiment 98.1, wherein the primary *cannabis* extract is a CO2 extraction or an alcohol extraction of a *cannabis* plant.

98.3 The method of embodiment 98.1, wherein the primary *cannabis* extract is a CO2 extraction or an alcohol extraction of a cannabinoid-producing microorganism culture.

99. The method of any one of embodiments 96-98.3, wherein the selected cannabinoid is selectively crystallized from the cannabinoid solution.

100. The method of any one of embodiments 96-99, comprising separating the cannabinoid from the solution by:
 (i) forcing the solution through a filter; and
 (ii) collecting the crystallized cannabinoid from the filter, thereby separating the selected cannabinoid from the cannabinoid solution.

What is claimed is:

1. A method of crystallizing a selected cannabinoid from a cannabinoid solution, comprising:
 (a) providing a cannabinoid solution containing a substantially dissolved selected cannabinoid, wherein the selected cannabinoid is the highest concentration cannabinoid in the solution;
 (b) exposing the cannabinoid solution of step (a) to nucleation factors comprising mechanical agitation and a vacuum for a time period sufficient to crystallize the selected cannabinoid.

2. The method of claim 1, wherein the solution of (a) is produced by increasing the temperature of a cannabinoid solution until the selected cannabinoid is substantially dissolved in the solution.

3. The method of claim 2, wherein the temperature is increased to between about 50° C. and about 79° C.

4. The method of claim 1, wherein the cannabinoid solution is substantially free of any alcohol.

5. The method of claim 1, wherein the cannabinoid solution comprises less than 15% alcohol by weight of the solution.

6. The method of claim 1, wherein the cannabinoid solution is substantially free of any exogenous solvent.

7. The method of claim 1, wherein the cannabinoid solution comprises less than 15% exogenous solvent by weight of the solution.

8. The method of claim 1, comprising exposing the dissolved cannabinoid solution to an additional nucleation factor, wherein the nucleation factor is selected from the group consisting of: cold shock, introducing a crystal of the selected cannabinoid into the dissolved cannabinoid solution, aerating the solution, and combinations thereof.

9. The method of claim 1, comprising mechanically agitating the dissolved cannabinoid solution before exposing the cannabinoid solution to the vacuum.

10. The method of claim 1, comprising mechanically agitating the dissolved cannabinoid solution while the cannabinoid solution is exposed to the vacuum.

11. The method of claim 1, wherein the selected cannabinoid is selected from the group consisting of cannabidiol (CBD), tetrahydrocannabinol (THC), tetrahydrocannabivarin (THCV), cannabidiolic acid (CBDA), cannabidivarin (CBDV), tetrahydrocannabinolic acid (THCA), cannabigerol (CBG), cannabinol (CBN), cannabinolic acid (CBNA), cannabidivarinic acid (CBDVA), cannabigerolic acid (CBGA), cannabichromenic acid (CBCA), and cannabichromene (CBC).

12. The method of claim 1, wherein the selected cannabinoid is CBD.

13. The method of claim 1, wherein the vacuum is stronger than about −5 inHg.

14. A method of purifying a selected cannabinoid from a solution of cannabinoids, said method comprising:
 (a) crystallizing the selected cannabinoid from the solution by:
  (i) providing a cannabinoid solution containing a substantially dissolved selected cannabinoid, wherein the selected cannabinoid is the highest concentration cannabinoid in the solution;
  (ii) exposing the cannabinoid solution of step (a)(i) to a nucleation factor for a time period sufficient to crystallize the selected cannabinoid, wherein the nucleation factor is mechanical agitation and vacuum, thereby producing cannabinoid crystals; and
 (b) separating the selected cannabinoid crystals from the cannabinoid solution of step (a)(ii).

15. The method of claim 14, wherein the cannabinoid solution is substantially free of any alcohol.

16. The method of claim 14, wherein the cannabinoid solution comprises less than 15% alcohol by weight of the solution.

17. The method of claim 14, wherein the cannabinoid solution is substantially free of any exogenous solvent.

18. The method of claim 14, wherein the cannabinoid solution comprises less than 15% exogenous solvent by weight of the solution.

19. The method of claim 14, wherein step (b) comprises:
 (i) forcing the cannabinoid solution and cannabinoid crystals through a filter; wherein this step is performed at a temperature below the melting point of the cannabinoid crystals; and
 (ii) collecting the cannabinoid crystals from the filter, thereby separating the selected cannabinoid from the cannabinoid solution.

20. The method of claim 19, comprising forcing the cannabinoid solution and cannabinoid crystals through the filter via centrifugation, application of pressure, or application of a vacuum.

21. The method of claim 19, comprising forcing the cannabinoid solution and cannabinoid crystals through the filter via centrifugation.

22. The method of claim 14, wherein the solution of (a) is produced by increasing the temperature of the cannabinoid solution until the selected cannabinoid is substantially dissolved in the solution.

23. The method of claim 22, wherein the temperature is increased to between about 50° C. and about 79° C.

24. The method of claim 14, comprising exposing the dissolved cannabinoid solution to an additional nucleation factor, wherein the nucleation factor is selected from the group consisting of: cold shock, introducing a crystal of the selected cannabinoid into the dissolved cannabinoid solution, aerating the solution, and combinations thereof.

25. The method of claim 14, comprising mechanically agitating the dissolved cannabinoid solution before exposing the cannabinoid solution to the vacuum.

26. The method of claim 14, comprising mechanically agitating the dissolved cannabinoid solution while the cannabinoid solution is exposed to the vacuum, or a combination thereof.

27. The method of claim 14, wherein the selected cannabinoid is selected from the group consisting of cannabidiol (CBD), tetrahydrocannabinol (THC), tetrahydrocannabivarin (THCV), cannabidiolic acid (CBDA), cannabidivarin (CBDV), tetrahydrocannabinolic acid (THCA), cannabigerol (CBG), cannabinol (CBN), cannabinolic acid (CBNA), cannabidivarinic acid (CBDVA), cannabigerolic acid (CBGA), cannabichromenic acid (CBCA), and cannabichromene (CBC).

28. The method of claim 14, wherein the selected cannabinoid is CBD.

29. The method of claim 14, wherein the vacuum is stronger than about −5 inHg.

30. A method of purifying a selected cannabinoid from a cannabinoid solution, said method comprising:

(a) crystallizing the selected cannabinoid from the solution by:
  (i) providing a cannabinoid solution containing a substantially dissolved selected cannabinoid, wherein the selected cannabinoid is the highest concentration cannabinoid in the solution;
  (ii) exposing the cannabinoid solution of step (a)(i) to a nucleation factor for a time period sufficient to crystallize the selected cannabinoid, wherein the nucleation factor is mechanical agitation and vacuum, thereby producing cannabinoid crystals; and
(b) separating the selected cannabinoid crystals from the cannabinoid solution of step (a)(ii) by:
  (i) forcing the cannabinoid solution through a filter; wherein this step is performed at a temperature below the melting point of the cannabinoid crystals; and
  (ii) collecting the cannabinoid crystals from the filter, thereby separating the selected cannabinoid from the cannabinoid solution.

* * * * *